United States Patent
Goessling et al.

(10) Patent No.: US 11,040,054 B2
(45) Date of Patent: Jun. 22, 2021

(54) ESTROGEN SENSING THROUGH GPER1 REGULATES NORMAL AND MALIGNANT LIVER GROWTH

(71) Applicant: The Brigham and Women's Hospital, Inc., Boston, MA (US)

(72) Inventors: Wolfram Goessling, Chestnut Hill, MA (US); Saireudee Chaturantabut, Boston, MA (US)

(73) Assignee: The Brigham and Women's Hospital, Inc., Boston, MA (US)

( * ) Notice: Subject to any disclaimer, the term of this patent is extended or adjusted under 35 U.S.C. 154(b) by 0 days.

(21) Appl. No.: 16/349,715

(22) PCT Filed: Nov. 14, 2017

(86) PCT No.: PCT/US2017/061632
§ 371 (c)(1),
(2) Date: May 14, 2019

(87) PCT Pub. No.: WO2018/090049
PCT Pub. Date: May 17, 2018

(65) Prior Publication Data
US 2019/0314399 A1   Oct. 17, 2019

Related U.S. Application Data

(60) Provisional application No. 62/421,627, filed on Nov. 14, 2016.

(51) Int. Cl.
| | | |
|---|---|---|
| *A61K 31/7105* | (2006.01) | |
| *A61P 35/00* | (2006.01) | |
| *A61K 31/713* | (2006.01) | |
| *A61K 38/17* | (2006.01) | |
| *C12Q 1/6886* | (2018.01) | |

(52) U.S. Cl.
CPC ........ *A61K 31/7105* (2013.01); *A61K 31/713* (2013.01); *A61K 38/1774* (2013.01); *A61P 35/00* (2018.01); *C12Q 1/6886* (2013.01); *G01N 2800/52* (2013.01)

(58) Field of Classification Search
CPC .............. A61K 31/7105; A61K 31/713; A61K 38/1774; A61P 35/00; C12O 1/6886
USPC ......................................................... 514/314
See application file for complete search history.

(56) References Cited

U.S. PATENT DOCUMENTS

| | | |
|---|---|---|
| 2003/0148985 A1 | 8/2003 | Morrissey et al. |
| 2010/0190199 A1 | 7/2010 | Filardo et al. |
| 2016/0279157 A1 | 9/2016 | Schentag et al. |

FOREIGN PATENT DOCUMENTS

WO   WO 2015/169173   11/2015

OTHER PUBLICATIONS

Albanito et al., "G protein-coupled receptor 30 (GPR30) mediates gene expression changes and growth response to 17beta-estradiol and selective GPR30 ligand G-1 in ovarian cancer cells," Cancer Res., Feb. 2007, 67:1859-1866.
Baar et al., "Sex-and tissue-specific changes in mTOR signaling with age in C57BL/6J mice," Aging Cell., Feb. 2016, 15(1):155-166.
Barbare et al., "Randomized controlled trial of tamoxifen in advanced hepatocellular carcinoma," J. Clin. Oncol., Jul. 2005, 23(19):4338-4346.
Barros & Gustafsson, "Estrogen receptors and the metabolic network," Cell Metab., Sep. 2011, 14(3):289-299.
Ben-Sahra et al., "mTORC1 induces purine synthesis through control of the mitochondrial tetrahydrofolate cycle," Science, Feb. 2016, 351(6274):728-733.
Ben-Sahra et al., "Stimulation of de novo pyrimidine synthesis by growth signaling through mTOR and S6K1," Science, Mar. 2013, 339(6125):1323-1328.
Carroll et al., "Estrogen defines the dorsal-ventral limit of VEGF regulation to specify the location of the hemogenic endothelial niche," Dev. Cell., May 2014, 29(4):437-453.
Castagnetta et al., "Local estrogen formation by nontumoral, cirrhotic, and malignant human liver tissues and cells," Cancer. Res., Jul. 2003, 63(16):5041-5045.
Chen et al., "Involvement of PI3K/PTEN/AKT/mTOR pathway in invasion and metastasis in hepatocellular carcinoma: Association with MMP-9," Hepatol Res., Feb. 2009, 39(2):177-186.
Chow et al., "High-dose tamoxifen in the treatment of inoperable hepatocellular carcinoma: A multicenter randomized controlled trial," Hepatology, Oct. 2002, 36(5):1221-1226.
Cidon, "Systemic treatment of hepatocellular carcinoma: Past, present and future," World J. Hepatol., Jun. 2017, 9(18):797-807.
Clocchiatti et al., "Sexual dimorphism in cancer," Nat. Rev. Cancer., May 2016, 16(5):330-339.
Cox et al., "Yap reprograms glutamine metabolism to increase nucleotide biosynthesis and enable liver growth," Nat. Cell. Biol., Aug. 2016, 18(8):886-896.
Curado et al., "Conditional targeted cell ablation in zebrafish: a new tool for regeneration studies," Dev. Dyn., Apr. 2007, 236(4):1025-1035.
Dai et al., "Maternal Hepatic Growth Response to Pregnancy in the Mouse," Experimental biology and medicine (Maywood, N.J.)., Nov. 2011, 236(11):1322-1332.
De Bari et al., "Estrogen induces two distinct cholesterol crystallization pathways by activating ERα and GPR30 in female mice," J. Lipid. Res., Sep. 2015, 56(9):1691-700.
Della Corte et al., "Individualized hepatocellular carcinoma risk: the challenges for designing successful chemoprevention strategies," World J. Gastroenterol., Mar. 2013, 19(9):1359-1371.
Dennis et al., "Identification of a GPER/GPR30 antagonist with improved estrogen receptor counterselectivity," J. Steroid Biochem. Mol. Biol., Nov. 2011, 127(3-5): 358-366.

(Continued)

*Primary Examiner* — Yevgeny Valenrod
(74) *Attorney, Agent, or Firm* — Fish & Richardson P.C.

(57) ABSTRACT

Provided herein are methods for the prevention and treatment of an abnormal tissue condition in the liver (e.g., liver cancer) of a subject, based on the administration of an inhibitor of a G protein-coupled estrogen receptor 1 (GPER1).

17 Claims, 64 Drawing Sheets

Specification includes a Sequence Listing.

(56) References Cited

OTHER PUBLICATIONS

Dennis et al., "In vivo effects of a GPR30 antagonist," Nature Chemical Biology, Jun. 2009, 5(6):421-427.
Dimitroulis et al., "From diagnosis to treatment of hepatocellular carcinoma: An epidemic problem for both developed and developing world," World J. Gastroenterol., Aug. 2017, 23(29):5282-5294.
Ding et al., "Haploinsufficiency of target of rapamycin attenuates cardiomyopathies in adult zebrafish," Circ. Res., Sep. 2011, 109(6):658-669.
Dorsam & Gutkind., "G-protein-coupled receptors and cancer," Nat. Rev. Cancer., Feb. 2007, 7(2):79-94.
Dragan et al., "Tumor promotion as a target for estrogen/antiestrogen effects in rat hepatocarcinogenesis," Prev. Med., Jan. 1991, 20(1):15-26.
Drake et al., "Assessment of Mitochondrial Biogenesis and mTORC1 Signaling During Chronic Rapamycin Feeding in Male and Female Mice," The Journals of Gerontology Series A: Biological Sciences and Medical Sciences, Dec. 2013, 68(12):1493-1501.
Evans et al., "Characterisation of Signalling by the Endogenous GPER1 (GPR30) Receptor in an Embryonic Mouse Hippocampal Cell Line (mHippoE-18)," PLoS One., 2016, 11(3):e0152138.
Ferlay et al., "Cancer incidence and mortality worldwide: sources, methods and major patterns in GLOBOCAN 2012," Int. J. Cancer., Mar. 2015, 136(5):E359-86.
Filardo et al., "Estrogen-induced activation of Erk-1 and Erk-2 requires the G protein-coupled receptor homolog, GPR30, and occurs via trans-activation of the epidermal growth factor receptor through release of HB-EGF," Mol. Endocrinol., Oct. 2000, 14(10):1649-1660.
Forbes et al., "COSMIC: exploring the world's knowledge of somatic mutations in human cancer," Nucleic Acids Research, Jan. 2015, 43(Database issue):D805-11.
Francavilla et al., "Hormonal and enzymatic parameters of hepatic regeneration in patients undergoing major liver resections," Hepatology, Oct. 1990, 12(5):1134-1138.
Gershbein., "Pregnancy and liver regeneration in partially hepatectomized rats," Proc. Soc. Exp. Biol. Med., Dec. 1958, 99(3):716-717.
Goessling et al., "APC mutant zebrafish uncover a changing temporal requirement for wnt signaling in liver development," Dev. Biol., Aug. 2008, 320(1):161-174.
Goessling et al., "Genetic interaction of PGE2 and Wnt signaling regulates developmental specification of stem cells and regeneration," Cell., Mar. 2009, 136(6):1136-1147.
Gorelick & Halpern, "Visualization of estrogen receptor transcriptional activation in zebrafish," Endocrinology, Jul. 2011, 152(7):2690-2703.
Guéchot et al., "Sex hormone imbalance in male alcoholic cirrhotic patients with and without hepatocellular carcinoma," Cancer, Aug. 1988, 62(4):760-762.
Haas et al., "Regulatory role of G protein-coupled estrogen receptor for vascular function and obesity," Circ Res. Feb. 2009, 104(3):288-291.
Holm et al., "The G protein-coupled estrogen receptor 1 (GPER1/GPR30) agonist G-1 regulates vascular smooth muscle cell $Ca^{2+}$ handling," J. Vasc. Res., 2013, 50(5):421-429.
Imamura et al., "Preoperative portal vein embolization: an audit of 84 patients," Hepatology, Apr. 1999, 29(4):1099-1105.
Jayasinghe & Volz, "Aberrant ligand-induced activation of G protein-coupled estrogen receptor 1 (GPER) results in developmental malformations during vertebrate embryogenesis," Toxicol. Sci., Jan. 2012, 125(1):262-273.
Kawai et al., "Does estrogen contribute to the hepatic regeneration following portal branch ligation in rats?," Am. J. Physiol. Gastrointest. Liver Physiol., Feb. 2007, 292(2):G582-G589.
Khemlina et al., "The biology of Hepatocellular carcinoma: implications for genomic and immune therapies," Mol. Cancer., Dec. 2017, 16(1):149.

Khetani & Bhatia, "Microscale culture of human liver cells for drug development," Nat. Biotechnol., Jan. 2008, 26(1):120-126.
Kim & Park, "Current immunotherapeutic strategies in hepatocellular carcinoma: recent advances and future directions," Therap. Adv. Gastroenterol., Oct. 2017, 10(10):805-814.
Laplante and Sabatini, "mTOR signaling in growth control and disease," Cell, Apr. 2012, 149(2):274-293.
Lappano et al., "GPER Function in Breast Cancer: An Overview," Front. Endocrinol. (Lausanne), May 2014, 5(66):1-6.
Lee & Edwards, "Stimulation of DNA synthesis and c-fos mRNA expression in primary rat hepatocytes by estrogens," Carcinogenesis, Sep. 2001, 22(9):1473-1481.
Li et al., "Foxa1 and Foxa2 are essential for sexual dimorphism in liver cancer," Cell, Jan. 2012, 148(1-2):72-83.
Liu et al., "G protein-coupled estrogen receptor (GPER) mediates NSCLC progression induced by 17β-estradiol (E 2) and selective agonist G1," Med. Oncol., Apr. 2015, 32:104, 13 pages.
Lloyd, "The regulation of cell size," Cell, Sep. 2013, 154(6):1194-1205.
Longo et al., "Immunotherapeutic approaches for hepatocellular carcinoma," Oncotarget, May 2017, 8(20):33897-33910.
Maggiolini et al., "The G protein-coupled receptor GPR30 mediates c-fos up-regulation by 17beta-estradiol and phytoestrogens in breast cancer cells," J. Biol. Chem., Jun. 2004, 279(26):27008-27016.
Manning and Cantley, "AKT/PKB signaling: navigating downstream," Cell, Jun. 2007, 129(7):1261-1274.
Naugler et al., "Gender disparity in liver cancer due to sex differences in MyD88-dependent IL-6 production," Science, 2007, 317(5834):121-124.
PCT International Prelminary Report on Patentability in International Appln. No. PCT/US2017/061632, dated May 14, 2019, 7 pages.
Prossnitz & Maggiolini, "Mechanisms of estrogen signaling and gene expression via GPR30," Mol. Cell. Endocrinol., Sep. 2009, 308(1-2):32-38.
Prossnitz and Barton, "The G protein-coupled estrogen receptor GPER in health and disease," Nature Reviews, Endocrinology, Aug. 2011, 7(12):715-726.
Prossnitz et al., "Estrogen signaling through the transmembrane G protein—coupled receptor GPR30," Annual Rev. Physiol., Mar. 2008, 70:165-190.
Pupo et al., "Bisphenol A induces gene expression changes and proliferative effects through GPER in breast cancer cells and cancer-associated fibroblasts," Environ. Health Perspect., Aug. 2012, 120(8): 1177-1182.
Revankar et al., "A transmembrane intracellular estrogen receptor mediates rapid cell signaling,". Science, Mar. 2005, 307(5715):1625-1630.
Robitaille et al., "Quantitative phosphoproteomics reveal mTORC1 activates de novo pyrimidine synthesis," Science, May 2013, 339(6125):1320-1323.
Ruiz-Palmero et al., "G protein-coupled estrogen receptor is required for the neuritogenic mechanism of 17β-estradiol in developing hippocampal neurons," Mol. Cell. Endocrinol., Jun. 2013, 372(1-2):105-115.
Sander et al., "Targeted gene disruption in somatic zebrafish cells using engineered TALENs," Nature Biotechnology, Aug. 2011, 29(8):697-698.
Sato et al., "Sex difference in alcohol-related organ injury," Alcohol Clin. Exp. Res., May 2001, 25(5 Suppl ISBRA):40S-45S.
Schulze et al., "Exome sequencing of hepatocellular carcinomas identifies new mutational signatures and potential therapeutic targets," Nature Genetics., Mar. 2015, 47(5):505-511.
Shan et al., "Identification of small molecules for human hepatocyte expansion and iPS differentiation," Nat. Chem. Biol., Aug. 2013, 9(8):514-520.
Spitsbergen et al., "Neoplasia in zebrafish (Danio rerio) treated with 7,12-dimethylbenz[a]anthracene by two exposure routes at different developmental stages," Toxicol. Pathol., Sep. 2000, 28(5):705-715.
Tang et al., "High expression of GPER1, EGFR and CXCR1 is associated with lymph node metastasis in papillary thyroid carcinoma," Int. J. Clin. Exp. Pathol., 2014, 7(6):3213-3223.

(56) References Cited

OTHER PUBLICATIONS

Tang et al., "Reprint of "GPR30 mediates estrogen rapid signaling and neuroprotection"," Mol. Cell. Endocrinol., May 2014, 389(1-2):92-98.
Taper, "The effect of estradiol-17-phenylpropionate and estradiol benzoate on N-nitrosomorpholine-induced liver carcinogenesis in ovariectomized female rats," Cancer, 1978;42(2):462-467.
Thomas & Dong, "Binding and activation of the seven-transmembrane estrogen receptor GPR30 by environmental estrogens: a potential novel mechanism of endocrine disruption," J. Steroid Biochem. Mol. Biol., Dec. 2006, 102(1-5):175-179.
Thomas et al., "Identity of an estrogen membrane receptor coupled to a G protein in human breast cancer cells," Endocrinology, Feb. 2005, 146(2):624-632.
Tsai et al., "Increased 4E-BP1 Expression Protects against Diet-Induced Obesity and Insulin Resistance in Male Mice," Cell Rep., Aug. 2016, 16(7):1903-1914.
Umeda et al., "Partial hepatectomy induces delayed hepatocyte proliferation and normal liver regeneration in ovariectomized mice," Clinical and Experimental Gastroenterology, 2015, 8:175-182.
Villanueva et al., "Pivotal role of mTOR signaling in hepatocellular carcinoma," Gastroenterology, Dec. 2008, 135(6):1972-1983, 1983e1-11.
Vivacqua et al., "17beta-estradiol, genistein, and 4-hydroxytamoxifen induce the proliferation of thyroid cancer cells through the g protein-coupled receptor GPR30," Mol. Pharmacol., Oct. 2006, 70(4):1414-1423.
Vivacqua et al., "The G protein-coupled receptor GPR30 mediates the proliferative effects induced by 17β-estradiol and hydroxytamoxifen in endometrial cancer cells," Mol Endocrinol., Mar. 2006, 20(3):631-646.
Wei et al., "G protein-coupled estrogen receptor deficiency accelerates liver tumorigenesis by enhancing inflammation and fibrosis," Cancer Lett., Nov. 2016, 382(2):195-202.
Wei et al., "The activation of G protein-coupled receptor 30 (GPR30) inhibits proliferation of estrogen receptor-negative breast cancer cells in vitro and in vivo," Cell Death Dis., Oct. 2014, 5(10):e1428.
Williams et al., "Initiating activity of the anti-estrogen tamoxifen, but not toremifene in rat liver," Carcinogenesis, Nov. 1997, 18(11):2247-2253.
Yuan et al., "A positive/negative ion-switching, targeted mass spectrometry-based metabolomics platform for bodily fluids, cells, and fresh and fixed tissue," Nat Protoc., May 2012, 7(5):872-881.
International Search Report and Written Opinion dated Mar. 7, 2018 in International Application No. PCT/US2017/061632, 12 pgs.
Corte et al., "Individualized hepatocellular carcinoma risk: The challenges for designing successful chemoprevention strategies," World J. Gastroenterol 19(9): 1359-1371 (Mar. 2013).

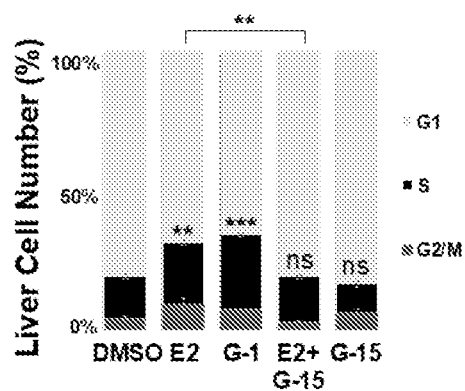
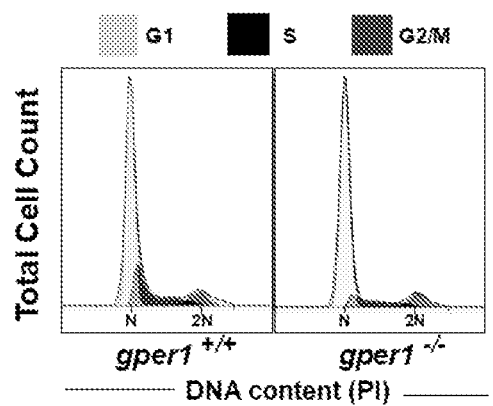
FIG. 3B
FIG. 3C

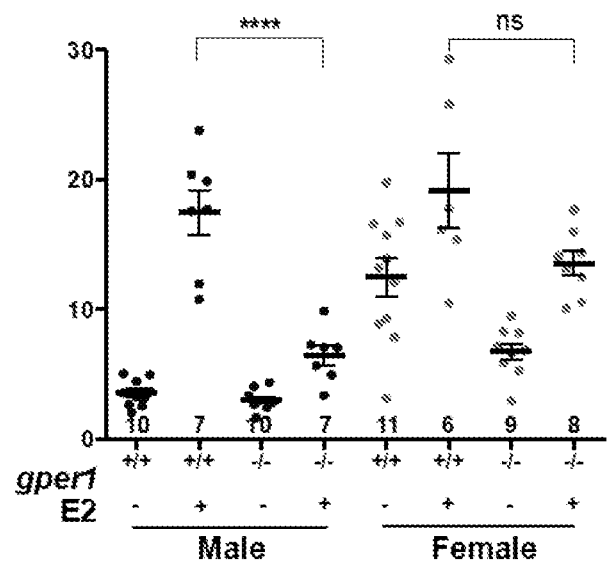
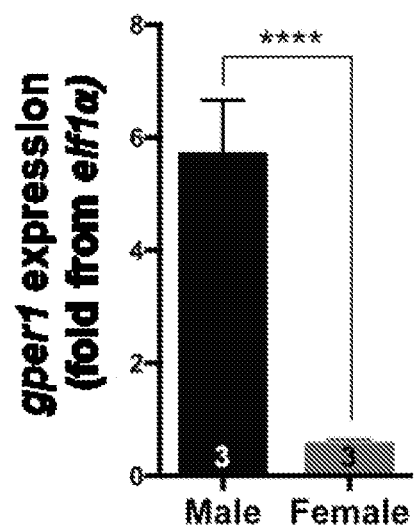
FIG. 6B
FIG. 6C

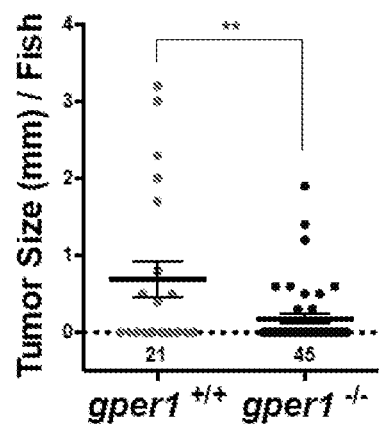
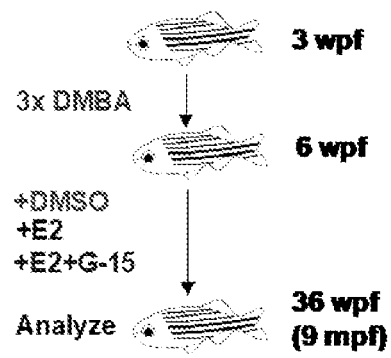
FIG. 7D                    FIG. 7E

| Sample | GO Term (Biological Process) | P-Value |
|---|---|---|
| Female Liver E2-upregulated genes | Convergent extension involved in gastrulation | 2.00E-02 |
| | convergent extension | 3.70E-02 |

| Sample | Metabolic Pathways | P-Value |
|---|---|---|
| Female Liver E2-upregulated metabolites | Ammonia recycling | 4.50E-02 |
| | Glutamate metabolism | 4.50E-02 |

(SEQ ID NO: 1)
(SEQ ID NO: 2)

SEQUENCE LISTING

```
<160> NUMBER OF SEQ ID NOS: 20

<210> SEQ ID NO 1
<211> LENGTH: 60
<212> TYPE: DNA
<213> ORGANISM: Artificial Sequence
<220> FEATURE:
<223> OTHER INFORMATION: genomic fragments

<400> SEQUENCE: 1
gtgattcaga tttatgtgaa tggcaccgag cagttcaatg cttcgtttga cttcaacata    60

<210> SEQ ID NO 2
<211> LENGTH: 31
<212> TYPE: DNA
<213> ORGANISM: Artificial Sequence
<220> FEATURE:
<223> OTHER INFORMATION: genomic fragments

<400> SEQUENCE: 2
gcagttcaat gcttcgtttg acttcaacat a                                    31

<210> SEQ ID NO 3
<211> LENGTH: 375
<212> TYPE: PRT
<213> ORGANISM: Homo sapiens

<400> SEQUENCE: 3

Met Asp Val Thr Ser Gln Ala Arg Gly Val Gly Leu Glu Met Tyr Pro
1               5                   10                  15

Gly Thr Ala Gln Pro Ala Ala Pro Asn Thr Thr Ser Pro Glu Leu Asn
            20                  25                  30

Leu Ser His Pro Leu Leu Gly Thr Ala Leu Ala Asn Gly Thr Gly Glu
        35                  40                  45

Leu Ser Glu His Gln Gln Tyr Val Ile Gly Leu Phe Leu Ser Cys Leu
    50                  55                  60

Tyr Thr Ile Phe Leu Phe Pro Ile Gly Phe Val Gly Asn Ile Leu Ile
65                  70                  75                  80

Leu Val Val Asn Ile Ser Phe Arg Glu Lys Met Thr Ile Pro Asp Leu
                85                  90                  95

Tyr Phe Ile Asn Leu Ala Val Ala Asp Leu Ile Leu Val Ala Asp Ser
                100                 105                 110

Leu Ile Glu Val Phe Asn Leu His Glu Arg Tyr Tyr Asp Ile Ala Val
            115                 120                 125

Leu Cys Thr Phe Met Ser Leu Phe Leu Gln Val Asn Met Tyr Ser Ser
        130                 135                 140

Val Phe Phe Leu Thr Trp Met Ser Phe Asp Arg Tyr Ile Ala Leu Ala
```

```
145                 150                 155                 160
Arg Ala Met Arg Cys Ser Leu Phe Arg Thr Lys His His Ala Arg Leu
                165                 170                 175

Ser Cys Gly Leu Ile Trp Met Ala Ser Val Ser Ala Thr Leu Val Pro
            180                 185                 190

Phe Thr Ala Val His Leu Gln His Thr Asp Glu Ala Cys Phe Cys Phe
            195                 200                 205

Ala Asp Val Arg Glu Val Gln Trp Leu Glu Val Thr Leu Gly Phe Ile
        210                 215                 220

Val Pro Phe Ala Ile Ile Gly Leu Cys Tyr Ser Leu Ile Val Arg Val
225                 230                 235                 240

Leu Val Arg Ala His Arg His Arg Gly Leu Arg Pro Arg Arg Gln Lys
                245                 250                 255

Ala Leu Arg Met Ile Leu Ala Val Val Leu Val Phe Phe Val Cys Trp
            260                 265                 270

Leu Pro Glu Asn Val Phe Ile Ser Val His Leu Leu Gln Arg Thr Gln
        275                 280                 285

Pro Gly Ala Ala Pro Cys Lys Gln Ser Phe Arg His Ala His Pro Leu
    290                 295                 300

Thr Gly His Ile Val Asn Leu Ala Ala Phe Ser Asn Ser Cys Leu Asn
305                 310                 315                 320

Pro Leu Ile Tyr Ser Phe Leu Gly Glu Thr Phe Arg Asp Lys Leu Arg
                325                 330                 335

Leu Tyr Ile Glu Gln Lys Thr Asn Leu Pro Ala Leu Asn Arg Phe Cys
            340                 345                 350

His Ala Ala Leu Lys Ala Val Ile Pro Asp Ser Thr Glu Gln Ser Asp
        355                 360                 365

Val Arg Phe Ser Ser Ala Val
    370                 375

<210> SEQ ID NO 4
<211> LENGTH: 1128
<212> TYPE: DNA
<213> ORGANISM: Homo sapiens

<400> SEQUENCE: 4
atggatgtga cttcccaagc ccggggcgtg ggcctggaga tgtacccagg caccgcgcag      60
cctgcggccc ccaacaccac ctcccccgag ctcaacctgt cccacccgct cctgggcacc     120
gccctggcca atgggacagg tgagctctcg gagcaccagc agtacgtgat cggcctgttc     180
ctctcgtgcc tctacaccat cttcctcttc cccatcggct tgtgggcaa catcctgatc      240 ctggtggtga acatcagctt ccgcgagaag atgaccatcc ccgacctgta cttcatcaac     300
ctggcggtgg cggacctcat cctggtggcc gactccctca ttgaggtgtt caacctgcac     360
gagcggtact acgacatcgc cgtcctgtgc accttcatgt cgctcttcct gcaggtcaac     420
atgtacagca gcgtcttctt cctcacctgg atgagcttcg accgctacat cgccctggcc     480
agggccatgc gctgcagcct gttccgcacc aagcaccacg cccggctgag ctgtggcctc     540
atctggatgg catccgtgtc agccacgctg gtgcccttca ccgccgtgca cctgcagcac     600
accgacgagg cctgcttctg tttcgcggat gtccgggagg tgcagtggct cgaggtcacg     660
ctgggcttca tcgtgccctt cgccatcatc ggcctgtgct actccctcat tgtccgggtg     720
ctggtcaggg cgcaccggca ccgtgggctg cggcccggc ggcagaaggc gctccgcatg     780
atcctcgcgg tggtgctggt cttcttcgtc tgctggctgc cggagaacgt cttcatcagc     840
```

```
gtgcacctcc tgcagcggac gcagcctggg gccgctccct gcaagcagtc tttccgccat    900 gcccacccc  tcacgggcca cattgtcaac ctcgccgcct tctccaacag ctgcctaaac    960
cccctcatct acagctttct cggggagacc ttcagggaca agctgaggct gtacattgag   1020
cagaaaacaa atttgccggc cctgaaccgc ttctgtcacg ctgccctgaa ggccgtcatt   1080
ccagacagca ccgagcagtc ggatgtgagg ttcagcagtg ccgtgtag                1128
```

```
<210> SEQ ID NO 5
<211> LENGTH: 25
<212> TYPE: DNA
<213> ORGANISM: Artificial Sequence
<220> FEATURE:
<223> OTHER INFORMATION: Morpholino oligonucleotide targeting esr1

<400> SEQUENCE: 5
aggaaggttc ctccagggct tctct                                            25

<210> SEQ ID NO 6
<211> LENGTH: 25
<212> TYPE: DNA
<213> ORGANISM: Artificial Sequence
<220> FEATURE:
<223> OTHER INFORMATION: Morpholino oligonucleotide targeting esr2a

<400> SEQUENCE: 6
acatggtgaa ggcggatgag ttcag                                            25

<210> SEQ ID NO 7
<211> LENGTH: 25
<212> TYPE: DNA
<213> ORGANISM: Artificial Sequence
<220> FEATURE:
<223> OTHER INFORMATION: Morpholino oligonucleotide targeting

<400> SEQUENCE: 7
agctcatgct ggagaacaca agaga                                            25

<210> SEQ ID NO 8
<211> LENGTH: 25
<212> TYPE: DNA
<213> ORGANISM: Artificial Sequence
<220> FEATURE:
<223> OTHER INFORMATION: Morpholino oligonucleotide targeting gper1

<400> SEQUENCE: 8
acattggtag tctgctcctc catgc                                            25

<210> SEQ ID NO 9
<211> LENGTH: 25
<212> TYPE: DNA
<213> ORGANISM: Artificial Sequence
<220> FEATURE:
<223> OTHER INFORMATION: Morpholino oligonucleotide targeting gper1

<400> SEQUENCE: 9
gctgcaacac ctgttataag agaaa                                            25

<210> SEQ ID NO 10
<211> LENGTH: 25
<212> TYPE: DNA
<213> ORGANISM: Artificial Sequence
<220> FEATURE:
<223> OTHER INFORMATION: Morpholino oligonucleotide targeting mtor
```

```
<400> SEQUENCE: 10
ggtttgacac attaccctga gcatg                                          25

<210> SEQ ID NO 11
<211> LENGTH: 25
<212> TYPE: DNA
<213> ORGANISM: Artificial Sequence
<220> FEATURE:
<223> OTHER INFORMATION: Morpholino oligonucleotide targeting control

<400> SEQUENCE: 11
cctcttacct cagttacaat ttata                                          25

<210> SEQ ID NO 12
<211> LENGTH: 20
<212> TYPE: DNA
<213> ORGANISM: Artificial Sequence
<220> FEATURE:
<223> OTHER INFORMATION: PCR primer gper1 forward

<400> SEQUENCE: 12
tcaagttgcc gtcacaatgc                                                20

<210> SEQ ID NO 13
<211> LENGTH: 20
<212> TYPE: DNA
<213> ORGANISM: Artificial Sequence
<220> FEATURE:
<223> OTHER INFORMATION: PCR primer gper1 reverse

<400> SEQUENCE: 13
gtcatcctct ccctgtggtt                                                20

<210> SEQ ID NO 14
<211> LENGTH: 20
<212> TYPE: DNA
<213> ORGANISM: Artificial Sequence
<220> FEATURE:
<223> OTHER INFORMATION: PCR primer ef1-alpha forward

<400> SEQUENCE: 14
gcgtcatcaa gagcgttgag                                                20

<210> SEQ ID NO 15
<211> LENGTH: 20
<212> TYPE: DNA
<213> ORGANISM: Artificial Sequence
<220> FEATURE:
<223> OTHER INFORMATION: PCR primer ef1-alpha reverse

<400> SEQUENCE: 15
ttggaacggt gtgattgagg                                                20

<210> SEQ ID NO 16
<211> LENGTH: 27
<212> TYPE: DNA
<213> ORGANISM: Artificial Sequence
<220> FEATURE:
<223> OTHER INFORMATION: PCR primer mtor forward

<400> SEQUENCE: 16
ataagaaaag aaaccacatg tcatacc                                        27

<210> SEQ ID NO 17
<211> LENGTH: 23
```

```
<212> TYPE: DNA
<213> ORGANISM: Artificial Sequence
<220> FEATURE:
<223> OTHER INFORMATION: PCR primer mtor reverse

<400> SEQUENCE: 17
cttaccactc agagagacca aag                                           23

<210> SEQ ID NO 18
<211> LENGTH: 25
<212> TYPE: DNA
<213> ORGANISM: Artificial Sequence
<220> FEATURE:
<223> OTHER INFORMATION: PCR primer mtor LTR

<400> SEQUENCE: 18
ccctaagtac ttgtactttc acttg                                         25

<210> SEQ ID NO 19
<211> LENGTH: 21
<212> TYPE: DNA
<213> ORGANISM: Artificial Sequence
<220> FEATURE:
<223> OTHER INFORMATION: PCR primer gper1 forward

<400> SEQUENCE: 19
ctcgtgaata aagtgttgca g                                             21

<210> SEQ ID NO 20
<211> LENGTH: 19
<212> TYPE: DNA
<213> ORGANISM: Artificial Sequence
<220> FEATURE:
<223> OTHER INFORMATION: PCR primer gper1 reverse

<400> SEQUENCE: 20
gcagtcttgt ttcctccag                                                19
```

ESTROGEN SENSING THROUGH GPER1 REGULATES NORMAL AND MALIGNANT LIVER GROWTH

CLAIM OF PRIORITY

This application is a national stage application under 35 USC § 371 of International Application No. PCT/US2017/061632, filed on Nov. 14, 2017, which claims the benefit of U.S. Provisional Application Ser. No. 62/421,627, filed on Nov. 14, 2016. The entire contents of the foregoing are incorporated herein by reference.

FEDERALLY SPONSORED RESEARCH OR DEVELOPMENT

This invention was made with Government support under Grant Nos. 5K08CA172288, R24OD017870, R01DK090311, and R01DK105198 awarded by the National Institutes of Health. The Government has certain rights in the invention.

TECHNICAL FIELD

Described herein are methods for the prevention and treatment of an abnormal growth condition in the liver tissue of a subject, comprising administering an inhibitor (e.g., an antagonist) of G protein-coupled estrogen receptor 1 (GPER1).

BACKGROUND

Hepatocellular carcinoma (HCC) is the most common type of primary liver cancer, and is a leading cause of global cancer related mortality (Khemlina et al. (2017) Mol. Cancer 16:149. HCC represents approximately 90% of primary liver cancer cases. Other liver cancers include cholangiocarcinoma, which is a bile duct neoplasm accounting for about 10% of primary liver cancers, and fibrolamellar carcinoma which accounts for less than 1% of primary liver cancers. Risk factors associated with HCC include chronic viral infections (e.g., with hepatitis B or hepatitis C viruses), diabetes, alcohol abuse, cirrhosis, and steatohepatitis (i.e., fatty liver) (Della Corte (2013) *World J. Gastroenterol.* 19(9): 1359-71). HCC tumors are very malignant and their diagnosis often offers a poor prognosis. Treatment options for HCC are limited, and include surgical resection, chemotherapy, radiotherapy, liver transplantation, chemoembolization, cryosurgery, or a combination of therapies. However, currently available treatments are unsatisfactory given the high recurrence rates and accompanying cirrhosis (Kim and Park (2017) *Therap. Adv. Gastroenterol* 10(10): 805-14).

Clinical biomarkers and therapies that are useful for the detection and prevention of HCC have not been identified. Thus, there is a need in the art for clinically relevant biomarkers and targets that provide a tool for the diagnosis and a target for the prevention and/or treatment of HCC, particularly in subjects having a risk factor for the disease.

SUMMARY

The present application provides new insights into how liver growth, including malignant liver growth is promoted by 17β-estradiol (E2), which induces cell cycle progression and increases hepatocyte proliferation and liver size. Described herein is the identification of the G protein-coupled receptor 1 (GPER1) as the receptor that mediates E2 regulation of liver growth and downstream activation of PI3K/mTOR signaling. Importantly, inhibition of GPER1 prevents E2-induced liver growth (e.g., tumor growth), thereby representing a new therapeutic target for the treatment and prevention of liver cancer (e.g., hepatocellular carcinoma).

In one aspect, the invention provides methods of treating a subject having liver cancer, the methods comprising administering a therapeutically effective amount of an inhibitor of G protein-coupled estrogen receptor 1 (GPER1), thereby treating the liver cancer in the subject.

In another aspect, the invention provides methods of preventing the development of an abnormal growth condition in a liver tissue of a subject, the method comprising administering an inhibitor of GPER1 to a subject in need thereof, thereby preventing the development of the abnormal growth condition. In some embodiments, the abnormal growth condition is liver cancer. In some embodiments, the liver cancer comprises hepatocellular carcinoma (HCC), cholangiocarcinoma, fibrolamellar carcinoma, or hepatoblastoma.

In some embodiments, the subject has been diagnosed with hepatic steatosis, a hepatitis B viral infection, a hepatitis C viral infection, or cirrhosis.

In some embodiments, the inhibitor of GPER1 is an antagonist of GPER1.

In some embodiments, the inhibitor of GPER1 is G-15 or G-36.

In some embodiments, the inhibitor of GPER1 inhibits the expression of gper1. In some embodiments, the inhibitor of GPER1 is an inhibitory nucleic acid selected from the group consisting of a locked nucleic acid (LNA) molecule, a short hairpin RNA (snRNA) molecule, a small inhibitory RNA (siRNA) molecule, an antisense nucleic acid molecule, a peptide nucleic acid molecule, a morpholino, and a ribozyme. In some embodiments, the inhibitor of GPER1 comprises a RNA-guided nuclease system selected from the group consisting of a zinc finger nuclease system, a transcription activator-like effector nuclease (TALEN) system, a meganuclease system, or a CRISPR/Cas9 system.

In some embodiments, the inhibitor of GPER1 is an anti-GPER1 antibody (e.g., an antagonist antibody).

In another aspect, the invention provides methods of selecting a subject for treatment with an inhibitor of GPER1, the method comprising obtaining a liver tissue sample from the subject; performing an assay to determine whether GPER1-positive hepatocytes are present in the liver tissue sample; identifying a subject as having GPER1-positive hepatocytes; and selecting the identified subject for treatment with an inhibitor of GPER1.

In some embodiments, the subject has been diagnosed with cirrhosis. In some embodiments, the subject has been diagnosed with liver cancer. In some embodiments, the liver cancer comprises hepatocellular carcinoma (HCC), cholangiocarcinoma, fibrolamellar carcinoma, or hepatoblastoma. In some embodiments, the subject has been diagnosed with a hepatitis C viral infection or a hepatitis B viral infection.

In some embodiments, the assay is an immunohistochemical assay.

In some embodiments, the subject is a male subject. In some embodiments, the subject is a female subject.

In some embodiments, the methods further comprise administering therapeutically effective amount of an inhibitor of GPER1 to the subject.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

FIG. 1A depicts brightfield and fluorescent images of male and female Tg(fabp10a:GFP) adult zebrafish exposed to DMSO (0.1%) or E2 (10 μM) daily for six weeks. Scale bars, 2 mm. FIG. 1B shows the dissected liver weights (mg). FIG. 1C depicts a transcriptomic analysis showing E2-induced upregulated genes in male and female livers (fold-change>10), particularly genes involved in cell cycle processes. FIG. 1D depicts a polar metabolomics analysis demonstrating significant sex-dimorphic differences between DMSO and E2-exposed livers (fold-change≥2). FIG. 1E depicts the liver size at 120 hpf as determined by fluorescence microscopy in Tg(fabp10a:GFP) reporter fish, and by ISH for fabp10a. Scale bars, 200 μm. FIG. 1F shows the quantification of fabp10a expression by qRT-PCR in Tg(fabp10a:GFP) larvae at 120 hpf. FIG. 1G shows the quantification of liver volume by lightsheet microscopy. FIG. 1H shows the quantification of the number of $GFP^+$ hepatocytes by FACS. FIG. 1I shows the liver size of larvae exposed to E2, anastrazole (ANAS; 10 μM), and E2+ANAS from 110-115 hpf. Scale bar, 200 μm. FIG. 1J shows the relative liver area (fold from DMSO) as assessed by ISH for fabp10a at 120 hpf. Results represent at least three independent experiments. FIGS. 1C and 1D represent one experiment with at least three biological replicates. Values represent mean±standard error of the mean (SEM), n as indicated, $*p<0.05$, $p<0.01$, $**p<0.0001$, two-tailed Student's t-test.

FIG. 2A are images showing liver size of larvae exposed to selective antagonists for ESR1 (MPP), ESR2 (PHTPP) or GPER1 (G-15) alone and together with E2 from 110-115 hpf. FIG. 2B depicts the liver area (fold from DMSO). $****p<0.0001$, ns=not significant, two-tailed Student's t-test. FIG. 2C are images showing the liver size of WT, gper1 morphants, and human gper1 mRNA injected gper1 morphants. FIG. 2D depicts the relative liver size distribution assessed as large, medium or small liver. $*p<0.05$, $p<0.01$, two-tailed Student's t-test. FIG. 2E shows that $gper1^{-/-}$ mutants in Tg(fabp10a:GFP) background exhibited progressively impaired liver development from 72-120 hpf. FIG. 2F depicts the liver size of $gper1^{+/+}$ and $gper1^{-/-}$ larvae at 72, 96, and 120 hpf, $p<0.0001$, two-tailed Student's t-test. FIG. 2G shows that $gper1^{-/-}$ mutants failed to respond to E2 or G-1. FIG. 2H depicts the liver area (fold from DMSO). $*p<0.001$, two-tailed Student's t-test; $****p<0.0001$, ns=not significant, one-way ANOVA. Results represent at least three independent experiments. Liver area assessed by ISH for fabp10a at 120 hpf. All values represent mean±SEM, n as indicated, scale bars 200 μm.

FIGS. 3A-3H show that E2 signals via GPER1 to promote cell cycle progression, proliferation, and cell size increase in the liver. FIG. 3A depicts the FACS profiles of cell cycle analysis of $GFP^+$ hepatocytes in Tg(fabp10a:GFP) larvae. FIG. 3B shows the relative distribution of $GFP^+$ hepatocytes in G1 (light grey), S (black), or G2/M (dark grey)-phase. * indicates difference in fraction of cells in S and G2/M-phase in DMSO-exposed hepatocytes, $p<0.01$, $*p<0.001$, ns=not significant, two-tailed Student's t-test. FIGS. 3C and 3D show that cell cycle analysis revealed decreased S-phase in $gper1^{-/-}$ mutants at 120hpf. $p<0.01$, two-tailed Student's t-test. FIG. 3E are images of proliferating cell nuclear antigen (PCNA; left) and terminal deoxynucleotidyl transferase dUTP nick-end labeling TUNEL (right) staining of whole larvae section. Liver is outlined. Insets show higher magnification of hepatocytes. Scale bars, 100 μm, scale bar (inset), 30 μm. FIG. 3F shows the percentage (%) of $PCNA^+$ cells from total hepatocytes in the liver area. $*p<0.001$, $**p<0.0001$, two-tailed Student's t-test; $p<0.0001$, one-way ANOVA. FIG. 3G shows liver sections of DMSO or E2-exposed larvae stained with Pan-Cadherin. Scale bars, 25 μm. FIG. 3H depicts the hepatocyte size quantification (fold from DMSO). $**p<0.0001$, two-tailed Student's t-test. Results represent three independent experiments. Values represent mean±SEM, n as indicated.

FIG. 4A are images showing the liver size of $gper1^{+/+}$ and $gper1^{-/-}$ larvae. E2-induced liver size increase was blocked by E2+MK-2206 co-exposure (top row arrowheads). Smaller liver in $gper1^{-/-}$ mutant was normalized by 740Y-P exposure (bottom row arrowheads). FIG. 4B depicts the liver area (fold from DMSO). $*p<0.05$, $**p<0.0001$, ns=not significant, two-tailed Student's t-test. FIG. 4C shows the immunoblot analysis of $gper1^{+/+}$ and $gper1^{-/-}$ whole larvae after chemical exposures. FIG. 4D are images showing that E2 or G-1 exposure increased liver size in $gper1^{+/+}$, $mtor^{+/-}$, but not in $gper1^{-/-}$, $mtor^{-/-}$, or $gper1^{-/-}$; $mtor^{-/-}$ larvae (arrowheads). FIG. 4E depicts the liver area (fold from DMSO). $p<0.01$, $****p<0.0001$, ns=not significant, one-way ANOVA. FIG. 4F shows the immunoblot analysis of $gper1^{+/+}$, $gper1^{-/-}$, $mtor^{+/-}$, and $mtor^{-/-}$ whole larvae. Results represent at least three independent experiments. Representative blots of at least four independent experiments. All $^\dagger$ indicates difference from DMSO-exposed liver, $^\dagger p<0.05$, $^{\dagger\dagger}p<0.01$, $^{\dagger\dagger\dagger}p<0.001$, $^{\dagger\dagger\dagger\dagger}p<0.0001$, ns=not significant, two-tailed Student's t-test. Liver area was assessed by ISH for fabp10a at 120hpf. All values indicate mean±SEM, n as indicated, all scale bars, 200 μm.

FIG. 5A depicts a scheme for Mtz exposure and liver regeneration analysis. FIG. 5B shows $gper1^{+/+}$, $gper1^{-/-}$, $mtor^{+/-}$, and $mtor^{-/-}$ larvae in Tg(fabp10a:CFP-NTR) background at 150 hpf. FIG. 5C depicts liver area (fold from—Mtz-treated WT) as determined by CFP expression. $*p<0.05$, $***p<0.001$, ns=not significant, one-way ANOVA. All $^\dagger$ indicates significant difference from Mtz-treated WT livers at 30 hpT, $^{\dagger\dagger}p<0.01$, $^{\dagger\dagger\dagger\dagger}p<0.0001$, two-tailed Student's t-test. FIG. 5D are images showing the whole-mount p-S6 immunostaining revealed mTORC1 activation in regenerating WT livers but not in $gper1^{-/-}$ or $mtor^{-/-}$ livers (liver outlined). Results represent three independent experiments. All values represent mean±SEM, n as indicated, all scale bars, 200 μm.

FIGS. 6A-6F show that E2 signaling via GPER1 promotes sex dimorphism in adult liver growth. FIG. 6A $gper1^{+/+}$ and $gper1^{-/-}$ adults treated with DMSO or E2.

Scale bars, 2 mm. FIG. 6B depicts the liver weight (mg). **p<0.0001, ns=not significant, two-tailed Student's t-test. FIG. 6C depicts the sex-specific gper1 liver expression (fold from elf1α). **p<0.0001, two-tailed Student's t-test. FIG. 6D shows an immunoblot analysis for p-Akt, GPER1, and β-actin levels in gper1$^{+/+}$ and gper1$^{-/-}$ male livers. FIG. 6E are images of the immunofluorescent staining of DMSO or E2-exposed male donor-derived hepatocytes with EdU and HNF4α. White arrowheads indicate EdU and HNF4α double-positive cells. Scale bar, 100 μm. FIG. 6F shows the percentage (%) of EdU$^+$ hepatocytes. * indicates significant difference from DMSO controls. *p<0.05, **p<0.01, two-tailed Student's t-test. Results represent at least three independent experiments. Values represent mean±SEM, n as indicated.

FIGS. 7A-7H show that the activation of E2 signaling promotes liver cancer initiation and progression via GPER1. FIG. 7A are microscopy images of a human non-cirrhotic liver, cirrhotic liver, and HCC sections immunostained for GPER1. Scale bar, 100 μm. All values represent mean±SEM, n as indicated. FIG. 7B depicts the liver cancer incidence in DMBA-exposed adults at 7 months post fertilization (mpf) was reduced by 50% in gper1$^{-/-}$ mutants compared to WT. p<0.05, one-tailed Chi-Square test. FIG. 7C depicts the number of liver tumors per fish. *p<0.05, one-tailed Mann-Whitney test. FIG. 7D depicts the tumor size (mm) per fish. p<0.01, two-tailed Student's t-test. FIG. 7E is a scheme illustrating DMBA carcinogenesis followed by chemical prevention trial. FIG. 7F is a Kaplan-Meier survival plot. n=52, 66, 39 for DMSO, E2, and E2+G-15 treated adults at 249 days post first treatment, p<0.0001, Log-rank (Mantel-Cox) test. FIG. 7G depicts the liver tumor size (mm) per fish at 9 mpf. *p<0.001, ns=not significant, one-way ANOVA. FIG. 7H are images of Tg(fabp10a:GFP) fish after chemical treatments and corresponding liver histology. NT=non-tumor, scale bars (whole animal), 2 mm, scale bar (histology section), 100 μm.

FIG. 8A is a Venn diagram showing intersection of genes differentially expressed in the livers of male vs male+E2, female vs female+E2, and female vs male. (fold change>10). Values demonstrate number of genes upregulated by E2 in male liver (299 genes), female liver (125 genes) or female-associated liver genes (75 genes). FIG. 8B depicts a transcriptomic analysis showing E2-induced upregulated genes in female-only livers (fold change>10 from DMSO). Gene ontology analysis revealed upregulation of genes involved in convergent extension. FIG. 8C depicts a polar metabolomics analysis demonstrating significant sex dimorphic differences between DMSO and E2-exposed female only livers (fold change≥2 from DMSO). Metabolic pathway analysis indicated regulation of ammonia and glutamate metabolism.

FIG. 9A shows representative images of WT larvae with increased liver size upon E2 or G-1 treatments, decreased liver size upon G-15 treatment, and normalized liver size upon E2 and G-15 co-treatment as assayed by ISH for fabp10a at 120 hpf. Scale bar, 200 μm. FIG. 9B depicts the quantification of GFP$^+$ hepatocytes in fabp10a:GFP larvae by FACS (fold from DMSO). n=3 independent experiments of 30 pooled larvae, mean±SEM, *p<0.001, p<0.0001, two-tailed Student's t-test; p<0.0001, one-way ANOVA. FIG. 9C depicts the quantification of liver area as determined by ISH for fabp10a (fold from DMSO). n as indicated, mean±SEM, p<0.01, ****p<0.0001, ns=not significant, two-tailed Student's t-test. FIG. 9D shows representative images of liver size as assessed by ISH for fabp10a at 120 hpf demonstrating increased liver size upon E2 exposure that can be blocked by knockdown of gper1 but not esr(s). Scale bar, 200 μm. FIG. 9E shows representative images of transgenic estrogen response element (5×ERE:GFP) reporter fish exposed to DMSO, 5 hrs. of E2, 24 hrs. of E2 at 120 hpf. Scale bar, 200 μm. FIG. 9F depicts the distribution of the percentage (%) of 5×ERE:GFP fish with high, low, or no GFP expression upon E2 exposures was plotted. n=50, 47, 24 for number of larvae exposed to DMSO, 5 hrs. (110-115 hpf) of E2, and 24 hrs. (96-120 hpf) of E2 respectively.

FIG. 10A shows images of the lateral and dorsal views of gper1 expression in larvae at 72, 96, 120 hpf after ISH for gper1. gper1 is expressed in the liver (arrowhead) starting at 96 hpf. Scale bars, 200 μm. FIG. 10B shows the expression of gper1 transcripts in whole embryo at 24, 48, 72, 96, 109 and 120 hpf as measured by RT-PCR compared to elf1α housekeeping gene control. FIG. 10C depicts the expression of gper1 transcripts in whole embryo at 12, 35, 48, 72, and 120 hpf as measured by quantitative RT-PCR (fold from gper1 expression at 12 hpf). FIG. 10D depicts the genomic organization of zebrafish gper1. Black boxes represent exons with ATG site indicated by the arrow. Sequence alignment of gper1$^{+/+}$ siblings (SEQ ID NO: 1) and gper1$^{-/-}$ mutant (SEQ ID NO: 2) showing TALEN-generated 29 base pair deletion leading to premature stop codon (*). FIG. 10E shows an immunoblot analysis of GPER1 (arrow) and β-actin levels showing loss of GPER1 in gper1$^{+/+}$ mutants compared to gper1$^{+/+}$ siblings. FIG. 10F shows representative images of gper1$^{-/-}$ and gper1$^{+/+}$ larvae ISH for foxA3 (endoderm) and prox1 (hepatic progenitor) at 48 hpf, prox1 and fabp10a (hepatocyte) at 72 hpf, fabp10a and deltaC (biliary tree) at 120 hpf. Decreased expression of fabp10a and deltaC in gper1$^{-/-}$ compared to gper1$^{+/+}$ was observed only at 120 hpf. Scale bars, 200 μm. FIG. 10G depicts the quantification of marker expression area in gper1$^{-/-}$ and gper1$^{+/+}$ larvae as assessed by ISH (fold from gper1$^{+/+}$). n as indicated, mean±SEM, p<0.01, **p<0.0001, ns=not significant, two-tailed Student's t-test.

FIG. 11A shows images of whole larvae exposed to DMSO or E2 at 120 hpf for BrdU analysis. Larvae were pulsed with BrdU and stained for BrdU after fixation. FIG. 11B shows that larvae treated with E2 had higher number of BrdU positive cells per fixed liver area compared to DMSO-exposed controls. Scale bar, 400 μm, scale bar (inset), 100 μm, n as indicated, mean±SEM, ***p<0.001, two-tailed Mann-Whitney test.

FIG. 12A shows the liver size of WT larvae after chemical exposures as assessed by ISH for fabp10a at 120 hpf. E2 exposure increased liver size (27% or 21/78, 21 larvae with phenotype out of 78 total larvae observed) while PI3K inhibitor LY292002 decreased liver size (72% or 55/76). Co-treatment of E2 and LY292002 blocked estrogenic effect on liver size (86% or 59/69). FIG. 12B shows the liver size of WT and gper1MO knockdown larvae after chemical exposures at 120 hpf as assayed by ISH for fabp10a. gper1 morphants had decreased liver size (60% or 15/26). Treatment of larvae with the PI3K-activator 740Y-P increased liver size (77% or 24/31) and rescued small liver phenotype in gper1 morphants (61% or 11/18). FIG. 12C shows the liver size of gper1$^{+/+}$ and gper1$^{-/-}$ larvae ISH for fabp10a at 120 hpf after chemical exposures. E2 or G-1-exposed gper1$^{+/+}$ larvae had increased liver size (arrowhead) that can be blocked by co-exposure of E2+Rapamycin or G-1+Rapamycin. gper1$^{-/-}$ blocked E2 and G-1 effects on liver size. FIG. 12D depicts the liver area of gper1$^{+/+}$ and gper1$^{-/-}$ larvae ISH for fabp10a at 120 hpf after chemical exposures (fold from DMSO). n as indicated, mean±SEM, ****p<0.0001, ns=not significant, two-tailed Student's t-test. ns=not significant, one-way ANOVA. † indicates significant difference from DMSO-treated WT controls. ††p<0.01, ††††p<0.0001, two-tailed Student's t-test. FIG. 12E depicts the liver size distribution of WT larvae and mtor morphants as assessed by ISH for fabp10a at 120 hpf upon exposure to DMSO or E2 as % of larvae with large, medium or small livers. FIG. 12F shows the liver size of WT and mtor morphants as determined by ISH for lfabp10a at 120 hpf. FIG. 12G shows the whole mount WT larvae at 120 hpf immunostained for p-Akt and p-S6 upon DMSO or E2 exposure. Liver is outlined. All scale bars, 200 μm.

FIG. 14A shows representative images of GPER1 staining scoring system: 0=minimal or no staining; 1+=faint/mild staining; 2+=moderate/strong staining. Scale bar, 50 μm. FIG. 14B shows the quantification of GPER1 staining scores of non-cirrhotic livers, cirrhotic livers, adjacent non-tumor (ANT) tissues, which are mostly cirrhotic, and HCC tissues. n as indicated, mean±SEM, *p<0.05, ns=not significant, two-tailed Mann-Whitney test. FIG. 14C depicts the quantification of GPER1 staining scores in non-cirrhotic male and female livers. n as indicated, mean±SEM. FIG. 14D are immunoblots showing the signaling responses in HepG2 cells to E2 and/or G-15 exposure. FIG. 14E depicts the quantification of liver tumor size (mm) per fish in DMBA-exposed WT fish followed by DMSO, E2 or E2+G-15 exposure up until 9 mpf. n as indicated, mean±SEM, *p<0.05, **P<0.01, two-tailed Student's t-test. FIG. 14F are microscopy images showing the histological features of adult zebrafish liver stained with hematoxylin and eosin (H&E). Left column shows zoomed images from normal male liver (a), normal female liver (b), and livers with hepatocellular adenoma (HCA) (c), hepatocellular carcinoma (HCC) (d), and cholangiocarcinoma (CC) (e). Scale bar, 25 μm. Right column shows low magnification images of normal male liver (f), normal female liver (g), and livers with large tumor (h), small tumor (i) and multi-foci tumor (j). Scale bars (f)-(i), 100 μm, scale bar (j), 250 μm.

DETAILED DESCRIPTION

Figure 1A:
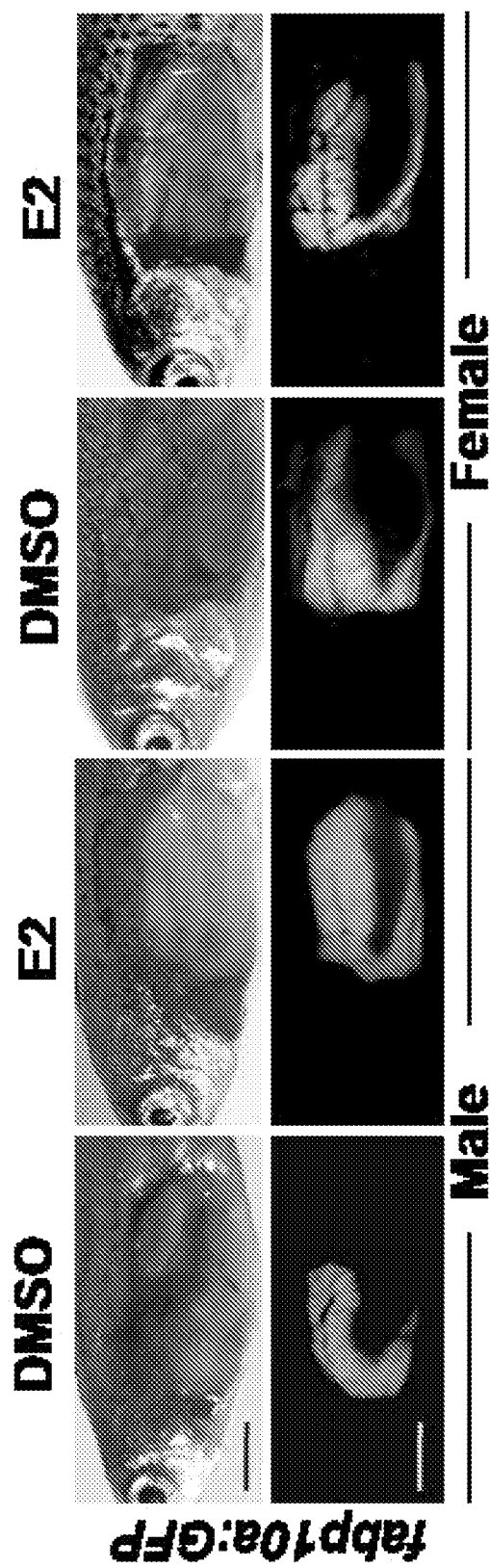
FIGS. 1A-1J show that E2 increases liver size.

Hepatocellular carcinoma (HCC) is the second most common cause of cancer mortality worldwide, and the fastest-growing cause of cancer deaths in the U.S.[1] Clinically relevant biomarkers and therapies to detect and prevent HCC do not exist. Interestingly, chronic liver disease and liver cancer are much more frequent in males,[2] and men with cirrhosis and HCC exhibit elevated serum estrogen levels.[3,4] Further, patients undergoing surgical liver resection exhibit elevated serum estrogen levels, suggesting the importance of estrogenic regulation during liver regeneration.[5] Despite these observations, the mechanisms by which the liver senses and responds to estrogen to impact liver growth and cancer formation remain undetermined.

17β-estradiol (E2) is the most abundant and biologically active form of estrogen. Canonical estrogen signaling is mediated through nuclear hormone estrogen receptors 1 (ESR1/ERα) and 2 (ESR2/ERβ), resulting in direct transcriptional target gene activation. In addition, E2 can exert non-canonical activity through the G protein-coupled estrogen receptor 1 (GPER1). While roles of ESR1 and ESR2 have been widely studied in the context of reproductive biology and cancer,[6] the functional consequences of GPER1 signaling are less well understood. Originally discovered in breast cancer cells,[7] GPER1 has been shown to regulate proliferation and relaxation of vascular smooth muscle.[8] Several secondary messenger signals have been identified to act downstream in different cellular contexts, including Erk,[7] PI3K,[9] and $Ca^{2+}$ release.[10] Recently, GPER1 expressed in the gallbladder was found to contribute to gallstone formation.[11] GPER1 expression in hepatocytes, and its potential role in the control of hepatocyte proliferation and organ growth during development as well as in the setting of liver regeneration or cancer progression have not been previously characterized.

The studies described herein describe the identification and characterization of E2 and GPER1 in the regulation of liver growth (including abnormal growth (e.g., liver cancer). Applicants have discovered that E2 induces cell cycle progression and increases hepatocyte proliferation via GPER1 and downstream activation of PI3K/mTOR signaling. Applicants have surprisingly discovered that inhibition of GPER1 diminishes E2-induced tumor progression. Therefore, GPER1 is a therapeutic target that may be used for the prevention and treatment of abnormal growth conditions in the liver tissue of a subject, including liver cancer.

Moreover, Applicants have discovered that GPER1 is expressed in hepatocytes from subjects having risk factors for HCC, such as cirrhosis. This discovery is particularly advantageous since GPER1 can be used as a biomarker to identify subjects having risk factors for HCC that will develop an abnormal liver growth (e.g., HCC). The identified subjects can be administered an inhibitor of GPER1 in order to prevent the development of the abnormal liver growth.

Methods of Treatment and Prevention

In one aspect, the present disclosure provides methods of treating a subject having liver cancer (e.g., HCC), or at risk of developing liver cancer comprising administering a therapeutically effective amount of an inhibitor of G protein-coupled estrogen receptor 1 (GPER1). A diagnosis of liver cancer can be made, e.g., using methods known in the art, e.g., based on morphologic, immunophenotypic, serological markers, and genetic features. For example, the diagnosis of HCC is namely based on imaging studies (see, e.g., Dimitroulis et al. *World J. Gastroenterol.* 23(29): 5282-94, incorporated herein by reference). Subjects that have been identified as having liver cancer (HCC) can be treated as described herein as monotherapy or in combination with a treatment method known in the art.

In another aspect, the present disclosure provides methods of preventing the development of an abnormal growth condition in a liver tissue of a subject, the method comprising administering an inhibitor of GPER1. Abnormal liver growths, such as liver cancers, are associated with multiple risk factors, including, but not limited to, chronic liver injury, steatohepatitis, alcoholic liver disease, aflatoxin exposure, hemochromatosis, chronic viral infection with hepatitis B virus (HBV) or hepatitis C virus (HCV), cirrhosis due to HBV or HCV, and cirrhosis of any etiology. Subjects (e.g., human subjects) having one or more of these risk factors are suitable for treatment with an inhibitor of GPER1, as described herein, in order to prevent the development of an abnormal growth condition (e.g., liver cancer).

In some embodiments, the liver cancer is selected from the group consisting of hepatocellular carcinoma (HCC), cholangiocarcinoma, fibrolamellar carcinoma, or hepatoblastoma.

Suitable subjects include, but are not limited to mammalian subjects including domestic animals (e.g., dogs and cats), fish (e.g., zebrafish), agricultural animals (e.g., cows and bison), laboratory animals (e.g., rabbits, mice, hamsters, gerbils, and rats), non-human primates, and humans. In some embodiments, the subject is a female subject. In some embodiments the subject is a male subject.

Methods of Selecting Subjects for Treatment with GPER1 Inhibitors

In another aspect, the present disclosure provides methods of identifying subjects that are suitable for the treatment with an inhibitor of GPER1 as described herein. As discussed in detail below, Applicants have discovered that some subjects having particular etiological factors associated with the development of abnormal growth conditions in a liver tissue (e.g., liver cancer) comprise hepatocytes expressing GPER1 which may mediate E2-dependent cell cycle progression and increased hepatocyte proliferation which may ultimately result in abnormal tissue growth. Thus, the identification of subjects having GPER1 positive hepatocytes may be used as a biomarker to select for subjects at increased risk for abnormal tissue growth (e.g., cancer), and/or to identify subjects susceptible to treatment with an inhibitor of GPER1, using the methods described herein.

Thus, in some embodiments, provided herein are methods of selecting a subject for treatment with an inhibitor of GPER1, the method comprising obtaining a liver tissue sample from the subject; performing an assay to determine whether GPER1-positive hepatocytes are present in the liver tissue sample; identifying a subject as having GPER1-positive hepatocytes; and selecting the identified subject for treatment with an inhibitor of GPER1.

In some embodiments, the subject has one or more risk factors associated with the development of liver cancer (e.g., HCC). For example, in some embodiments, the subject has been diagnosed with cirrhosis (e.g., hepatitis-induced cirrhosis, or alcohol liver cirrhosis). In some embodiments, the subject has been diagnosed with fatty liver disease.

In some embodiments, the subject has been diagnosed with an HCV infection (e.g., a chronic HCV infection). In some embodiments, the subject has been diagnosed with an HCV infection (e.g., a chronic HBV infection). In some embodiments, the subject has been diagnosed with liver cancer (e.g., hepatocellular carcinoma (HCC), cholangiocarcinoma, fibrolamellar carcinoma, and hepatoblastoma). In some embodiments, the subject has not been diagnosed with liver cancer. In some embodiments, the subject does not have a risk factor associated with the development of liver cancer.

Assays that may be used to determine whether a liver tissue from a subject comprises GPER1-positive cells (e.g., hepatocytes) are known in the art, and include immunohistochemical assessments of the tissue, quantitative imaging (e.g., flow cytometry), or other techniques capable of reliably indicating the presence and degree of GPER1 expression. In some embodiments, the assay is performed in vivo. In some embodiments, the assay is performed ex vivo. In some embodiments, the assay is performed in vitro. In some embodiments, the tissue is obtained from the subject via a biopsy. In some embodiments, the tissue is obtained from the subject following a surgical intervention (e.g., a liver transplantation). Immunohistochemical analysis of tissue biopsies or surgical specimens may be preferred for this purpose. Methods for immunohistochemical analysis of tissues are well known in the art. An example of an immunohistochemical analytical technique useful for determining the level of GPER1 in a sample is described in the example sections below.

G Protein-Coupled Receptor 1 (GPER1)

G protein-coupled estrogen receptor 1 (also known as G protein-coupled receptor 30) is a seven transmembrane-domain G protein-coupled receptor (GPCR) that binds 17β-estradiol (E2) with high affinity and mediate estrogenic signals (Revankar et al. (2005) *Science* 307: 1625-30; Thomas et al. (2005) *Endocrinology* 146: 624-32). GPER1 is activated in cells treated with 17β-estradiol (E2) and mediates rapid cell signaling events (Prossnitz (2008) *Annual Rev. Physiol.* 70: 165-90; Prossnitz and Maggiolini (2009) *Mol. Cell. Endocrinol.* 308: 32-8; and Tang et al. (2014) *Mol. Cell. Endocrinol.* 389: 92-8). GPER-1 is also activated by the agonist G-1, the antiestrogen fulvestrant, and 4-OHT (Maggiolini et al. (2004) *J. Biol. Chem.* 279: 27008-16; Revankar et al. (2005); Thomas and Dong (2006) *J. Steroid Biochem. Mol. Biol.* 102: 175-9; Thomas et al. (2005) *Endocrinology* 146: 624-32; Vivacqua (2006) *Mol. Pharmacol.* 70: 1414-23). In breast cancer cells, GPER1 activation can induce apoptosis and inhibit proliferation via p53-mediated cell cycle arrest (Wei et al. (2014) *Cell Death Dis.* 5(10): e1428). GPER1 activation can also induce epidermal growth factor receptor (EGFR)-dependent cell proliferation (see e.g., Maggiolini et al. (2004) *J. Biol. Chem.* 279(26): 27008-16; and Pupo et al. (2012) *Environ. Health Perspect.* 120(8): 1177-82). GPER1 has been found to be expressed in various cancers, including lung, prostate, endometrial, thyroid, brease, and ovarian, and thyroid cancers (see, e.g., Liu et al. (2015) *Med Oncol.* 32: 104; Vivacqua et al. (2006) *Mol Endocrinol.* 20: 631-46; Albanito et al. (2007) *Cancer Res.* 67: 1859-66; Tang et al. (2014) *Int. J. Clin. Exp. Pathol.* 7: 3213-23; and Lappano et al. (2014) *Front Endocrinol.* (Lausanne) 5: 66).

GPER1 Sequences

Although several transcript variants encoding different isoforms of GPER1 have been found for the gper1 gene, the full length protein sequence for human GPER1 (*NCBI Reference Sequence* No. NP_001496.1) is provided below:

```
>NP_001496.1 G-protein coupled estrogen receptor 1
[Homo sapiens]
                                           (SEQ ID NO: 3)
MDVTSQARGVGLEMYPGTAQPAAPNTTSPELNLSHPLLGTALANGTGELS

EHQQYVIGLFLSCLYTIFLFPIGFVGNILILVVNISFREKMTIPDLYFIN

LAVADLILVADSLIEVFNLHERYYDIAVLCTFMSLFLQVNMYSSVFFLTW

MSFDRYIALARAMRCSLFRTKHHARLSCGLIWMASVSATLVPFTAVHLQH

TDEACFCFADVREVQWLEVTLGFIVPFAIIGLCYSLIVRVLVRAHRHRGL

RPRRQKALRMILAVVLVFFVCWLPENVFISVHLLQRTQPGAAPCKQSFRH

AHPLTGHIVNLAAFSNSCLNPLIYSFLGETFRDKLRLYIEQKTNLPALNR

FCHAALKAVIPDSTEQSDVRFSSAV
```

An exemplary human cDNA nucleic acid sequence encoding the GPER1 amino acid sequence above is provided below:

(SEQ ID NO: 4)
```
atggatgtgacttcccaagcccggggcgtgggcctggagatgtacccagg caccgcgcagcctgcggcccccaacaccacctcccccgagctcaacctgt cccaccgctcctgggcaccgccctggccaatgggacaggtgagctctcg gagcaccagcagtacgtgatcggcctgttcctctcgtgcctctacaccat cttcctcttccccatcggctttgtgggcaacatcctgatcctggtggtga acatcagcttccgcgagaagatgaccatcccgacctgtacttcatcaac ctggcggtggcggacctcatcctggtggccgactccctcattgaggtgtt caacctgcacgagcggtactacgacatcgccgtcctgtgcaccttcatgt cgctcttcctgcaggtcaacatgtacagcagcgtcttcttcctcacctgg atgagcttcgaccgctacatcgccctggccagggccatgcgctgcagcct gttccgcaccaagcaccacgcccggctgagctgtggcctcatctggatgg catccgtgtcagccacgctggtgcccttcaccgccgtgcacctgcagcac accgacgaggcctgcttctgtttcgcggatgtccgggaggtgcagtggct cgaggtcacgctgggcttcatcgtgcccttcgccatcatcggcctgtgct actccctcattgtccgggtgctggtcagggcgcaccggcaccgtgggctg cggcccggcggcagaaggcgctccgcatgatcctcgcggtggtgctggt cttcttcgtctgctggctgccggagaacgtcttcatcagcgtgcacctcc tgcagcggacgcagcctggggccgctccctgcaagcagtctttccgccat gcccaccccctcacgggccacattgtcaacctcgccgccttctccaacag ctgcctaaacccctcatctacagctttctcggggagaccttcagggaca agctgaggctgtacattgagcagaaaacaaatttgccggccctgaaccgc ttctgtcacgctgccctgaaggccgtcattccagacagcaccgagcagtc ggatgtgaggttcagcagtgccgtgtag
```

Inhibitors of GPER1

In some embodiments, the methods described herein include administering one or more inhibitors of GPER1 or any pharmaceutically acceptable salt thereof, alone or in combination with a conventional treatment as described herein, or known in the art; useful inhibitors of GPER1 include small molecules, anti-GPER1 antibodies, and inhibitory nucleic acids that reduce and/or inhibit the expression of GPER1. Several small molecule inhibitors of GPER1 are known in the art and include the GPER1 antagonist G-15 ((3aS,4R,9bR)-4-(6-Bromo-1,3-benzodioxol-5-yl)-3a,4,5,9b-3H-cyclopenta[c]quinoline; CAS No. 1161002-05-6; see Dennis et al. (2009) *Nature Chemical Biology* 5(6): 421-427 (2009); and Dennis et al. (2011) *J. Steroid Biochem. Mol. Biol.* 127(3-5): 358-66); and the GPER1 antagonist G-36 ((±)-(3aR,4S*,9bS*)-4-(6-Bromo-1,3-benzodioxol-5-yl)-3a,4,5,9b-tetrahydro-8-(1-methylethyl)-3H-cyclopenta[c]quinoline); CAS No. 1392487-51-2; see Dennis et al. (2011)).

Inhibitory Nucleic Acids

Inhibitory nucleic acids useful in the present methods and compositions include antisense oligonucleotides, ribozymes, external guide sequence (EGS) oligonucleotides, siRNA compounds, single- or double-stranded RNA interference (RNAi) compounds such as siRNA compounds, molecules comprising modified bases, locked nucleic acid molecules (LNA molecules), antagomirs, peptide nucleic acid molecules (PNA molecules), and other oligomeric compounds or oligonucleotide mimetics which hybridize to at least a portion of the target nucleic acid and modulate its function. In some embodiments, the inhibitory nucleic acids include antisense RNA, antisense DNA, chimeric antisense oligonucleotides, antisense oligonucleotides comprising modified linkages, interference RNA (RNAi), short interfering RNA (siRNA); a micro, interfering RNA (miRNA); a small, temporal RNA (stRNA); or a short, hairpin RNA (snRNA); small RNA-induced gene activation (RNAa); small activating RNAs (saRNAs), or combinations thereof. See, e.g., International Publication No. WO 2010/040112.

In the present methods, the inhibitory nucleic acids are preferably designed to target a nucleic acid encoding GPER1 (e.g., a mRNA encoding GPER1, or a gper1 gene).

In some embodiments, the inhibitory nucleic acids are 10 to 50, 13 to 50, or 13 to 30 nucleotides in length. One of ordinary skill in the art will appreciate that this embodies oligonucleotides having antisense (complementary) portions of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides in length, or any range therewithin. It is understood that non-complementary bases may be included in such inhibitory nucleic acids; for example, an inhibitory nucleic acid 30 nucleotides in length may have a portion of 15 bases that is complementary to the targeted RNA. In some embodiments, the oligonucleotides are 15 nucleotides in length. In some embodiments, the antisense or oligonucleotide compounds of the invention are 12 or 13 to 30 nucleotides in length. One of ordinary skill in the art will appreciate that this embodies inhibitory nucleic acids having antisense (complementary) portions of 12, 13, 14, 15, 16, 17, 18, 19, 20, 21, 22, 23, 24, 25, 26, 27, 28, 29, or 30 nucleotides in length, or any range therewithin.

Preferably, the inhibitory nucleic acid comprises one or more modifications comprising: a modified sugar moiety, and/or a modified internucleoside linkage, and/or a modified nucleotide and/or combinations thereof. It is not necessary for all positions in a given oligonucleotide to be uniformly modified, and in fact more than one of the modifications described herein may be incorporated in a single oligonucleotide or even at within a single nucleoside within an oligonucleotide.

In some embodiments, the inhibitory nucleic acids are chimeric oligonucleotides that contain two or more chemically distinct regions, each made up of at least one nucleotide. These oligonucleotides typically contain at least one region of modified nucleotides that confers one or more beneficial properties (such as, for example, increased nuclease resistance, increased uptake into cells, increased binding affinity for the target) and a region that is a substrate for enzymes capable of cleaving RNA:DNA or RNA:RNA hybrids. Chimeric inhibitory nucleic acids may be formed as composite structures of two or more oligonucleotides, modified oligonucleotides, oligonucleosides, and/or oligonucleotide mimetics as described above. Such compounds have also been referred to in the art as hybrids or gapmers. Representative U.S. patents that teach the preparation of such hybrid structures comprise, but are not limited to, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; and 5,700,922, each of which is herein incorporated by reference.

In some embodiments, the inhibitory nucleic acid comprises at least one nucleotide modified at the 2' position of the sugar, most preferably a 2'-O-alkyl, 2'-O-alkyl-O-alkyl or 2'-fluoro-modified nucleotide. In other preferred embodiments, RNA modifications include 2'-fluoro, 2'-amino and 2' O-methyl modifications on the ribose of pyrimidines, abasic residues or an inverted base at the 3' end of the RNA. Such modifications are routinely incorporated into oligonucleotides and these oligonucleotides have been shown to have a higher Tm (i.e., higher target binding affinity) than; 2'-deoxyoligonucleotides against a given target.

A number of nucleotide and nucleoside modifications have been shown to make the oligonucleotide into which they are incorporated more resistant to nuclease digestion than the native oligodeoxynucleotide; these modified oligos survive intact for a longer time than unmodified oligonucleotides. Specific examples of modified oligonucleotides include those comprising modified backbones, for example, phosphorothioates, phosphotriesters, methyl phosphonates, short chain alkyl or cycloalkyl intersugar linkages or short chain heteroatomic or heterocyclic intersugar linkages. Most preferred are oligonucleotides with phosphorothioate backbones and those with heteroatom backbones, particularly $CH_2$—NH—O—$CH_2$, CH, ~N($CH_3$)~O~$CH_2$ (known as a methylene(methylimino) or MMI backbone, $CH_2$—O—N ($CH_3$)—$CH_2$, $CH_2$—N($CH_3$)—N ($CH_3$)—$CH_2$ and O—N ($CH_3$)—$CH_2$—$CH_2$ backbones, wherein the native phosphodiester backbone is represented as O—P—O—CH); amide backbones (see De Mesmaeker et al. (1995) *Ace. Chem. Res.* 28: 366-74); morpholino backbone structures (see U.S. Pat. No. 5,034,506); peptide nucleic acid (PNA) backbone (wherein the phosphodiester backbone of the oligonucleotide is replaced with a polyamide backbone, the nucleotides being bound directly or indirectly to the aza nitrogen atoms of the polyamide backbone, see Nielsen et al. (1991) *Science* 254, 1497-500). Phosphorus-containing linkages include, but are not limited to, phosphorothioates, chiral phosphorothioates, phosphorodithioates, phosphotriesters, aminoalkylphosphotriesters, methyl and other alkyl phosphonates comprising 3'alkylene phosphonates and chiral phosphonates, phosphinates, phosphoramidates comprising 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2' (see U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455, 233; 5,466,677; 5,476,925; 5,519,126; 5,536,821; 5,541,306; 5,550,111; 5,563, 253; 5,571,799; 5,587,361; and 5,625,050; the disclosures of which are incorporated herein by reference in their entireties).

Morpholino-based oligomeric compounds are described in Dwaine et al. (2002) *Biochemistry* 41(14): 4503-10; Genesis 30(3), 2001; Heasman (2002) *Dev. Biol.* 243: 209-14; Nasevicius et al. (2000) *Nat. Genet.* 26: 216-20; Lacerra et al. (2000) *Proc. Natl. Acad. Sci. U.S.A.* 97: 9591-6; and U.S. Pat. No. 5,034,506. In some embodiments, the morpholino-based oligomeric compound is a phosphorodiamidate morpholino oligomer (PMO) (e.g., as described in Iverson (2001) *Curr. Opin. Mol. Ther.* 3: 235-8; and Wang et al. (2010) *J. Gene Med.* 12: 354-64; the disclosures of which are incorporated herein by reference in their entireties).

Cyclohexenyl nucleic acid oligonucleotide mimetics are described in Wang et al. (2000) *J. Am. Chem. Soc.* 122: 8595-602, the contents of which are incorporated herein by reference Modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These comprise those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S, and CH2 component parts; see U.S. Pat. Nos. 5,034,506; 5,166,315; 5,185, 444; 5,214,134; 5,216,141; 5,235,033; 5,264,562; 5,264, 564; 5,405,938; 5,434,257; 5,466,677; 5,470,967; 5,489, 677; 5,541,307; 5,561,225; 5,596,086; 5,602,240; 5,610, 289; 5,602,240; 5,608,046; 5,610,289; 5,618,704; 5,623, 070; 5,663,312; 5,633,360; 5,677,437; and 5,677,439, each of which is herein incorporated by reference.

Modified oligonucleotides are also known that include oligonucleotides that are based on or constructed from arabinonucleotide or modified arabinonucleotide residues. Arabinonucleosides are stereoisomers of ribonucleosides, differing only in the configuration at the 2'-position of the sugar ring. In some embodiments, a 2'-arabino modification is 2'-F arabino. In some embodiments, the modified oligonucleotide is 2'-fluoro-D-arabinonucleic acid (FANA) (as described in, e.g., Lon et al. (2002) *Biochem.* 41: 3457-67; and Min et al. (2002) *Bioorg. Med. Chem. Lett.* 12: 2651-4; the disclosures of which are incorporated herein by reference in their entireties). Similar modifications can also be made at other positions on the sugar, particularly the 3' position of the sugar on a 3' terminal nucleoside or in 2'-5' linked oligonucleotides and the 5' position of 5' terminal nucleotide.

International Publication No. WO 99/67378 discloses arabinonucleic acids (ANA) oligomers and their analogues for improved sequence specific inhibition of gene expression via association to complementary messenger RNA.

Other preferred modifications include ethylene-bridged nucleic acids (ENAs) (e.g., International Publication No. WO 2005/042777, Morita et al. (2001) *Nucleic Acid Res.* Suppl 1: 241-2; Surono et al. (2004) *Hum. Gene Ther.* 15: 749-57; Koizumi (2006) *Curr. Opin. Mol. Ther.* 8: 144-9; and Horie et al. (2005) *Nucleic Acids Symp. Ser. (Oxf)*, 49: 171-2; the disclosures of which are incorporated herein by reference in their entireties). Preferred ENAs include, but are not limited to, 2'-O,4'-C-ethylene-bridged nucleic acids.

Examples of LNAs are described in International Publication No. WO 2008/043753 and include compounds of the following formula.

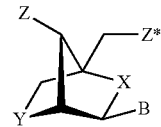

where X and Y are independently selected among the groups —O—, —S—, —N(H)—, N(R)—, —CH2- or —CH— (if part of a double bond), —CH$_2$—O—, —CH$_2$—S—, —CH$_2$—N(H)—, —CH$_2$—N(R)—, —CH$_2$—CH$_2$— or —CH$_2$—CH— (if part of a double bond), —CH=CH—, where R is selected from hydrogen and C$_{1-4}$-alkyl; Z and Z* are independently selected among an internucleoside linkage, a terminal group or a protecting group; B constitutes a natural or non-natural nucleotide base moiety; and the asymmetric groups may be found in either orientation.

Preferably, the LNA used in the oligomer of the invention comprises at least one LNA unit according any of the formulas

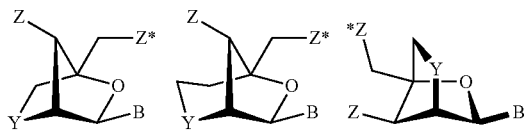

wherein Y is —O—, —S—, —NH—, or N(R$^H$); Z and Z* are independently selected among an internucleoside linkage, a terminal group or a protecting group; B constitutes a natural or non-natural nucleotide base moiety, and RH is selected from hydrogen and C$_{1-4}$-alkyl.

Preferably, the LNA used in the oligomeric compound, such as an antisense oligonucleotide, of the invention comprises at least one nucleotide comprises a LNA unit according any of the formulas shown in "Scheme 2" of PCT/DK2006/000512.

Preferably, the LNA used in the oligomer of the invention comprises internucleoside linkages selected from —O—P(O)$_2$—O—, —O—P(O,S)—O—, —O—P(S)$_2$—O—, —S—P(O)$_2$—O—, —S—P(O,S)—O—, —S—P(S)$_2$—O—, —O—P(O)$_2$—S—, —O—P(O,S)—S—, —S—P(O)$_2$—S—, —O—PO(R$^H$)—O—, O—PO(OCH$_3$)—O—, —O—PO(NR$^H$)—O—, —O—PO(OCH$_2$CH$_2$S—R)—O—, —O—PO(BH$_3$)—O—, —O—PO(NHR$^H$)—O—, —O—P(O)$_2$—NR$^H$—, —NR$^H$—P(O)$_2$—O—, —NR$^H$—CO—O—, where R$^H$ is selected from hydrogen and C$_{1-4}$-alkyl.

Specifically, preferred LNA units are shown in Scheme 1:

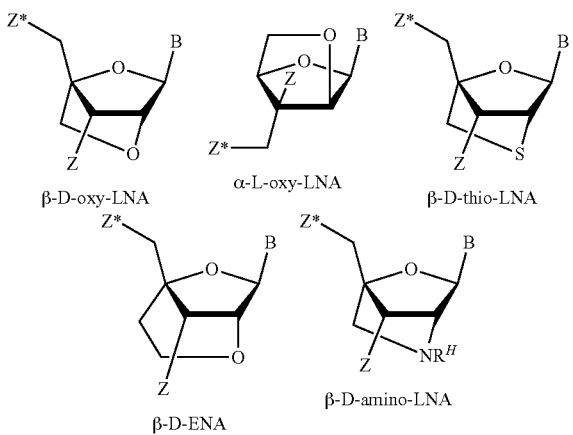

Scheme 1

β-D-oxy-LNA α-L-oxy-LNA β-D-thio-LNA

β-D-ENA β-D-amino-LNA

The term "thio-LNA" comprises a locked nucleotide in which at least one of X or Y in the general formula above is selected from S or —CH$_2$—S—. Thio-LNA can be in both beta-D and alpha-L-configuration.

The term "amino-LNA" comprises a locked nucleotide in which at least one of X or Y in the general formula above is selected from —N(H)—, N(R)—, CH$_2$—N(H)—, and —CH$_2$—N(R)— where R is selected from hydrogen and C$_{1-4}$-alkyl. Amino-LNA can be in both beta-D and alpha-L-configuration.

The term "oxy-LNA" comprises a locked nucleotide in which at least one of X or Y in the general formula above represents —O— or —CH$_2$—O—. Oxy-LNA can be in both beta-D and alpha-L-configuration.

The term "ena-LNA" comprises a locked nucleotide in which Y in the general formula above is —CH$_2$—O— (where the oxygen atom of —CH$_2$—O— is attached to the 2'-position relative to the base B). LNAs are described in additional detail below.

One or more substituted sugar moieties can also be included, e.g., one of the following at the 2' position: OH, SH, SCH$_3$, F, OCN, OCH$_3$, OCH$_3$ O(CH$_2$)n CH$_3$, O(CH$_2$)n NH$_2$ or O(CH$_2$)n CH$_3$ where n is from 1 to about 10; Ci to C10 lower alkyl, alkoxyalkoxy, substituted lower alkyl, alkaryl or aralkyl; Cl; Br; CN; CF3; OCF3; O—, S—, or N-alkyl; O—, S—, or N-alkenyl; SOCH$_3$; SO2 CH$_3$; ONO$_2$; NO$_2$; N$_3$; NH$_2$; heterocycloalkyl; heterocycloalkaryl; aminoalkylamino; polyalkylamino; substituted silyl; an RNA cleaving group; a reporter group; an intercalator; a group for improving the pharmacokinetic properties of an oligonucleotide; or a group for improving the pharmacodynamic properties of an oligonucleotide and other substituents having similar properties. A preferred modification includes 2'-methoxyethoxy [2'-O—CH$_2$CH$_2$OCH$_3$, also known as 2'-O-(2-methoxyethyl)] (Martin et al, Helv. Chim. Acta, 1995, 78, 486). Other preferred modifications include 2'-methoxy (2'-O—CH$_3$), 2'-propoxy (2'-OCH$_2$ CH$_2$CH$_3$) and 2'-fluoro (2'-F). Similar modifications may also be made at other positions on the oligonucleotide, particularly the 3' position of the sugar on the 3' terminal nucleotide and the 5' position of 5' terminal nucleotide. Oligonucleotides may also have sugar mimetics such as cyclobutyls in place of the pentofuranosyl group.

Inhibitory nucleic acids can also include, additionally or alternatively, nucleobase (often referred to in the art simply as "base") modifications or substitutions. As used herein, "unmodified" or "natural" nucleobases include adenine (A), guanine (G), thymine (T), cytosine (C) and uracil (U). Modified nucleobases include nucleobases found only infrequently or transiently in natural nucleic acids, e.g., hypoxanthine, 6-methyladenine, 5-Me pyrimidines, particularly 5-methylcytosine (also referred to as 5-methyl-2' deoxycytosine and often referred to in the art as 5-Me-C), 5-hydroxymethylcytosine (HMC), glycosyl HMC and gentobiosyl HMC, isocytosine, pseudoisocytosine, as well as synthetic nucleobases, e.g., 2-aminoadenine, 2-(methylamino)adenine, 2-(imidazolylalkyl)adenine, 2-(aminoalkylamino)adenine or other heterosubstituted alkyladenines, 2-thiouracil, 2-thiothymine, 5-bromouracil, 5-hydroxymethyluracil, 5-propynyluracil, 8-azaguanine, 7-deazaguanine, N6 (6-aminohexyl)adenine, 6-aminopurine, 2-aminopurine, 2-chloro-6-aminopurine and 2,6-diaminopurine or other diaminopurines. See, e.g., Kornberg (1980) DNA Replication, W. H. Freeman & Co., San Francisco, pp. 75-77; and Gebeyehu et al. (1987) Nucl. Acids Res. 15: 4513-34). A "universal" base known in the art, e.g., inosine, can also be included. 5-Me-C substitutions have been shown to increase nucleic acid duplex stability by 0.6-1.2<0>C. (Sanghvi, in Crooke, and Lebleu, eds., *Antisense Research and Applications*, CRC Press, Boca Raton, 1993, pp. 276-278).

It is not necessary for all positions in a given oligonucleotide to be uniformly modified, and in fact more than one of the modifications described herein may be incorporated in a single oligonucleotide or even at within a single nucleoside within an oligonucleotide.

In some embodiments, both a sugar and an internucleoside linkage, i.e., the backbone, of the nucleotide units are replaced with novel groups. The base units are maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, for example, an aminoethylglycine backbone. The nucleobases are retained and are bound directly or indirectly to aza nitrogen atoms of the amide portion of the backbone. Representative U.S. patents that teach the preparation of PNA compounds include, but are not limited to, U.S. Pat. Nos. 5,539,082; 5,714,331; and 5,719,262, each of which is herein incorporated by reference. Further teaching of PNA compounds can be found in Nielsen et al. (1991) *Science* 254: 1497-1500.

Inhibitory nucleic acids can also include one or more nucleobase (often referred to in the art simply as "base") modifications or substitutions. As used herein, "unmodified" or "natural" nucleobases comprise the purine bases adenine (A) and guanine (G), and the pyrimidine bases thymine (T), cytosine (C) and uracil (U). Modified nucleobases comprise other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudo-uracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylquanine and 7-methyladenine, 8-azaguanine and 8-azaadenine, 7-deazaguanine and 7-deazaadenine and 3-deazaguanine and 3-deazaadenine.

Further, nucleobases comprise those disclosed in U.S. Pat. No. 3,687,808, those disclosed in "*The Concise Encyclopedia of Polymer Science And Engineering*", pages 858-9, Kroschwitz, ed. John Wiley & Sons, 1990; those disclosed by Englisch et al. (1991) *Angewandte Chemie, International Edition* 30: 613; and those disclosed by Sanghvi et al. *Antisense Research and Applications*, chapter 15, pp. 289-302, Crooke and Lebleu, eds., CRC Press, 1993. Certain of these nucleobases are particularly useful for increasing the binding affinity of the oligomeric compounds. These include 5-substituted pyrimidines, 6-azapyrimidines and N-2, N-6 and 0-6 substituted purines, comprising 2-aminopropyladenine, 5-propynyluracil and 5-propynylcytosine. 5-methyl-cytosine substitutions have been shown to increase nucleic acid duplex stability by 0.6-1.2° C. (Sanghvi et al., *Antisense Research and Applications*, pp. 276-8, Crooke and Lebleu, eds., CRC Press, 1993) and are presently preferred base substitutions, even more particularly when combined with 2'-O-methoxyethyl sugar modifications. Modified nucleobases are described in U.S. Pat. Nos. 3,687,808; 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,596,091; 5,614,617; 5,750,692; and 5,681,941, each of which is herein incorporated by reference.

In some embodiments, the inhibitory nucleic acids are chemically linked to one or more moieties or conjugates that enhance the activity, cellular distribution, or cellular uptake of the oligonucleotide. For example, one or more inhibitory nucleic acids, of the same or different types, can be conjugated to each other; or inhibitory nucleic acids can be conjugated to targeting moieties with enhanced specificity for a cell type or tissue type. Such moieties include, but are not limited to, lipid moieties such as a cholesterol moiety (Letsinger et al. (1989) *Proc. Natl. Acad. Sci. U.S.A.* 86: 6553-6), cholic acid (Manoharan et al. (1994) *Bioorg. Med. Chem. Let.* 4: 1053-60), a thioether, e.g., hexyl-S-tritylthiol (Manoharan et al. (1992) *Ann. N Y. Acad. Sci.* 660: 306-9; Manoharan et al. (1993) *Bioorg. Med. Chem. Let.* 3: 2765-70), a thiocholesterol (Oberhauser et al. (1992) *Nucl. Acids Res.* 20: 533-8), an aliphatic chain, e.g., dodecandiol or undecyl residues (Kabanov et al. (1990) *FEBS Lett.* 259: 327-30; Svinarchuk et al. (1993) *Biochimie* 75: 49-54), a phospholipid, e.g., di-hexadecyl-rac-glycerol or triethylammonium 1,2-di-O-hexadecyl-rac-glycero-3-H-phosphonate (Manoharan et al. (1995) *Tetrahedron Lett.* 36: 3651-4; Shea et al. (1990) *Nucl. Acids Res.* 18: 3777-83), a polyamine or a polyethylene glycol chain (Mancharan et al. (1995) *Nucleosides & Nucleotides* 14: 969-973), or adamantane acetic acid (Manoharan et al. (1995) *Tetrahedron Lett.* 36: 3651-4), a palmityl moiety (Mishra et al. (1995) *Biochim. Biophys. Acta* 1264: 229-37), or an octadecylamine or hexylamino-carbonyl-t oxycholesterol moiety (Crooke et al. (1996) *J. Pharmacol. Exp. Ther.* 277: 923-37). See also U.S. Pat. Nos. 4,828,979; 4,948,882; 5,218,105; 5,525,465; 5,541,313; 5,545,730; 5,552, 538; 5,578,717; 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5, 245,022; 5,254,469; 5,258,506; 5,262,536; 5,272,250; 5,292,873; 5,317,098; 5,371,241, 5,391,723; 5,416,203, 5,451,463; 5,510,475; 5,512,667; 5,514,785; 5, 565,552; 5,567,810; 5,574,142; 5,585,481; 5,587,371; 5,595,726; 5,597,696; 5,599,923; 5,599,928 and 5,688,941, each of which is herein incorporated by reference.

These moieties or conjugates can include conjugate groups covalently bound to functional groups such as primary or secondary hydroxyl groups. Conjugate groups of the invention include intercalators, reporter molecules, polyamines, polyamides, polyethylene glycols, polyethers, groups that enhance the pharmacodynamic properties of oligomers, and groups that enhance the pharmacokinetic properties of oligomers. Typical conjugate groups include cholesterols, lipids, phospholipids, biotin, phenazine, folate, phenanthridine, anthraquinone, acridine, fluoresceins, rhodamines, coumarins, and dyes. Groups that enhance the pharmacodynamic properties, in the context of this invention, include groups that improve uptake, enhance resistance to degradation, and/or strengthen sequence-specific hybridization with the target nucleic acid. Groups that enhance the pharmacokinetic properties, in the context of this invention, include groups that improve uptake, distribution, metabolism or excretion of the compounds of the present invention. Representative conjugate groups are disclosed in International Publication No. WO 1993/007883, and U.S. Pat. No.

6,287,860, both of which are incorporated herein by reference. Conjugate moieties include, but are not limited to, lipid moieties such as a cholesterol moiety, cholic acid, a thioether, e.g., hexyl-5-tritylthiol, a thiocholesterol, an aliphatic chain, e.g., dodecandiol or undecyl residues, a phospholipid, e.g., di-hexadecyl-rac-glycerol or triethylammonium 1,2-di-O-hexadecyl-rac-glycero-3-H-phosphonate, a polyamine or a polyethylene glycol chain, or adamantane acetic acid, a palmityl moiety, or an octadecylamine or hexylamino-carbonyl-oxy cholesterol moiety. See, e.g., U.S. Pat. Nos. 4,828,979; 4,948,882; 5,218,105; 5,525,465; 5,541,313; 5,545,730; 5,552,538; 5,578,717; 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241; 5,391,723; 5,416,203; 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928; and 5,688,941.

The inhibitory nucleic acids useful in the methods described herein are sufficiently complementary to the target RNA, e.g., hybridize sufficiently well and with sufficient biological functional specificity, to give the desired effect. "Complementary" refers to the capacity for pairing, through base stacking and specific hydrogen bonding, between two sequences comprising naturally or non-naturally occurring (e.g., modified as described above) bases (nucleosides) or analogs thereof. For example, if a base at one position of an inhibitory nucleic acid is capable of hydrogen bonding with a base at the corresponding position of an RNA, then the bases are considered to be complementary to each other at that position. In some embodiments, 100% complementarity is not required. As noted above, inhibitory nucleic acids can comprise universal bases, or inert abasic spacers that provide no positive or negative contribution to hydrogen bonding. Base pairings may include both canonical Watson-Crick base pairing and non-Watson-Crick base pairing (e.g., Wobble base pairing and Hoogsteen base pairing). It is understood that for complementary base pairings, adenosine-type bases (A) are complementary to thymidine-type bases (T) or uracil-type bases (U), that cytosine-type bases (C) are complementary to guanosine-type bases (G), and that universal bases such as such as 3-nitropyrrole or 5-nitroindole can hybridize to and are considered complementary to any A, C, U, or T (see Nichols et al. (1994) *Nature* 369: 492-3 and Loakes et al. (1994) *Nucleic Acids Res.* 22: 4039-43. Inosine (I) has also been considered in the art to be a universal base and is considered complementary to any A, C, U, or T. See Watkins and Santa Lucia (2005) *Nucl. Acids Res.* 33(19): 6258-67.

Additional target segments in a nucleic acid are readily identifiable by one having ordinary skill in the art in view of this disclosure. Target segments 5-500 nucleotides in length comprising a stretch of at least five (5) consecutive nucleotides within the protein binding region, or immediately adjacent thereto, are considered to be suitable for targeting as well. Target segments can include sequences that comprise at least the 5 consecutive nucleotides from the 5'-terminus of one of the protein binding regions (the remaining nucleotides being a consecutive stretch of the same RNA beginning immediately upstream of the 5'-terminus of the binding segment and continuing until the inhibitory nucleic acid contains about 5 to about 100 nucleotides). Similarly preferred target segments are represented by RNA sequences that comprise at least the 5 consecutive nucleotides from the 3'-terminus of one of the illustrative preferred target segments (the remaining nucleotides being a consecutive stretch of the same RNA beginning immediately downstream of the 3'-terminus of the target segment and continuing until the inhibitory nucleic acid contains about 5 to about 100 nucleotides). One having skill in the art armed with the sequences provided herein will be able, without undue experimentation, to identify further preferred protein binding regions to target with complementary inhibitory nucleic acids.

It is understood in the art that a complementary nucleic acid sequence need not be 100% complementary to that of its target nucleic acid to be specifically hybridizable. A complementary nucleic acid sequence for purposes of the present methods is specifically hybridizable when binding of the sequence to the target RNA molecule interferes with the normal function of the target RNA to cause a loss of activity (e.g., inhibiting the translation of an mRNA encoding GPERs) and there is a sufficient degree of complementarity to avoid non-specific binding of the sequence to non-target RNA sequences under conditions in which avoidance of the non-specific binding is desired, e.g., under physiological conditions in the case of in vivo assays or therapeutic treatment, and in the case of in vitro assays, under conditions in which the assays are performed under suitable conditions of stringency. For example, stringent salt concentration will ordinarily be less than about 750 mM NaCl and 75 mM trisodium citrate, preferably less than about 500 mM NaCl and 50 mM trisodium citrate, and more preferably less than about 250 mM NaCl and 25 mM trisodium citrate. Low stringency hybridization can be obtained in the absence of organic solvent, e.g., formamide, while high stringency hybridization can be obtained in the presence of at least about 35% formamide, and more preferably at least about 50% formamide. Stringent temperature conditions will ordinarily include temperatures of at least about 30° C., more preferably of at least about 37° C., and most preferably of at least about 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In a preferred embodiment, hybridization will occur at 30° C. in 750 mM NaCl, 75 mM trisodium citrate, and 1% SDS. In a more preferred embodiment, hybridization will occur at 37° C. in 500 mM NaCl, 50 mM trisodium citrate, 1% SDS, 35% formamide, and 100 µg/ml denatured salmon sperm DNA (ssDNA). In a most preferred embodiment, hybridization will occur at 42° C. in 250 mM NaCl, 25 mM trisodium citrate, 1% SDS, 50% formamide, and 200 µg/ml ssDNA. Useful variations on these conditions will be readily apparent to those skilled in the art.

For most applications, washing steps that follow hybridization will also vary in stringency. Wash stringency conditions can be defined by salt concentration and by temperature. As above, wash stringency can be increased by decreasing salt concentration or by increasing temperature. For example, stringent salt concentration for the wash steps will preferably be less than about 30 mM NaCl and 3 mM trisodium citrate, and most preferably less than about 15 mM NaCl and 1.5 mM trisodium citrate. Stringent temperature conditions for the wash steps will ordinarily include a temperature of at least about 25° C., more preferably of at least about 42° C., and even more preferably of at least about 68° C. In a preferred embodiment, wash steps will occur at 25° C. in 30 mM NaCl, 3 mM trisodium citrate, and 0.1%

SDS. In a more preferred embodiment, wash steps will occur at 42° C. in 15 mM NaCl, 1.5 mM trisodium citrate, and 0.1% SDS. In a more preferred embodiment, wash steps will occur at 68° C. in 15 mM NaCl, 1.5 mM trisodium citrate, and 0.1% SDS. Additional variations on these conditions will be readily apparent to those skilled in the art. Hybridization techniques are well known to those skilled in the art and are described, for example, in Benton and Davis (1977) *Science* 196: 180); Grunstein and Hogness (1975) *Proc. Natl. Acad. Sci. USA* 72: 3961); Ausubel et al. (2001) *Current Protocols in Molecular Biology*, Wiley Interscience, New York); Berger and Kimmel (1987) *Guide to Molecular Cloning Techniques*, Academic Press, New York); and Sambrook et al., *Molecular Cloning: A Laboratory Manual*, 3d. ed., 2001, Cold Spring Harbor Laboratory Press, New York.

In general, the inhibitory nucleic acids useful in the methods described herein have at least 80% sequence complementarity to a target region within the target nucleic acid, e.g., 80%, 85%, 90%, 95%, or 100% sequence complementarity to the target region within an RNA. For example, an antisense compound in which 18 of 20 nucleobases of the antisense oligonucleotide are complementary, and would therefore specifically hybridize, to a target region would represent 90 percent complementarity. Percent complementarity of an inhibitory nucleic acid with a region of a target nucleic acid can be determined routinely using basic local alignment search tools (BLAST programs) (Altschul et al. (1990) *J. Mol. Biol.* 215: 403-10; Zhang and Madden (1997) *Genome Res.* 7: 649-56). Antisense and other compounds of the invention that hybridize to an RNA are identified through routine experimentation. In general the inhibitory nucleic acids must retain specificity for their target, i.e., either do not directly bind to, or do not directly significantly affect expression levels of, transcripts other than the intended target.

Target-specific effects, with corresponding target-specific functional biological effects, are possible even when the inhibitory nucleic acid exhibits non-specific binding to a large number of non-target RNAs. For example, short 8 base long inhibitory nucleic acids that are fully complementary to a RNA may have multiple 100% matches to hundreds of sequences in the genome, yet may produce target-specific effects, e.g. downregulation of a gper1 gene. 8-base inhibitory nucleic acids have been reported to prevent exon skipping with a high degree of specificity and reduced off-target effect. See Singh et al. (2009) *RNA Biol.* 6(3): 341-350. 8-base inhibitory nucleic acids have been reported to interfere with miRNA activity without significant off-target effects. See Obad et al. (2011) *Nature Genetics* 43: 371-8.

For further disclosure regarding inhibitory nucleic acids, please see U.S. Publication Nos. 2010/0317718 (antisense oligos); 2010/0249052 (double-stranded ribonucleic acid (dsRNA)); 2009/0181914 and 2010/0234451 (LNA molecules); 2007/0191294 (siRNA analogues); 2008/0249039 (modified siRNA molecules); and International Publication No. WO 2010/129746 and WO 2010/040112 (inhibitory nucleic acids).

Antisense Oligonucleotides

In some embodiments, the inhibitory nucleic acids are antisense oligonucleotides. Antisense oligonucleotides are typically designed to block expression of a DNA or RNA target by binding to the target and halting expression at the level of transcription, translation, or splicing. Antisense oligonucleotides of the present invention are complementary nucleic acid sequences designed to hybridize under stringent conditions to an RNA in vitro, and are expected to reduce and/or reduce the level of transcription, translation, or splicing of a nucleic acid encoding GPER1. Thus, oligonucleotides are chosen that are sufficiently complementary to the target, i.e., that hybridize sufficiently well and with sufficient biological functional specificity, to give the desired effect.

Modified Base, Including Locked Nucleic Acids (LNAs)

In some embodiments, the inhibitory nucleic acids used in the methods described herein comprise one or more modified bonds or bases. Modified bases include phosphorothioate, methylphosphonate, peptide nucleic acids, or locked nucleic acids (LNAs). Preferably, the modified nucleotides are part of locked nucleic acid molecules, including [alpha]-L-LNAs. LNAs include ribonucleic acid analogues wherein the ribose ring is "locked" by a methylene bridge between the 2'-oxygen and the 4'-carbon—i.e., oligonucleotides containing at least one LNA monomer, that is, one 2'-O, 4'-C-methylene-β-D-ribofuranosyl nucleotide. LNA bases form standard Watson-Crick base pairs but the locked configuration increases the rate and stability of the basepairing reaction (Jepsen et al. (2004) *Oligonucleotides* 14: 130-146). LNAs also have increased affinity to base pair with RNA as compared to DNA. These properties render LNAs especially useful as probes for fluorescence in situ hybridization (FISH) and comparative genomic hybridization, as knockdown tools for miRNAs, and as antisense oligonucleotides to target mRNAs or other RNAs, e.g., RNAs as described herein.

The modified base/LNA molecules can include molecules comprising 10-30, e.g., 12-24, e.g., 12, 13, 14, 15, 16, 17, 18, 19, 20, 21, 22, 23, 24, 25, 26, 27, 28, 29, or 30 nucleotides in each strand, wherein one of the strands is substantially identical, e.g., at least 80% (or more, e.g., 85%, 90%, 95%, or 100%) identical, e.g., having 3, 2, 1, or 0 mismatched nucleotide(s), to a target region in the RNA. The modified base/LNA molecules can be chemically synthesized using methods known in the art.

The modified base/LNA molecules can be designed using any method known in the art; a number of algorithms are known, and are commercially available (e.g., on the internet, for example at exiqon.com). See, e.g., You et al. (2006) *Nucl. Acids. Res.* 34: e60; McTigue et al. (2004) *Biochemistry* 43: 5388-405; and Levin et al. (2006) *Nucl. Acids. Res.* 34: e142. For example, "gene walk" methods, similar to those used to design antisense oligos, can be used to optimize the inhibitory activity of a modified base/LNA molecule; for example, a series of oligonucleotides of 10-30 nucleotides spanning the length of a target RNA can be prepared, followed by testing for activity. Optionally, gaps, e.g., of 5-10 nucleotides or more, can be left between the LNAs to reduce the number of oligonucleotides synthesized and tested. GC content is preferably between about 30-60%. General guidelines for designing modified base/LNA molecules are known in the art; for example, LNA sequences will bind very tightly to other LNA sequences, so it is preferable to avoid significant complementarity within an LNA molecule. Contiguous runs of three or more Gs or Cs, or more than four LNA residues, should be avoided where possible (for example, it may not be possible with very short (e.g., about 9-10 nt) oligonucleotides). In some embodiments, the LNAs are xylo-LNAs.

For additional information regarding LNA molecules see U.S. Pat. Nos. 6,268,490; 6,734,291; 6,770,748; 6,794,499; 7,034,133; 7,053,207; 7,060,809; 7,084,125; and 7,572,582; and U.S. Publication Nos. 2010/0267018; 2010/0261175; and 2010/0035968; Koshkin et al. (1998) *Tetrahedron* 54: 3607-30; Obika et al. (1998) *Tetrahedron Lett.* 39: 5401-4; Jepsen et al. (2004) *Oligonucleotides* 14: 130-46; Kauppinen et al. (2005) *Drug Disc. Today* 2(3): 287-90; and Ponting et al. (2009) *Cell* 136(4): 629-41, and references cited therein.

As demonstrated herein and previously (see, e.g., International Publication Nos. WO 2012/065143 and WO 2012/087983, incorporated herein by reference), LNA molecules can be used as a valuable tool to manipulate and aid analysis of RNAs. Advantages offered by an LNA molecule-based system are the relatively low costs, easy delivery, and rapid action. While other inhibitory nucleic acids may exhibit effects after longer periods of time, LNA molecules exhibit effects that are more rapid, e.g., a comparatively early onset of activity, are fully reversible after a recovery period following the synthesis of new RNA, and occur without causing substantial or substantially complete RNA cleavage or degradation. One or more of these design properties may be desired properties of the inhibitory nucleic acids of the invention. Additionally, LNA molecules make possible the systematic targeting of domains within much longer nuclear transcripts. Although a PNA-based system has been described earlier, the effects on Xi were apparent only after 24 hours (Beletskii et al. (2001) *Proc. Natl. Acad. Sci. U.S.A.* 98: 9215-20). The LNA technology enables high-throughput screens for functional analysis of non-coding RNAs and also provides a novel tool to manipulate chromatin states in vivo for therapeutic applications.

In various related aspects, the methods described herein include using LNA molecules to target RNAs for a number of uses, including as a research tool to probe the function of a specific RNA, e.g., in vitro or in vivo. The methods include selecting one or more desired RNAs, designing one or more LNA molecules that target the RNA, providing the designed LNA molecule, and administering the LNA molecule to a cell or animal. The methods can optionally include selecting a region of the RNA and designing one or more LNA molecules that target that region of the RNA.

From a commercial and clinical perspective, the time points between about 1 to 24 hours potentially define a window for epigenetic reprogramming. The advantage of the LNA system is that it works quickly, with a defined half-life, and is therefore reversible upon degradation of LNAs, at the same time that it provides a discrete timeframe during which epigenetic manipulations can be made. By targeting nuclear long RNAs, LNA molecules or similar polymers, e.g., xylo-LNAs, might be utilized to manipulate the chromatin state of cells in culture or in vivo, by transiently eliminating the regulatory RNA and associated proteins long enough to alter the underlying locus for therapeutic purposes. In particular, LNA molecules or similar polymers that specifically bind to, or are complementary to, a nucleic acid encoding GPER1 can inhibit the expression of the protein, in a gene-specific fashion.

Interfering RNA, Including siRNA/shRNA

In some embodiments, the inhibitory nucleic acid sequence that is complementary to an RNA can be an interfering RNA, including but not limited to a small interfering RNA ("siRNA") or a small hairpin RNA ("shRNA"). Methods for constructing interfering RNAs are well known in the art. For example, the interfering RNA can be assembled from two separate oligonucleotides, where one strand is the sense strand and the other is the antisense strand, wherein the antisense and sense strands are self-complementary (i.e., each strand comprises nucleotide sequence that is complementary to nucleotide sequence in the other strand; such as where the antisense strand and sense strand form a duplex or double stranded structure); the antisense strand comprises nucleotide sequence that is complementary to a nucleotide sequence in a target nucleic acid molecule or a portion thereof (i.e., an undesired gene) and the sense strand comprises nucleotide sequence corresponding to the target nucleic acid sequence or a portion thereof. Alternatively, interfering RNA is assembled from a single oligonucleotide, where the self-complementary sense and antisense regions are linked by means of nucleic acid based or non-nucleic acid-based linker(s). The interfering RNA can be a polynucleotide with a duplex, asymmetric duplex, hairpin or asymmetric hairpin secondary structure, having self-complementary sense and antisense regions, wherein the antisense region comprises a nucleotide sequence that is complementary to nucleotide sequence in a separate target nucleic acid molecule or a portion thereof and the sense region having nucleotide sequence corresponding to the target nucleic acid sequence or a portion thereof. The interfering can be a circular single-stranded polynucleotide having two or more loop structures and a stem comprising self-complementary sense and antisense regions, wherein the antisense region comprises nucleotide sequence that is complementary to nucleotide sequence in a target nucleic acid molecule or a portion thereof and the sense region having nucleotide sequence corresponding to the target nucleic acid sequence or a portion thereof, and wherein the circular polynucleotide can be processed either in vivo or in vitro to generate an active siRNA molecule capable of mediating RNA interference.

In some embodiments, the interfering RNA coding region encodes a self-complementary RNA molecule having a sense region, an antisense region and a loop region. Such an RNA molecule when expressed desirably forms a "hairpin" structure, and is referred to herein as a "snRNA." The loop region is generally between about 2 and about 10 nucleotides in length. In some embodiments, the loop region is from about 6 to about 9 nucleotides in length. In some embodiments, the sense region and the antisense region are between about 15 and about 20 nucleotides in length. Following post-transcriptional processing, the small hairpin RNA is converted into a siRNA by a cleavage event mediated by the enzyme Dicer, which is a member of the RNase III family. The siRNA is then capable of inhibiting the expression of a gene with which it shares homology. For details, see Brummelkamp et al. (2002) *Science* 296: 550-3; Lee et al. (2002) *Nature Biotechnol.* 20: 500-5; Miyagishi and Taira (2002) *Nature Biotechnol.* 20: 497-500; Paddison et al. (2002) *Genes & Dev.* 16: 948-58; Paul (2002) *Nature Biotechnol.* 20: 505-08; Sui (2002) *Proc. Natl. Acad. Sci. U.S.A.* 99(6): 5515-20; Yu et al. (2002) *Proc. Natl. Acad. Sci. U.S.A.* 99: 6047-52.

The target RNA cleavage reaction guided by siRNAs is highly sequence specific. In general, siRNA containing a nucleotide sequence identical to a portion of the target nucleic acid are preferred for inhibition. However, 100% sequence identity between the siRNA and the target gene is not required. Thus, the design of the siRNAs has the advantage of being able to tolerate sequence variations that might be expected due to genetic mutation, strain polymorphism, or evolutionary divergence. For example, siRNA sequences with insertions, deletions, and single point mutations relative to the target sequence have also been found to be effective for inhibition. Alternatively, siRNA sequences with nucleotide analog substitutions or insertions can be effective for inhibition. In general, the siRNAs must retain specificity for their target, i.e., must not directly bind to, or directly significantly affect expression levels of, transcripts other than the intended target.

Ribozymes

In some embodiments, the inhibitory nucleic acids are ribozymes. Trans-cleaving enzymatic nucleic acid molecules can also be used; they have shown promise as therapeutic agents for human disease (Usman & McSwiggen (1995) *Ann. Rep. Med. Chem.* 30: 285-94; Christoffersen and Marr (1995) *J. Med. Chem.* 38: 2023-37). Enzymatic nucleic acid molecules can be designed to cleave specific RNA targets within the background of cellular RNA. Such a cleavage event renders the RNA non-functional.

In general, enzymatic nucleic acids with RNA cleaving activity act by first binding to a target RNA. Such binding occurs through the target binding portion of an enzymatic nucleic acid which is held in close proximity to an enzymatic portion of the molecule that acts to cleave the target RNA. Thus, the enzymatic nucleic acid first recognizes and then binds a target RNA through complementary base pairing, and once bound to the correct site, acts enzymatically to cut the target RNA. Strategic cleavage of such a target RNA will destroy its ability to direct synthesis of an encoded protein. After an enzymatic nucleic acid has bound and cleaved its RNA target, it is released from that RNA to search for another target and can repeatedly bind and cleave new targets.

Several approaches such as in vitro selection (evolution) strategies have been used to evolve new nucleic acid catalysts capable of catalyzing a variety of reactions, such as cleavage and ligation of phosphodiester linkages and amide linkages, (Orgel (1979) *Proc. R. Soc. London B* 205: 435; Joyce (1989) *Gene* 82: 83-87; Beaudry et al. (1992) *Science* 257: 635-41; Joyce (1992) *Scientific American* 267: 90-97; Breaker et al. (1994) *TIBTECH* 12: 268; Bartel et al. (1993) *Science* 261: 1411-8; Szostak (1993) *TIBS* 17: 89-93; Kumar et al. (1995) *FASEB J.* 9: 1183; Breaker (1996) *Curr. Op. Biotech.* 1: 442). The development of ribozymes that are optimal for catalytic activity would contribute significantly to any strategy that employs RNA-cleaving ribozymes for the purpose of regulating gene expression. The hammerhead ribozyme, for example, functions with a catalytic rate (kcat) of about 1 min$^{-1}$ in the presence of saturating (10 mM) concentrations of Mg$^{2+}$ cofactor. An artificial "RNA ligase" ribozyme has been shown to catalyze the corresponding self-modification reaction with a rate of about 100 min$^{-1}$. In addition, it is known that certain modified hammerhead ribozymes that have substrate binding arms made of DNA catalyze RNA cleavage with multiple turn-over rates that approach 100 min$^{-1}$.

Making and Using Inhibitory Nucleic Acids

The nucleic acid sequences used to practice the methods described herein, whether RNA, cDNA, genomic DNA, vectors, viruses or hybrids thereof, can be isolated from a variety of sources, genetically engineered, amplified, and/or expressed/generated recombinantly. If desired, nucleic acid sequences of the invention can be inserted into delivery vectors and expressed from transcription units within the vectors. The recombinant vectors can be DNA plasmids or viral vectors. Generation of the vector construct can be accomplished using any suitable genetic engineering techniques well known in the art, including, without limitation, the standard techniques of PCR, oligonucleotide synthesis, restriction endonuclease digestion, ligation, transformation, plasmid purification, and DNA sequencing, for example as described in Sambrook et al., *Molecular Cloning: A Laboratory Manual*, 3d. ed., 2001, Cold Spring Harbor Laboratory Press, New York, Coffin et al. (Retroviruses. (1997)) and "RNA Viruses: A Practical Approach" (Alan J. Cann, Ed., Oxford University Press, (2000)).

Preferably, inhibitory nucleic acids of the invention are synthesized chemically. Nucleic acid sequences used to practice this invention can be synthesized in vitro by well-known chemical synthesis techniques, as described in, e.g., Adams (1983) J. Am. Chem. Soc. 105:661; Belousov (1997) Nucleic Acids Res. 25:3440-3444; Frenkel (1995) Free Radic. Biol. Med. 19:373-380; Blommers (1994) Biochemistry 33:7886-7896; Narang (1979) Meth. Enzymol. 68:90; Brown (1979) Meth. Enzymol. 68:109; Beaucage (1981) Tetra. Lett. 22:1859; U.S. Pat. No. 4,458,066; WO/2008/043753 and WO/2008/049085, and the references cited therein.

Nucleic acid sequences of the invention can be stabilized against nucleolytic degradation such as by the incorporation of a modification, e.g., a nucleotide modification. For example, nucleic acid sequences of the invention include a phosphorothioate at least the first, second, or third internucleotide linkage at the 5' or 3' end of the nucleotide sequence. As another example, the nucleic acid sequence can include a 2'-modified nucleotide, e.g., a 2'-deoxy, 2'-deoxy-2'-fluoro, 2'-O-methyl, 2'-O-methoxyethyl (2'-O-MOE), 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), or 2'-O—N-methylacetamido (2'-O-NMA). As another example, the nucleic acid sequence can include at least one 2'-O-methyl-modified nucleotide, and in some embodiments, all of the nucleotides include a 2'-O-methyl modification. In some embodiments, the nucleic acids are "locked," i.e., comprise nucleic acid analogues in which the ribose ring is "locked" by a methylene bridge connecting the 2'-O atom and the 4'-C atom (see, e.g., Kaupinnen et al., Drug Disc. Today 2(3):287-290 (2005); Koshkin et al., J. Am. Chem. Soc., 120(50):13252-13253 (1998)). For additional modifications see US 20100004320, US 20090298916, and US 20090143326.

It is understood that any of the modified chemistries or formats of inhibitory nucleic acids described herein can be combined with each other, and that one, two, three, four, five, or more different types of modifications can be included within the same molecule.

Techniques for the manipulation of nucleic acids used to practice this invention, such as, e.g., subcloning, labeling probes (e.g., random-primer labeling using Klenow polymerase, nick translation, amplification), sequencing, hybridization and the like are well described in the scientific and patent literature, see, e.g., Sambrook et al., *Molecular Cloning: A Laboratory Manual*, 3d. ed., 2001, Cold Spring Harbor Laboratory Press, New York; Ausubel et al., eds., *Current Protocols in Molecular Biology*, 2010, John Wiley & Sons, Inc., New York; Kriegler *Gene Transfer and Expression: A Laboratory Manual*, 1990; *Laboratory Techniques In Biochemistry And Molecular Biology: Hybridization With Nucleic Acid Probes*, Part I. Theory and Nucleic Acid Preparation, 1993, Tijssen, ed. Elsevier, New York.

Programmable RNA-Guided Nuclease Systems

In some embodiments, the inhibitor of GPER1 comprises a programmable RNA-guided nuclease system that edits or disrupts a gper1 gene. Relevant nuclease systems that may be used include, but are not limited to: zinc finger nucleases, transcription activator-like effector nucleases (TALEN5), meganucleases, and CRISPR/Cas9 nuclease systems. As used herein, the term "edits" in reference to a programmable RNA-guided nuclease system includes mutations such as, a point mutation, an insertion, a deletion, a frameshift, or a missense mutation at a target nucleic acid.

In some embodiments, the inhibitor of GPER1 comprises a programmable RNA-guided nuclease system that specifically targets a nucleic acid encoding GPER1. The RNA-guided nuclease system includes guide RNAs comprising a sequence that is complementary to the sequence of a nucleic acid (i.e., a targeting domain) in the gper1 gene, and a sequence (e.g., a PAM sequence) that is targetable by a nuclease molecule (e.g., a Cas9 molecule). Upon successful targeting, the nuclease molecule cleaves the targeted nucleic acid.

The components of the nuclease system may be delivered to a subject as proteins, nucleic acids, or a combination of both.

In some embodiments, the inhibitor of GPER1 includes guide RNAs directing the editing enzyme (e.g., a Cas9 enzyme) to a nucleic acid encoding GPER1, i.e., comprising a sequence that is complementary to the sequence of a nucleic acid encoding GPER1, and that include a PAM sequence that is targetable by a co-administered nuclease (e.g., a Cas9 enzyme).

In some embodiments, the inhibitor of GPER1 comprises a Cas9 molecule and a guide RNA that targets the Cas9 molecule to a nucleic acid encoding GPER1 (e.g., a gper1 gene). Preferably a single guide RNA (sgRNA) is used, though a crRNA/tracrRNA pair can also be used.

The sequences of multiple Cas9 molecules, as well as their respective PAM sequences, are known in the art (see, e.g., Kleinstiver et al. (2015) *Nature* 523 (7561): 481-5; Hou et al. (2013) *Proc. Natl. Acad. Sci. U.S.A.* 110(39): 15644-9; Fonfara et al. (2014) *Nucleic Acids Res.* 42: 2577-90; Esvelt et al. (2013) *Nat. Methods* 10: 1116-21; Cong et al. (2013) *Science* 339: 819-23; and Horvath et al. (2008) *J. Bacteria* 190: 1401-12; PCT Publication Nos. WO 2016/141224, WO 2014/204578, and WO 2014/144761; U.S. Pat. No. 9,512,446; and US Publication No. 2014/0295557; the entire contents of each of which are incorporated herein by reference). In some embodiments, the Cas9 molecule is an *Streptococcus pyogenes* Cas9 molecule (spCas9). Variants of the SpCas9 system can also be used (e.g., truncated sgRNAs (Tsai et al. (2015) *Nat. Biotechnol.* 33: 187-97; Fu et al. (2014) *Nat. Biotechnol.* 32: 279-84), nickase mutations (Mali et al. (2013) *Nat. Biotechnol.* 31: 833-8 (2013); Ran et al. (2013) *Cell* 154: 1380-9), FokI-dCas9 fusions (Guilinger et al. (2014) *Nat. Biotechnol.* 32: 577-82; Tsai et al. (2014) *Nat. Biotechnol.* 32: 569-76; and PCT Publication No. WO 2014/144288; the entire contents of each of which are incorporated herein by reference). The nucleases can include one or more of SpCas9 D1135E variant; SpCas9 VRER variant; SpCas9 EQR variant; SpCas9 VQR variant; *Streptococcus thermophilus* Cas9 molecule (StCas9); *Treponema denticola* Cas9 molecule (TdCas9); or *Neisseria meningitidis* Cas9 molecule (NmCas9), as well as variants thereof that are at least 80%, 85%, 90%, 95%, 96%, 97%, 98%, 99% or 100% identical thereto that retain at least one function of the enzyme from which they are derived, e.g., the ability to complex with a gRNA, bind to target DNA specified by the gRNA, and alter the sequence (e.g., cleave) of the target DNA.

To determine the percent identity of two sequences, the sequences are aligned for optimal comparison purposes (gaps are introduced in one or both of a first and a second amino acid or nucleic acid sequence as required for optimal alignment, and non-homologous sequences can be disregarded for comparison purposes). The length of a reference sequence aligned for comparison purposes is at least 80% (in some embodiments, about 85%, 90%, 95%, or 100% of the length of the reference sequence) is aligned. The nucleotides or residues at corresponding positions are then compared. When a position in the first sequence is occupied by the same nucleotide or residue as the corresponding position in the second sequence, then the molecules are identical at that position. The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. For example, the percent identity between two amino acid sequences can be determined using the Needleman and Wunsch algorithm (see Needleman and Wunsch (1970) *J. Mol. Biol.* 48: 444-53) which has been incorporated into the GAP program in the GCG software package, using a Blossum 62 scoring matrix with a gap penalty of 12, a gap extend penalty of 4, and a frameshift gap penalty of 5.

When the inhibitor of GPER1 comprising a RNA-guided nuclease system is delivered as one or more nucleic acids, expression constructs may be used. Expression constructs encoding one or both of guide RNAs and/or Cas9 editing enzymes can be administered in any effective carrier, e.g., any formulation or composition capable of effectively delivering the component gene to cells in vivo, in vitro, or ex vivo.

A preferred approach for in vivo introduction of nucleic acid into a cell is by use of a viral vector containing nucleic acid, e.g., a cDNA. Infection of cells with a viral vector has the advantage that a large proportion of the targeted cells can receive the nucleic acid. Additionally, molecules encoded within the viral vector, e.g., by a cDNA contained in the viral vector, are expressed efficiently in cells that have taken up viral vector nucleic acid.

In some embodiments, nucleic acids encoding a RNA-guided programmable nuclease system targeting a nucleic acid encoding the inhibitor of GPER1 (e.g., Cas9 and/or gRNA) are entrapped in liposomes bearing positive charges on their surface (e.g., lipofectins). These delivery vehicles can also be used to deliver Cas9 protein/gRNA complexes.

In clinical settings, the RNA-guided programmable nuclease systems can be introduced into a subject by any of a number of methods, each of which is familiar in the art. In some embodiments, the nucleic acids encoding a RNA-guided programmable nuclease system are administered during or after a surgical procedure; in some embodiments, a controlled-release hydrogel comprising the nucleic acids encoding a RNA-guided programmable nuclease system is administered to provide a steady dose of the nucleic acids encoding RNA-guided programmable nuclease system over time.

A pharmaceutical preparation of the nucleic acids encoding a RNA-guided programmable nuclease system can consist essentially of the gene delivery system (e.g., viral vector(s)) in an acceptable diluent, or can comprise a slow release matrix in which the gene delivery vehicle is embedded. Alternatively, where the complete gene delivery system can be produced intact from recombinant cells, e.g., retroviral vectors, the pharmaceutical preparation can comprise one or more cells, which produce the gene delivery system. In some embodiments, adeno-associated virus 1 (AAV1) vectors are used as a recombinant gene delivery system for the transfer and expression of the RNA-guided programmable nuclease system in vivo, particularly into humans. These vectors provide efficient delivery of genes into cells, and in some cases the transferred nucleic acids are stably integrated into the chromosomal DNA of the host. Protocols for producing recombinant viruses and for infecting cells in vitro or in vivo with such viruses can be found in Ausubel, et al., eds., *Gene Therapy Protocols Volume* 1: *Production and In Vivo Applications of Gene Transfer Vectors*, Humana Press, (2008), pp. 1-32 and other standard laboratory manuals. A variety of nucleic acids have been introduced into different cell types using AAV vectors (see for example the references cited above and those cited in Asokan et al., (2012) *Molecular Therapy* 20: 699-708; and Hermonat et al. (1984) *Proc. Natl. Acad. Sci. U.S.A.* 81: 6466-70; Tratschin et al. (1985) *Mol. Cell. Biol.* 4: 2072-81; Wondisford et al. (1988) *Mol. Endocrinol.* 2: 32-39; Tratschin et al. (1984) *J. Virol* 51: 611-9; and Flotte et al. (1993) *J. Biol. Chem.* 268: 3781-90).

Preferably, the RNA-guided programmable nuclease system is specific, i.e., induces genomic alterations preferentially at the target site (i.e., a nucleic acid encoding GPER1 (e.g., a gper1 gene)), and does not induce alterations at other sites, or only rarely induces alterations at other sites.

Anti-GPER1 Antibodies

In some embodiments, the inhibitor of GPER1 is an anti-GPER1 antibody. In some embodiments, the anti-GPER 1 antibody is an antagonist antibody. In some embodiments, the anti-GPER1 antibody disrupts the ability of GPER1 to interact with E2. In some embodiments, the GPER1 antibody interrupts a protein-protein interaction by GPER1. In some embodiments, the anti-GPER1 is a monoclonal antibody. In some embodiments, the GPER1 antibody is a polyclonal antibody. The term "antibody" as used herein refers to an immunoglobulin molecule or an antigen-binding portion thereof. Examples of antigen-binding portions of immunoglobulin molecules include F(ab) and F(ab')$_2$ fragments, which retain the ability to bind antigen. The antibody can be polyclonal, monoclonal, recombinant, chimeric, de-immunized or humanized, fully human, non-human, (e.g., murine), or single chain antibody. In some embodiments the antibody has effector function and can fix complement. In some embodiments, the antibody has reduced or no ability to bind an Fc receptor. For example, the antibody can be an isotype or subtype, fragment or other mutant, which does not support binding to an Fc receptor, e.g., it has a mutagenized or deleted Fc receptor binding region. Methods for making antibodies and fragments thereof are known in the art, see, e.g., Harlow et. al., editors, *Antibodies: A Laboratory Manual* (1988); Goding, *Monoclonal Antibodies: Principles and Practice*, (N.Y. Academic Press 1983); Howard and Kaser, *Making and Using Antibodies: A Practical Handbook* (CRC Press; 1st edition, 2006); Kontermann and Dübel, *Antibody Engineering Volume* 1 (Springer Protocols) (Springer; 2nd ed., 2010); Lo, *Antibody Engineering: Methods and Protocols (Methods in Molecular Biology)* (Humana Press; 2010); and Dübel, *Handbook of Therapeutic Antibodies: Technologies, Emerging Developments and Approved Therapeutics*, (Wiley-VCH; 1 edition, 2010).

Antibodies that bind selectively to GPER1 are known in the art and are commercially available, e.g., from Abbexa Ltd., Abcam, Alomone Labs, Ltd., Thermo Fisher Scientific, LifeSpan BioSciences, Inc., Novus Biologics, OriGene Technologies, and United States Biological.

The anti-GPER1 antibody can be coupled to a detectable or imaging agent. Such agents are well known in the art and include bioluminescent or fluorescent labels (e.g., GFP, FITC, rhodamine, or Texas Red), radioactive isotopes, and colorimetric/enzymatic agents (e.g., horse radish peroxidase (HRP) and B-galactosidase).

Combination Therapy

In some embodiments, the methods include administration of a combination therapy, e.g., comprising administering an inhibitor of GPER1 with one or more of the conventional treatments for liver cancer (see e.g., Longo et al. (2017) *Oncotarget* 8(20): 33897-910; and Cidon (2017) *World J. Hepatol.* 9(18): 797-807, each of which are incorporated herein by reference). Other treatments include, without limitation, surgical resection, radiation therapy, liver transplantation, and treatment with a second therapeutic agent, including chemotherapeutic agents, hormones, irradiating agents, and immunotherapeutics (e.g., pembrolizumab and nivolumab). Chemotherapeutic agents include, but are not limited to, 1-dehydrotestosterone, 5-fluorouracil decarbazine, 6-mercaptopurine, 6-thioguanine, actinomycin D, adriamycin, aldesleukin, alkylating agents, allopurinol sodium, altretamine, amifostine, anastrozole, anthramycin (AMC), anti-mitotic agents, cis-dichlorodiamine platinum (II) (DDP) cisplatin), diamino dichloro platinum, anthracyclines, antibiotics, antimetabolites, asparaginase, BCG live (intravesical), betamethasone sodium phosphate and betamethasone acetate, bicalutamide, bleomycin sulfate, busulfan, calcium leucouorin, calicheamicin, capecitabine, carboplatin, lomustine (CCNU), carmustine (BSNU), chlorambucil, cisplatin, cladribine, colchicin, conjugated estrogens, cyclophosphamide, cyclothosphamide, cytarabine, cytarabine, cytochalasin B, cytoxan, dacarbazine, dactinomycin, dactinomycin, daunirubicin HCl, daunorucbicin citrate, denileukin diftitox, dexrazoxane, dibromomannitol, dihydroxy anthracin dione, docetaxel, dolasetron mesylate, doxorubicin HCl, dronabinol, *E. coli* L-asparaginase, emetine, epoetin-a, *Erwinia* L-asparaginase, esterified estrogens, estradiol, estramustine phosphate sodium, ethidium bromide, ethinyl estradiol, etidronate, etoposide citrororum factor, etoposide phosphate, filgrastim, floxuridine, fluconazole, fludarabine phosphate, fluorouracil, flutamide, folinic acid, gemcitabine HCl, glucocorticoids, goserelin acetate, gramicidin D, granisetron HCl, hydroxyurea, idarubicin HCl, ifosfamide, interferon a-2b, irinotecan HCl, letrozole, leucovorin calcium, leuprolide acetate, levamisole HCl, lidocaine, lomustine, maytansinoid, mechlorethamine HCl, medroxyprogesterone acetate, megestrol acetate, melphalan HCl, mercaptipurine, mesna, methotrexate, methyltestosterone, mithramycin, mitomycin C, mitotane, mitoxantrone, nilutamide, octreotide acetate, ondansetron HCl, oxaliplatin, paclitaxel, pamidronate disodium, pentostatin, pilocarpine HCl, plimycin, polifeprosan 20 with carmustine implant, porfimer sodium, procaine, procarbazine HCl, propranolol, regorafenib, rituximab, sargramostim, sorafenib, streptozotocin, tamoxifen, taxol, tegafur, teniposide, tenoposide, testolactone, tetracaine, thiotepa chlorambucil, thioguanine, thiotepa, topotecan HCl, toremifene citrate, trastuzumab, tretinoin, valrubicin, vinblastine sulfate, vincristine sulfate, and vinorelbine tartrate. Standard dosing regimens of chemotherapeutic agents used for the treatment of patients having liver cancer are known in the art and may be used in the methods described herein.

The following examples are included to demonstrate preferred embodiments of the invention. It should be appreciated by those of skill in the art that the techniques disclosed in the examples that follow represent techniques discovered by the inventors to function well in the practice of the invention. Those of skill in the art should, however, in light of the present disclosure, appreciate that many changes can be made in the specific embodiments that are disclosed and still obtain a like or similar result without departing from the spirit and scope of the invention, there-

EXAMPLES

The invention is further described in the following examples, which do not limit the scope of the invention described in the claims.

Example 1: GPER1 is the Estrogen Sensor Activating Signaling that Promotes Liver Growth and Cancer This study shows that E2 induces cell cycle progression and increases hepatocyte proliferation and liver size in larval zebrafish. Surprisingly, these effects are not mediated through the classic nuclear hormone estrogen receptors, but via GPER1 and downstream activation of PI3K/mTOR signaling. Importantly, GPER1 similarly promotes sex-specific adult liver growth, and together with mTOR, is required for optimal liver regrowth after injury. In addition, GPER1 directly modulates propensity for liver cancer formation: gper1$^{-/-}$ mutant fish develop significantly fewer and smaller liver tumors than wild-type siblings. The role of GPER1 is conserved in the human liver, as liver cancer tissue expresses increased GPER1, and primary human hepatocytes proliferate in response to E2. Chemical inhibition or genetic loss of GPER1 in vivo significantly diminishes E2-induced tumor progression after chemical carcinogenesis, particularly in males. Thus, GPER1 appears to act by sensing E2 to regulate PI3K/mTOR activity and proliferative responses during hepatic development and repair, and is an important therapeutic target for liver cancer prevention and treatment.

Materials and Methods

The following materials and methods were used in this Example.

Zebrafish Husbandry

Tu zebrafish, Tg(−2.8fabp10a:eGFP)$^{as3}$, abbreviated fabp10a:GFP, Tg(fabp10a:CFP-NTR)[12], and mtor mutants (xu015Gt) were maintained according to Institutional Animal Care and Use Committee guidelines (IACUC) at Harvard Medical School.

Chemical Exposures

Zebrafish larvae were exposed to chemicals, dissolved in 0.1% (v/v) dimethylsulfoxide (DMSO), at specified doses for 5 hrs. from 110-115 hours post fertilization (hpf) and analyzed at 120 hpf (unless otherwise specified). Adults were treated for 5-7 hrs. per exposure with frequency as described. Chemicals are listed in Table 1, below.

TABLE 1

Chemicals used in experimental procedures

| Chemical | Concentration | Supplier, Catalog Number |
| --- | --- | --- |
| β-Estradiol | 10 μM | Tocris, 2824 |
| MPP dihydrochloride | 80 μM | Tocris, 1991 |
| PHTPP | 8 μM | Tocris, 2662 |
| G-15 | 60 μM (embryo) | Tocris, 3678 |
|  | 10 μM (adult) |  |
| G-1 | 8 μM | Tocris, 3577 |
| Anastrozole | 10 μM | Tocris, 3388 |
| 740 Y-P | 2 μM | Tocris, 1983 |
| Rapamycin | 1 μM | Tocris, 1292 |
| LY294002 HCl | 15 μM | Tocris, 1130 |
| NSC 228155 | 5 μM | Calbiochem, 530536 |
| Erlotinib HCl | 10 μM | Selleckchem, S1023 |
| MK-2206 2HCl | 5 μM | Selleckchem, S1078 |
| Metronidazole | 10 μM | Sigma, M3761 |

Morpholino Injection

ATG morpholino oligonucleotides (MO) designed against esr1, esr2a, esr2b,[13] gper1, and mtor (GeneTools, Table 2) as well as mismatched controls were injected into one-cell stage Tu embryos.

TABLE 2

Morpholino oligonucleotides used in experimental procedures

| Gene | Sequence (5'-3') | Type | Amount Injected (ng) |
| --- | --- | --- | --- |
| esr1 | AGGAAGGTTCCTCCAGGGCTTCTCT (SEQ ID NO: 5) | ATG | 2 |
| esr2a | ACATGGTGAAGGCGGATGAGTTCAG (SEQ ID NO: 6) | ATG | 2 |
| esr2b | AGCTCATGCTGGAGAACACAAGAGA (SEQ ID NO: 7) | ATG | 2 |
| gper1 | ACATTGGTAGTCTGCTCCTCCATGC (SEQ ID NO: 8) | ATG | 2 |
| gper1 | GCTGCAACACCTGTTATAAGAGAAA (SEQ ID NO: 9) | Splice | 2 |
| mtor | GGTTTGACACATTACCCTGAGCATG (SEQ ID NO: 10) | ATG | 2 |
| control | CCTCTTACCTCAGTTACAATTTATA (SEQ ID NO: 11) |  | 2 | mRNA Injection

Human GPER1 cDNA-containing plasmid was obtained from Dana-Farber/Harvard Cancer Center (HsCD0032896) and transcribed using the mMESSAGE mMACHINE Transcription Kit (Ambion). mRNA (200 μg) was injected into one-cell stage embryos.

Generation of gper1 Mutants

TALENs targeting gper1 were obtained from Addgene (TAL3272, TAL3273).[14] mRNAs of TALEN pairs were synthesized using the mMESSAGE mMACHINE kit and injected into one-cell stage embryos. Adult TALEN-injected fish (F$_0$) were out-crossed to WT siblings, and progeny (F$_1$) screened for somatic mutations by Sanger sequencing (primers listed in Table 3 below). $F_1$ mutants were raised and out-crossed for at least 4 generations to avoid possible off-target effects.

transferase dUTP nick-end labeling (TUNEL) staining were performed using established protocols.[16] GPER1 staining was scored by a pathologist based on the mean amount of

TABLE 3

PCR Primers

| Gene | Forward Primer (5'-3') | Reverse Primer (5'-3') | LTR (5'-3') |
|---|---|---|---|
| gper1 | TCAAGTTGCCGTCACAATGC (SEQ ID NO: 12) | GTCATCCTCTCCTGTGGTT (SEQ ID NO: 13) | |
| ef1a | GCGTCATCAAGAGCGTTGAG (SEQ ID NO: 14) | TTGGAACGGTGTGATTGAGG (SEQ ID NO: 15) | |
| mtor | ATAAGAAAAGAAACCACATGTCATACC (SEQ ID NO: 16) | CTTACCACTCAGAGAGACCAAAG (SEQ ID NO: 17) | CCCTAAGTACTTGTACTTTCACTTG (SEQ ID NO: 18) |

Western Blot Analysis

Pooled larvae (n=30-40) and cultured cells were homogenized in radioimmunoprecipitation assay (RIPA) lysis buffer and processed as previously described.[15] Lysates were separated by gel electrophoresis and subjected to Western blot. Antibodies are listed in Table 4 below.

TABLE 4

Antibodies used in experimental procedures

| Antibody | Application | Concentration | Supplier, Catalog Number |
|---|---|---|---|
| α - PCNA | IHC | 1:200 | Anaspec, AS-55421 |
| α - Pan-Cadherin | IF | 1:1000 | Sigma, C3678 |
| α - BrdU | Whole-mount IHC | 1:500 | Sigma, B2531 |
| α - pEGFR (Tyr1173) | WB | 1:1000 | Milipore, 05-483 |
| α - Akt | WB | 1:1000 | Cell Signaling, 9272 |
| α - pAKT(Ser473) | WB Whole-mount IHC | 1:1000 1:200 | Cell Signaling, 4060 |
| α - mTOR | WB | 1:1000 | Cell Signaling, 2983 |
| α - S6 | WB | 1:1000 | Cell Signaling, 2217 |
| α - pS6(Ser240/244) | WB Whole-mount IHC | 1:1000 1:200 | Cell Signaling, 2215 |
| α - β-actin | WB | 1:5000 | Cell Signaling, 4970 |
| α - Rabbit (Alexa Fluor® 647) | IF | 1:500 | Abcam, ab150075 |
| α - Rabbit IgG-HRP | IHC, WB | 1:1000 | Santa Cruz, sc-2004 |
| α - GPER1 | IHC | 1:50 | Sigma, HPA027052 |
| α - HNF4α | IF | 1:50 | Abcam, ab55223 |
| α - Mouse (Alexa Fluor® 488) | IF | 1:500 | Jackson Immuno Labs |

Whole Mount in situ Hybridization

Larvae were fixed with paraformaldehyde and in situ hybridization (ISH) performed according to standard protocols.[16] gper1 probe was generously gifted by David Volz.[17]

Liver Size Analysis

ISH images were obtained by brightfield microscopy, and fabp10a:GFP reporter larvae were imaged using fluorescence microscopy. 3D imaging of fabp10a:GFP fish was performed with a Zeiss LightsheetZ.1. Image quantification was achieved using IZebrafish were fixed and paraffin embedded. Tissues were sectioned (5 μm) and stained with hematoxylin & eosin (H&E). De-identified formalin-fixed paraffin-embedded human liver sections were obtained from pathology files of the University of Utah (IRB 00091019) and commercially available tissue arrays (OD-CT-DgLiv01-003, US Biomax). Immunohistochemistry (IHC) (using antibodies listed in Table 4) and terminal deoxynucleotidyl cytoplasmic reactivity in hepatic cells: 0+, minimal/no staining; 1+, faint/mild staining; 2+, moderate staining; 3+, strong staining.

Flow Cytometry and Cell Cycle Analysis fabp10a:GFP larvae were processed for fluorescence-activated cell sorting (FACS) analysis as previously described.[16] For cell cycle analysis, dissociated cells were processed using the BrdU Flow kit (BD Bioscience, 559619) and incubated in propidium iodide (PI), and subsequently analyzed using flow cytometry. Analysis was performed with FlowJo v10.0.7 software.

qRT-PCR Analysis

RNA was isolated from zebrafish larvae and processed as previously described.[18] qRT-PCR was performed to determine relative gene expression levels using the ΔΔCt method with ef1α as reference gene. Primer are listed in Table 5 below.

TABLE 5

RT-PCR primers

| Gene | Forward Primer (5'-3') | Reverse Primer (5'-3') |
|---|---|---|
| gper1 | CTCGTGAATAAAGTGTTGCAG (SEQ ID NO: 19) | GCAGTCTTGTTTCCTCCAG (SEQ ID NO: 20) |

Chemical Carcinogenesis gper1$^{-/-}$ or wild-type fry were exposed to 5 ppm dimethylbenzanthrazene (DMBA) for 24 hrs. at 3, 4, and 5 weeks.[19] Fish recovered for 1 week prior to longitudinal chemical exposures commencing at 6 weeks (3 times/week). Fish were monitored daily for survival and tumor formation until 33 weeks post DMBA treatment. Fish were either analyzed immediately after death or at 33 weeks post DMBA exposure, when all remaining fish were sacrificed. Histologic analysis was performed by a board-certified pathologist with expertise in zebrafish liver histology in a blinded fashion.

Steady-State Metabolomics Analysis

Adult livers were surgically removed and subjected to methanol extraction as previously described.[18,20] Polar metabolites were identified using LC-MS/MS. Metabolic pathway analysis was performed with MetaboAnalyst.

Transcriptomic Analysis

RNA was extracted from resected livers and processed as previously described.[18] polyA sequences were aligned onto the ZV9 genomic assembly, and differentially expressed genes were determined using TopHat and Cufflinks pipelines. Gene Ontology (GO) terms were analyzed using DAVID (NIAID, NIH).

Primary Human Hepatocyte Culture and Cell Culture Experiments 96-well glass bottom plates (Greiner Bio-one) were incubated with type I collagen solubilized in water (100 µg/ml; BD Biosciences) for 1 h at 37° C. A J2-3T3 fibroblast feeder layer (gift from H. Green) was plated onto collagen at a density of 16,000 cells/well at day −1. Primary human hepatocytes (Hu4175:3-yr old male donor, Invitrogen) were plated onto fibroblasts on day 0 at a density of 4,000 cells/well and maintained under standard culture conditions with daily replacement of hepatocyte medium (1×DMEM/F12 (phenol red free), 10% fetal bovine serum (FBS), 15.6 ug/ml insulin, 7.5 µg/ml, hydrocortisone, 16 ng/ml glucagon, 1% penicillin-streptomycin). From day 6, FBS concentration of the hepatocyte medium was lowered to 2% and DMSO concentration was set at 0.1%. From day 7-10, cells were pulsed daily with E2 for 5.5 hrs/day, followed by 18.5 hrs. culture in hepatocyte medium with 10 µM EdU. On day 11, cells were fixed in 4% PFA and stained with Click-iT EdU Alexa Fluor 594 Imaging Kit (Thermo Fisher), with additional antibody staining for HNF4α(ab55223) and goat-anti-mouse 488 (Jackson Immunolabs). Nuclei were visualized with Hoechst stain (Invitrogen). Cells were imaged and analyzed in MS-Elements Viewer 4.0, ImageJ, and Photoshop.

Cell Culture

HepG2 cells (Sigma-Aldrich, USA) were cultured in phenol-red free, Minimum Essential Medium Eagle (MEM) supplemented with 10% heat-inactivated fetal bovine serum (Hyclone, Thermo Scientific, USA), L-glutamine (2 mM), 1% non-essential amino acids and penicillin-streptomycin (10,000 U/mL), at 37° C. and 5% CO2. Following 24 hrs of serum starvation, HepG2 cells were incubated with DMSO or G15 (500 nM) for 20 min prior to exposure to E2 (10 nM), or E2+G15 for 30 min.

Results

Estrogen Enhances Liver Growth

Figure 1B:
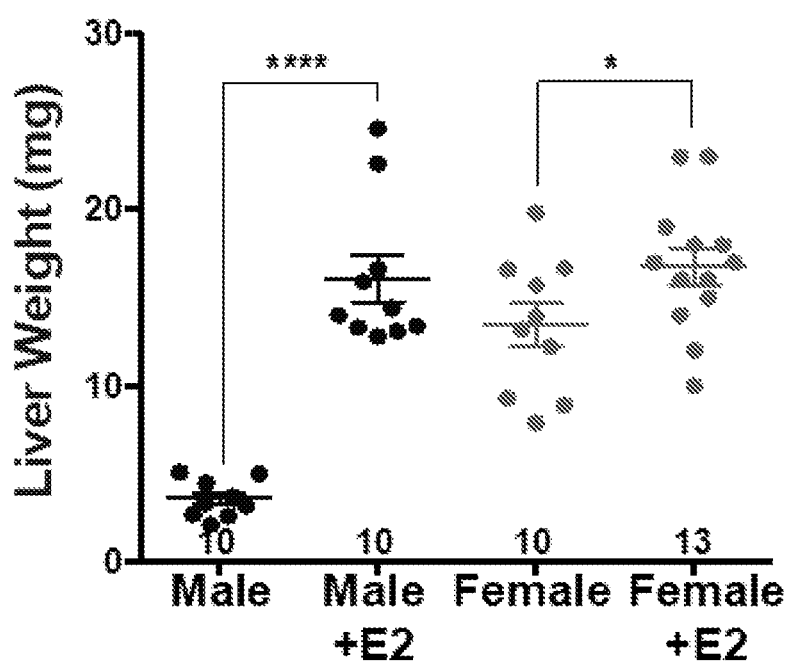
Figure 1C:
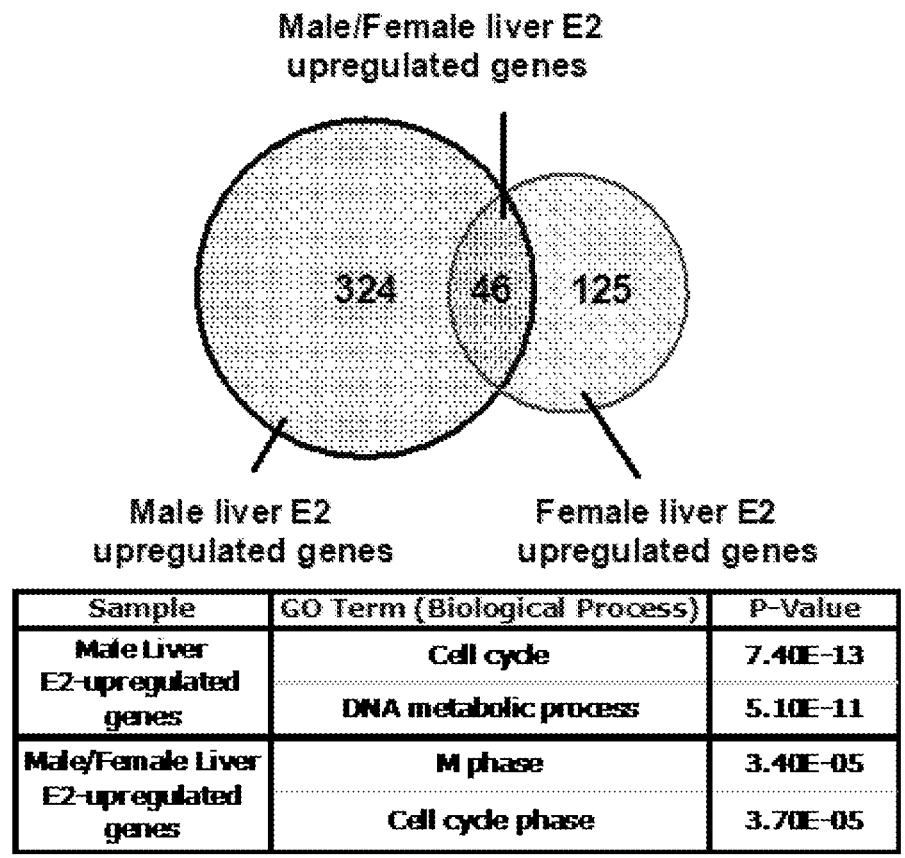

Adult female zebrafish exhibit increased liver size compared to males, as visualized in transgenic hepatocyte reporter fish expressing GFP regulated by the fatty acid binding protein 10a promoter, Tg (fabp10a:GFP) (FIG. 1A). To establish baseline liver weights, adult livers were dissected and measured in 10 wild-type (WT) males and females at 7 months of age, revealing a significant 3.7-fold difference (FIG. 1B). To examine the potential impact of estrogen on liver growth, zebrafish were exposed daily to E2 (10 µM) or DMSO vehicle control for six weeks, and liver size and weight were assessed (FIGS. 1A and 1B). Male livers were smaller than female livers at baseline, but responded more significantly to E2 with a 4.5-fold increase in weight, while females exhibited a 1.2-fold enhancement (FIG. 1B). These results indicate that liver mass is directly responsive to estrogenic stimulation.

Figure 1D:
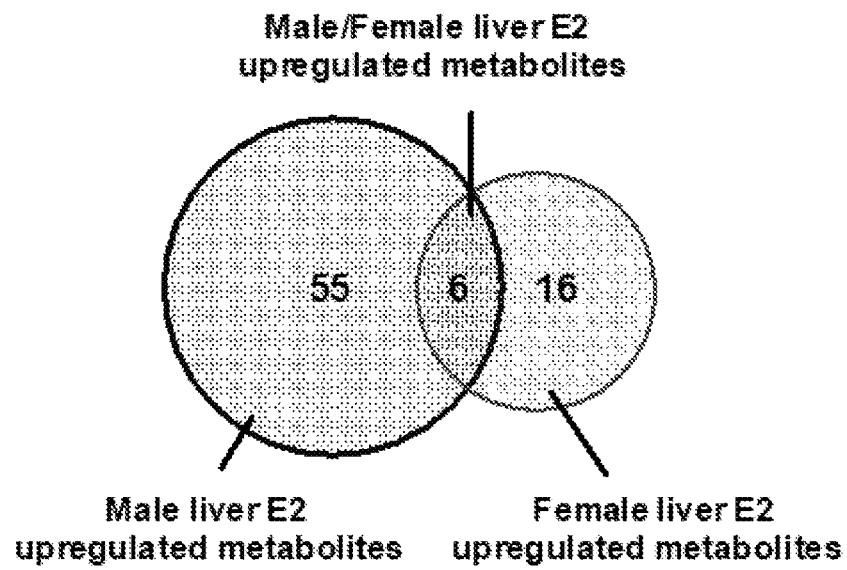
Figures 8A, 8B, 8C:
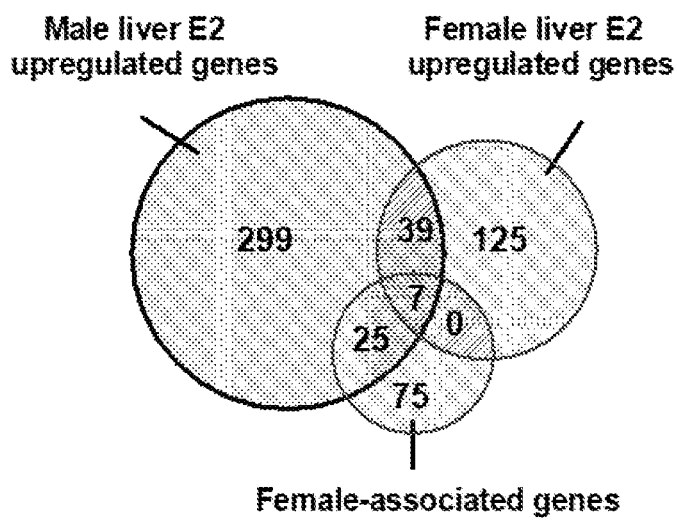
FIGS. 8A-8C shows that estrogen increases liver growth and size.

To uncover the signals mediating the effect of E2 on liver size, transcriptome analysis was performed on male and female livers in the presence or absence of E2. Interestingly, gene expression in male and female livers was different, with a subset of genes identified as "female-associated", indicating genes up-regulated in females (FIG. 8). These differences, however, are not solely due to estrogenic effects, as E2 did not simply convert the transcriptome of male livers into that of females: in fact, E2 exposure altered the transcriptional profiles in both sexes (FIG. 8). In particular, gene ontology analysis revealed that E2 exposure enhanced cell cycle-related gene expression in both sexes (46 genes, $p=3.4\times10^{-5}$), particularly in male livers (324 genes, $p=7.4\times10^{-13}$). Given that the liver is the primary metabolic organ, we examined whether sex and/or E2-associated increase in liver mass correlated with functional metabolic alterations, employing steady-state metabolomics profiling (FIGS. 1D and 8C). Significantly, metabolite set enrichment analysis revealed E2 exposure altered the metabolome in male livers to affect pyrimidine and purine metabolism, which is essential for DNA synthesis and cell proliferation (FIG. 1D; 55 metabolites; pyrimidine, $p=1.9\times10^{-8}$; purine, $p=3.5\times10^{-3}$).[18] Together, these findings indicate that metabolic sex-dimorphisms in the adult liver may be associated with E2 levels.

Figure 1E:
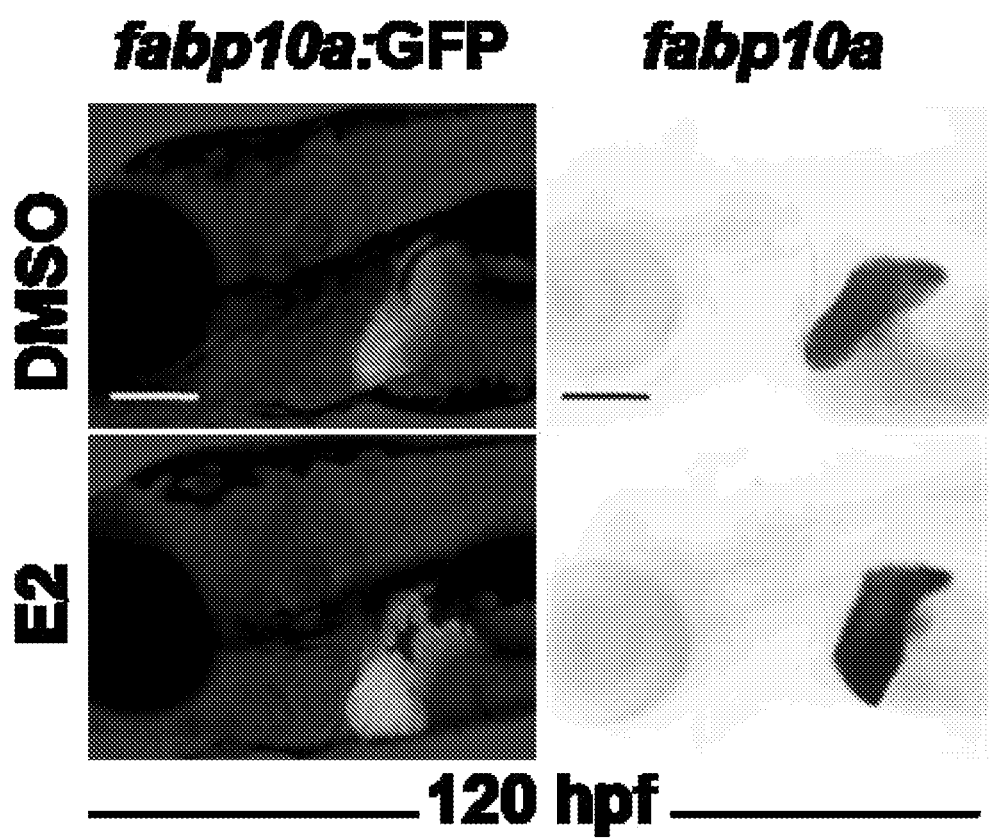
Figure 1F:
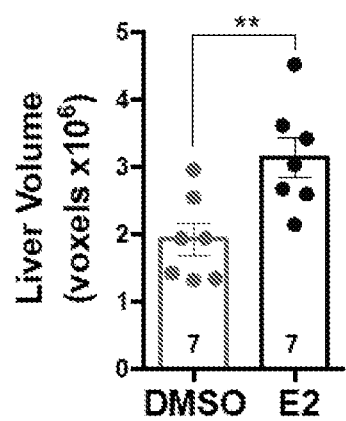
Figure 1G:
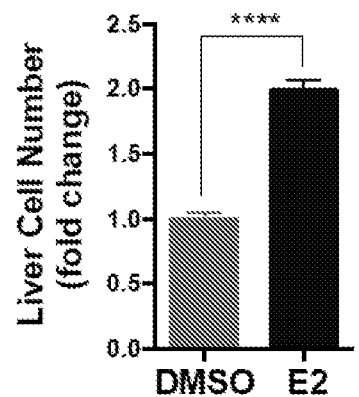
Figure 1H:
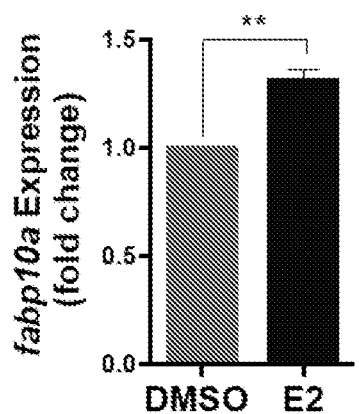
Figure 1I:
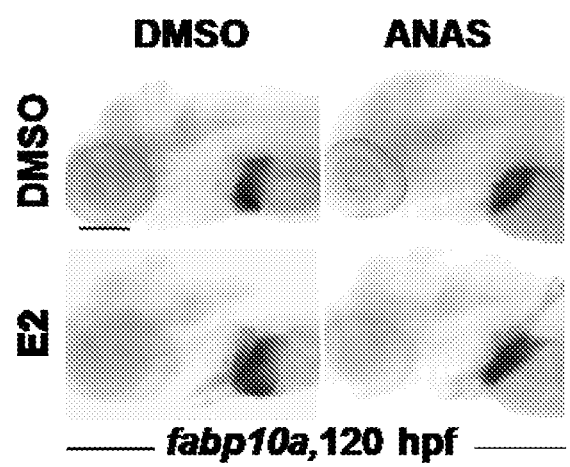
Figure 1J:
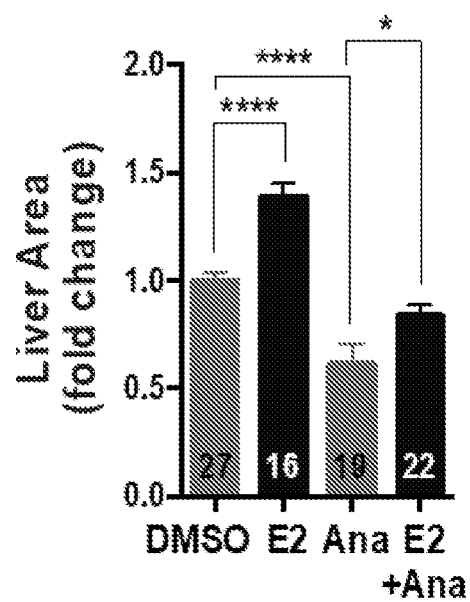

To directly investigate the effect of E2 on hepatocytes, without the influence of pre-existing sex differences, livers of zebrafish larvae were examined before sexual dimorphic features have developed. Larvae were exposed to E2 for select 5 hour intervals after hepatocytes were fully differentiated (>95 hpf). E2 increased liver size at 120 hpf as analyzed by ISH for the hepatocyte marker fabp10a; this effect was confirmed by fluorescent imaging of hepatocyte reporters (Tg(fabp10a:GFP)) and qRT-PCR (FIGS. 1E and 1F; p<0.01). The effect of E2 on liver growth was further characterized as an enhancement in liver volume, using Lightsheet microscopy (FIG. 1G; p<0.01), and total hepatocyte number, as quantified by FACS (FIG. 1H; p<0.0001). To determine the impact of endogenous E2 on liver growth, larvae were exposed to the aromatase inhibitor anastrozole (ANAS), which inhibits E2 production, revealing a decrease in liver size by ISH quantification (FIGS. 1I and 1J). These results demonstrate that during larval stages, independent of sex-associated influences, E2 signaling regulates hepatocyte number and liver growth.

Estrogen Increases Liver Size Via Activation of GPER1

Figure 2A:
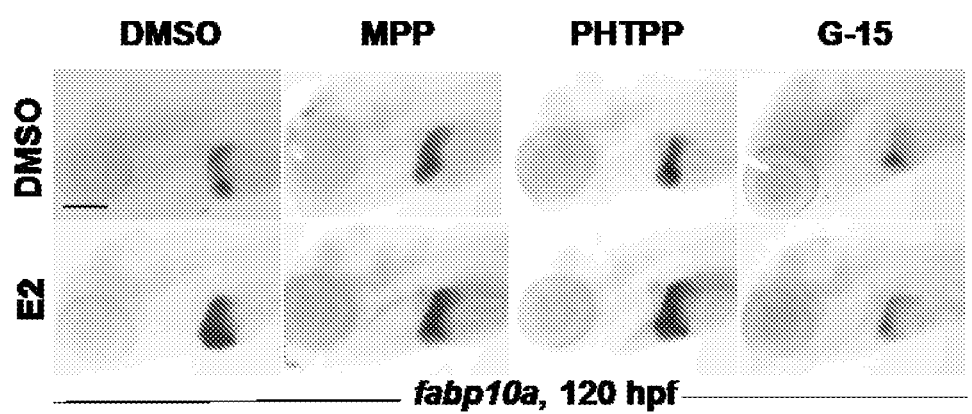
FIGS. 2A-2H show that G protein-coupled estrogen receptor 1 (GPER1) mediates the estrogenic effects on liver growth.
Figure 2B:
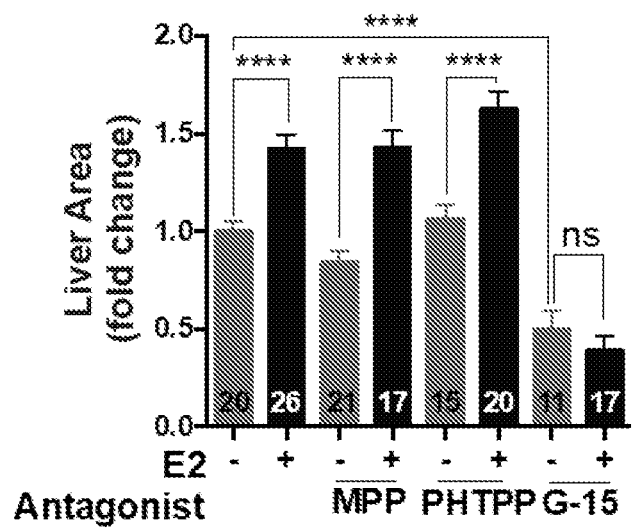
Figure 2C:
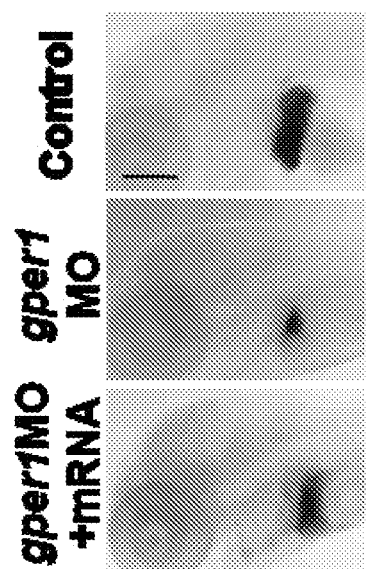
Figure 2D:
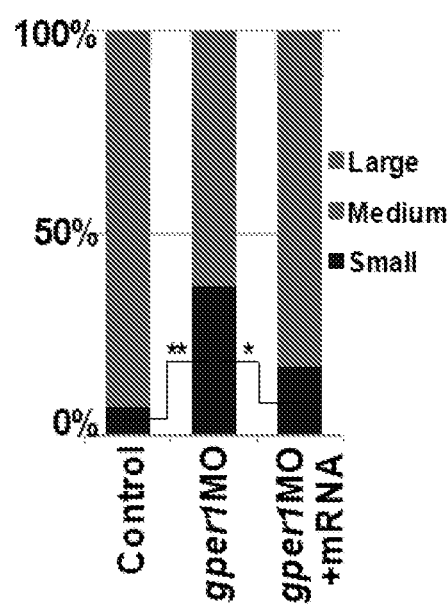
Figure 9A:
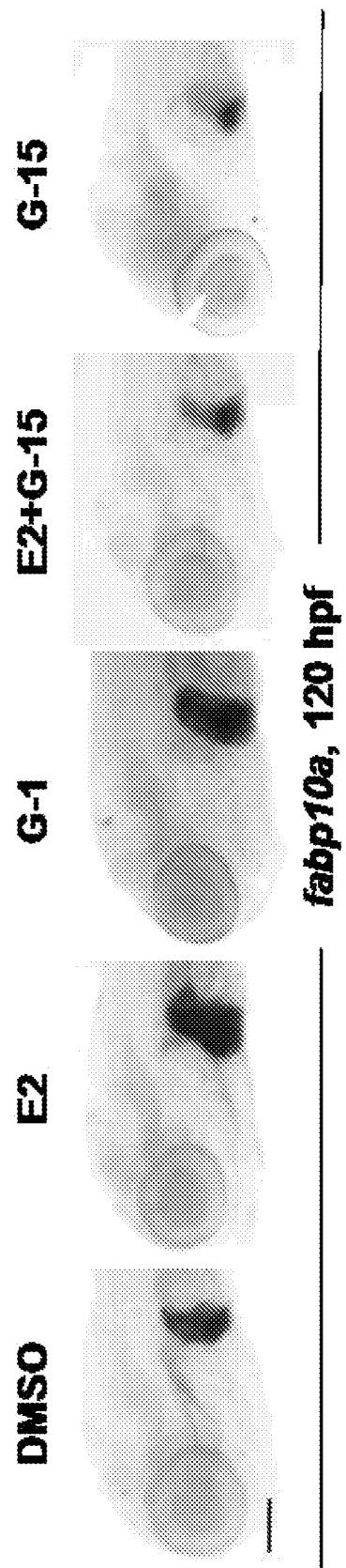
FIGS. 9A-9F shows that G protein-coupled estrogen receptor 1 (GPER1) mediates the estrogenic effects on liver growth.
Figure 9B:
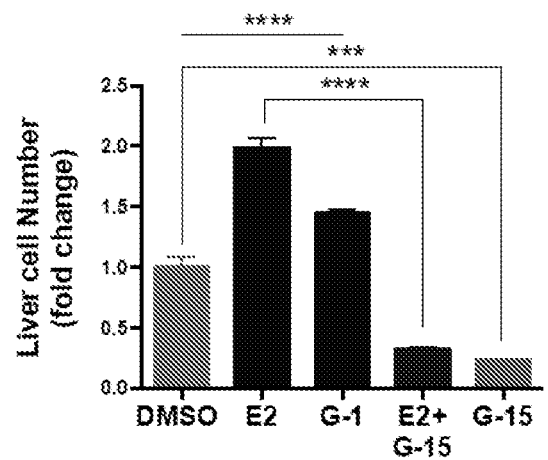
Figure 9C:
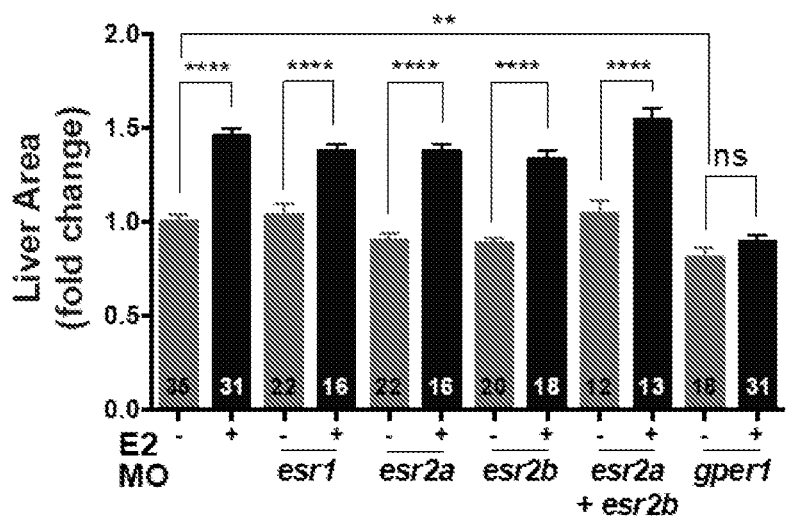
Figure 9D:
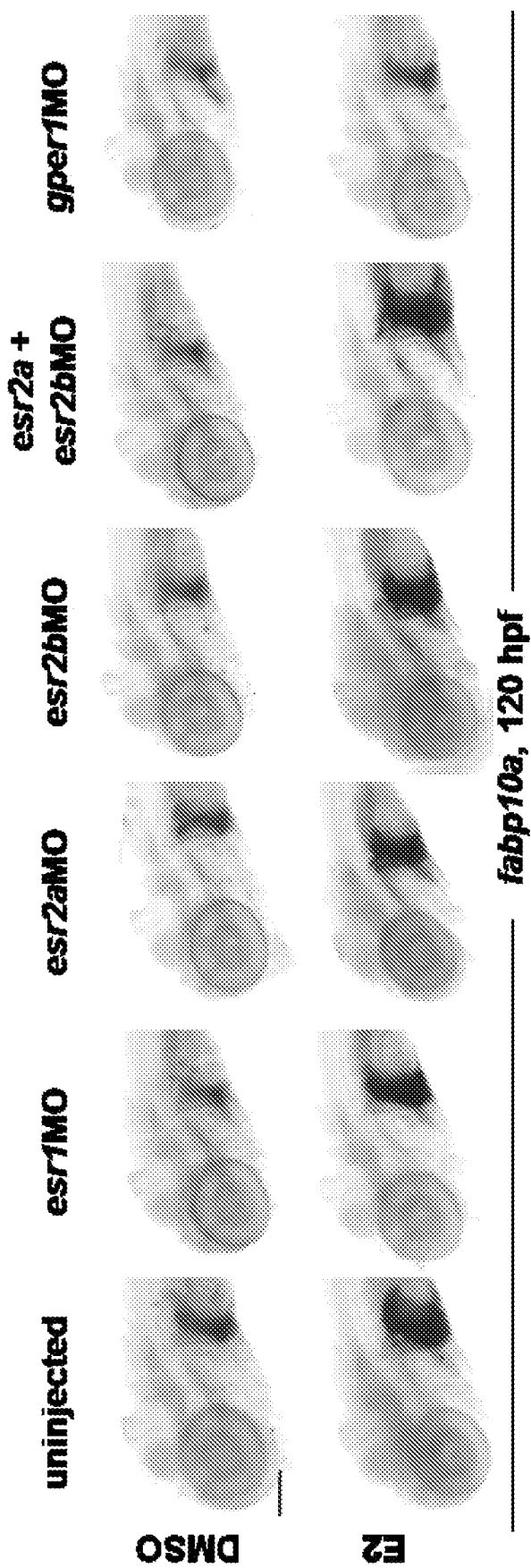
Figure 9E:
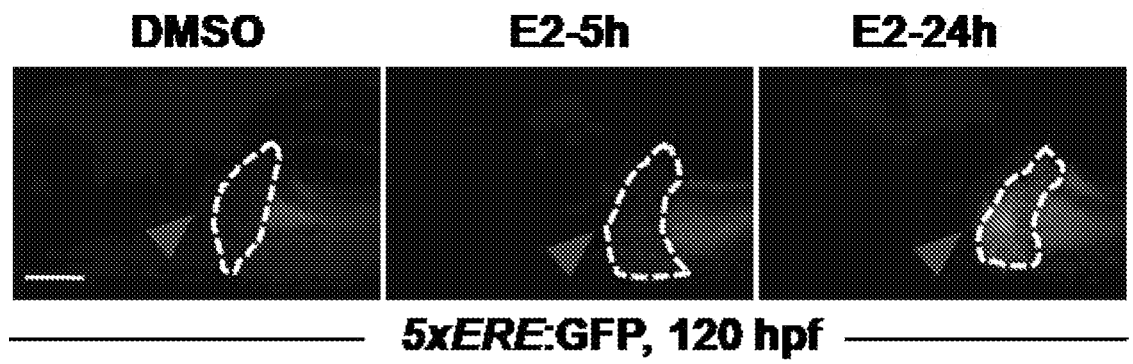
Figure 9F:
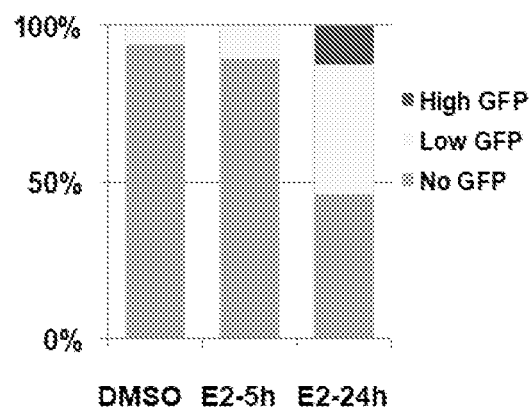
Figure 10A:
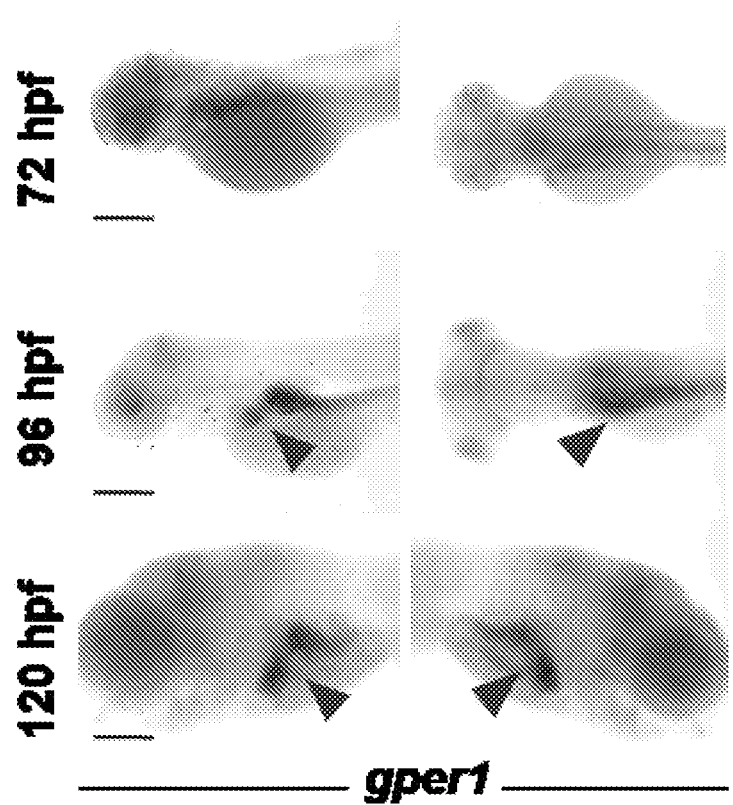
FIGS. 10A-10G show that GPER1 mediates the estrogenic effects on liver growth.
Figure 10B:
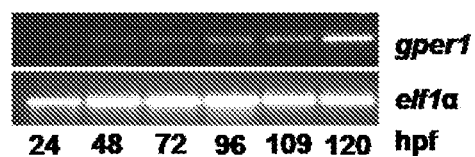
Figure 10C:
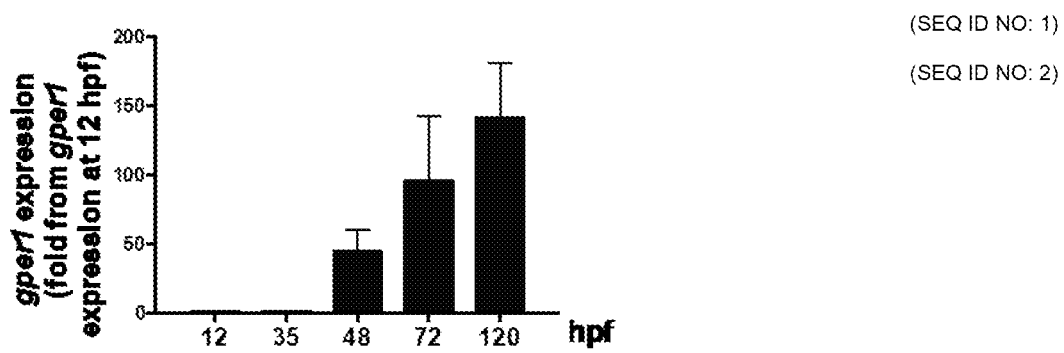

To identify the receptor mediating the effect of E2 on the regulation of liver growth, larvae were exposed to selective chemical antagonists for each estrogen receptor, MPP (ESR1), PHTPP (ESR2) and G-15 (GPER1), alone or in combination with E2. Significantly, as quantified by fabp10a expression, the E2-induced enhancement in liver size was specifically inhibited by co-exposure with G-15, but not by blockade of ESR1 or ESR2 (FIGS. 2A and 2B). Selective GPER1 activation with G-1 increased liver size and hepatocyte number, similarly to E2, while GPER1 inhibition with G-15 caused reduced liver size (FIGS. 9A and 9B). Furthermore, MO-mediated knockdown of gper1, but not nuclear estrogen receptors esr1, esr2a, esr2b, or esr2a+esr2b blocked the effect of E2 on liver growth, confirming specificity of chemical modifiers (FIGS. 9C and 9D). Importantly, injection of human GPER1 mRNA into gper1 morphants partially rescued the small liver phenotype, demonstrating both specificity and evolutionary conservation (FIGS. 2C and 2D). To confirm that hepatic nuclear hormone receptor-mediated genomic signaling was not activated following E2 exposure, estrogen response element (ERE) reporter fish Tg(5×ERE:GFP) were imaged to reflect DNA binding by nuclear hormone receptors.[21] Fluorescence imaging at 120 hpf indicated that E2 (110-115 hpf) had minimal effect on baseline hepatic Esr signaling during this developmental period (FIGS. 9E and 9F). Intriguingly, gper1 expression is dynamically regulated during development: ISH directly localized gper1 expression to the liver (FIG. 10A), and RT-PCR analysis indicated increasing expression from 48 hpf, when the earliest differentiated hepatocytes are observed, until 120 hpf, correlating with hepatic outgrowth (FIGS. 10B and 10C). Together, these data indicate that GPER1 is essential for E2-mediated liver growth during development.

Figure 2E:
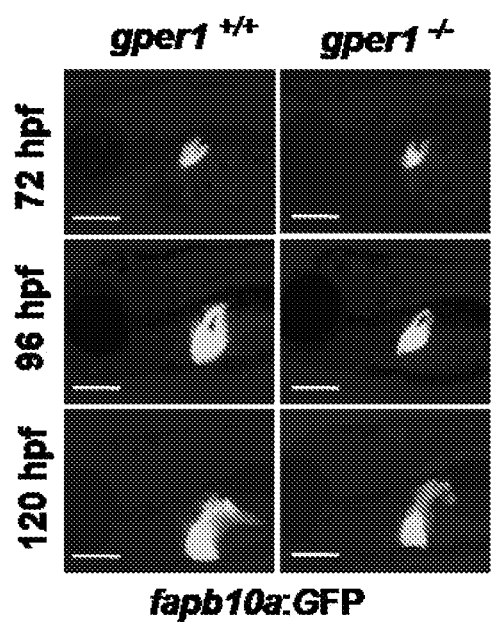
Figure 2F:
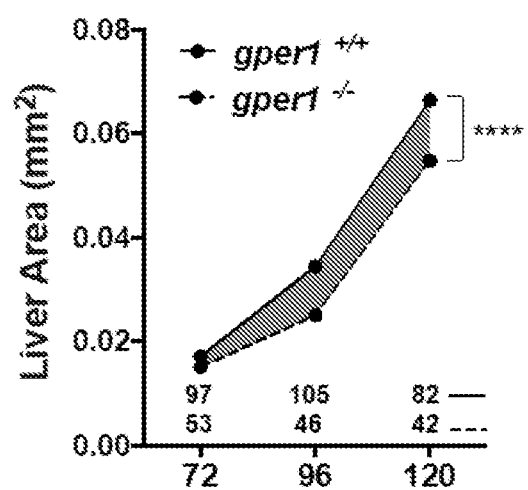
Figure 2G:
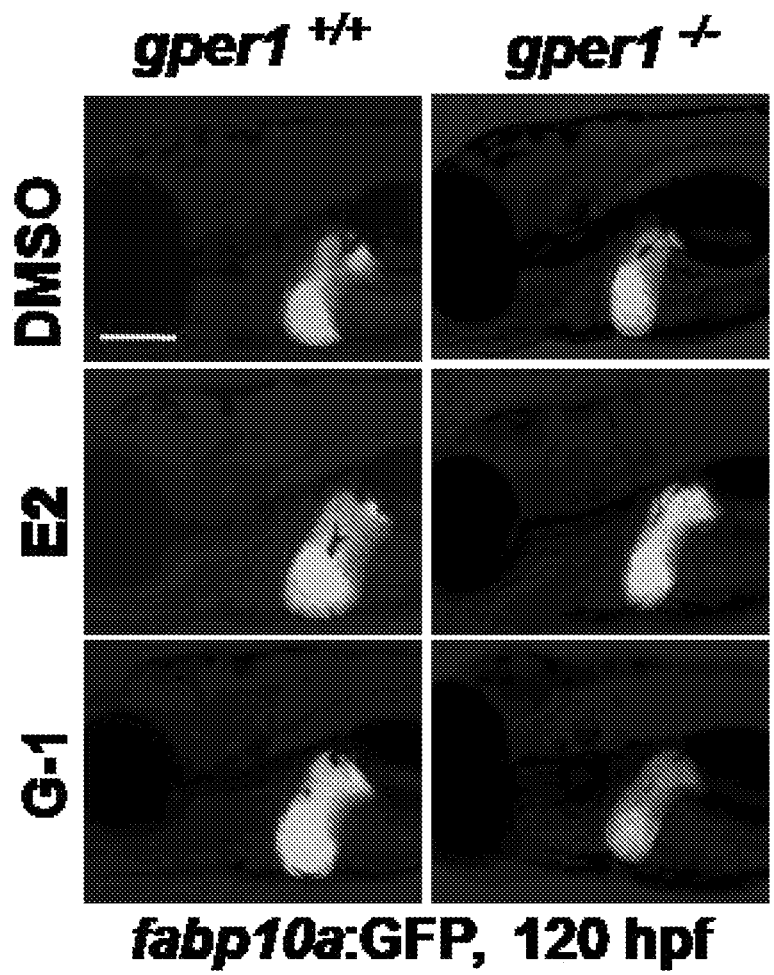
Figure 2H:
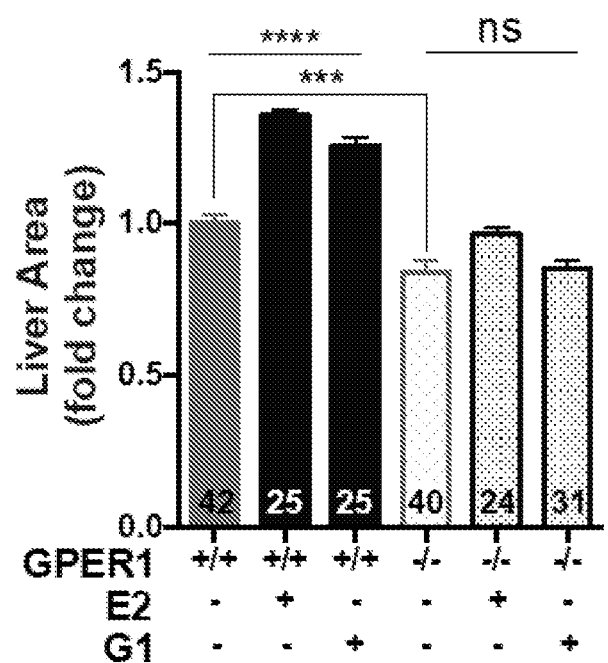
Figure 10D:
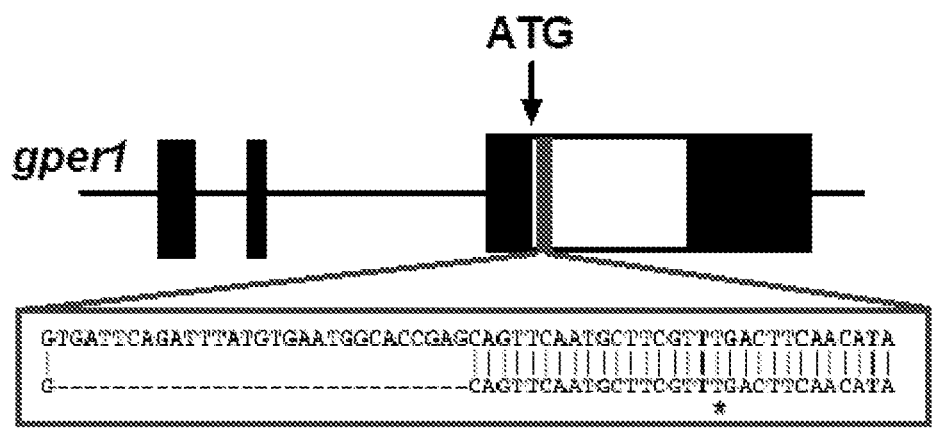
Figure 10E:
Figure 10F:
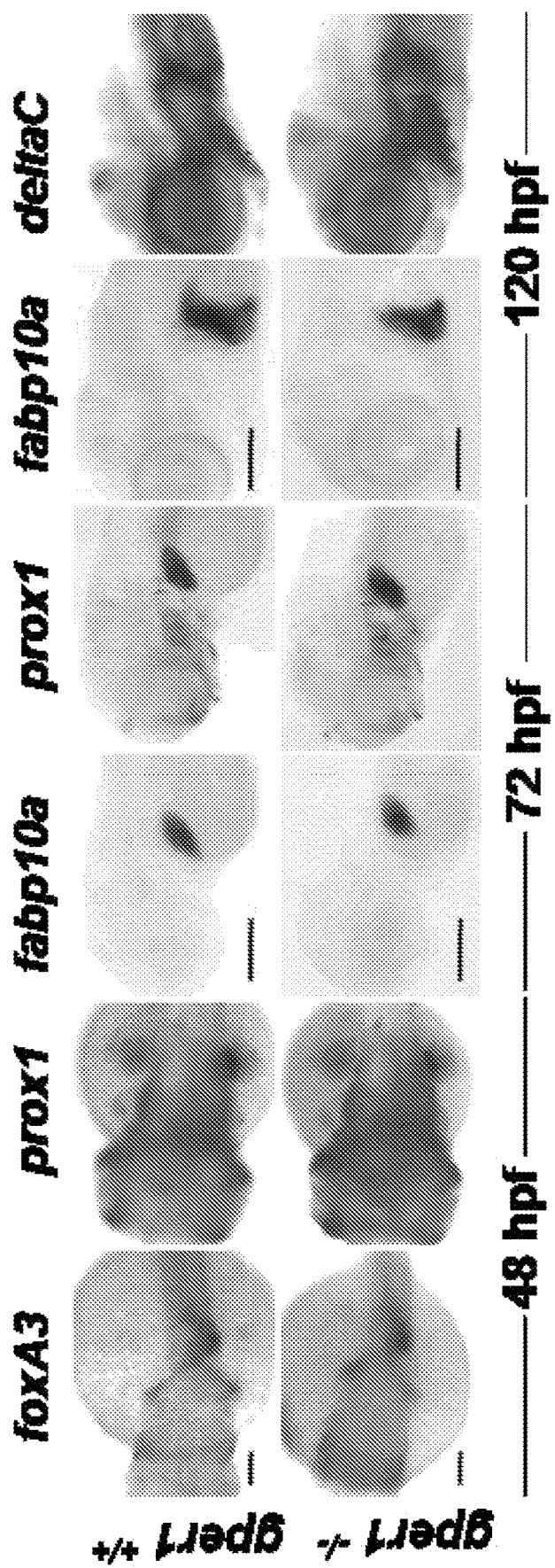
Figure 10G:
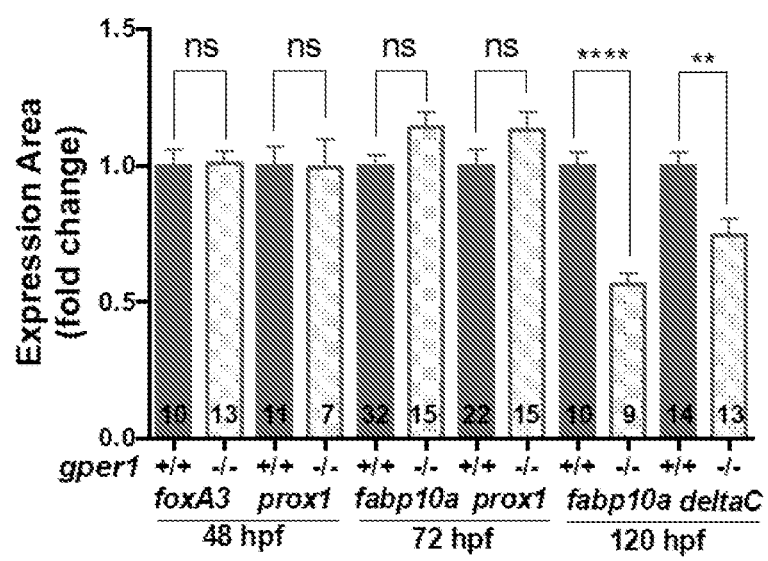

To definitively demonstrate the role of GPER1 in mediating E2 effects on larval and adult liver growth, gper1 mutant zebrafish were generated using TALENs: a 29-base pair deletion in exon one resulted in a premature stop codon (FIG. 10D) and disrupted GPER1 protein production (FIG. 10E). GPER1 loss, assessed in the Tg(fabp10a:GFP) reporter background, impaired liver growth after 96 hpf, but not earlier, supporting a requirement for E2/GPER1 in the outgrowth of differentiated hepatocytes (FIGS. 2E and 2F). Consistent with these findings, expression of hepatic progenitor markers, foxA3 and prox1, was not affected in gper1$^{-/-}$ larvae at 48 hpf or 72 hpf (FIGS. 10F and 10G). Significantly, as compared to WT livers, gper1$^{-/-}$ mutants did not respond to E2 or G-1 exposure (FIGS. 2G and 2H), definitively demonstrating that E2 signals via GPER1 to increase liver size.

Figure 3A:
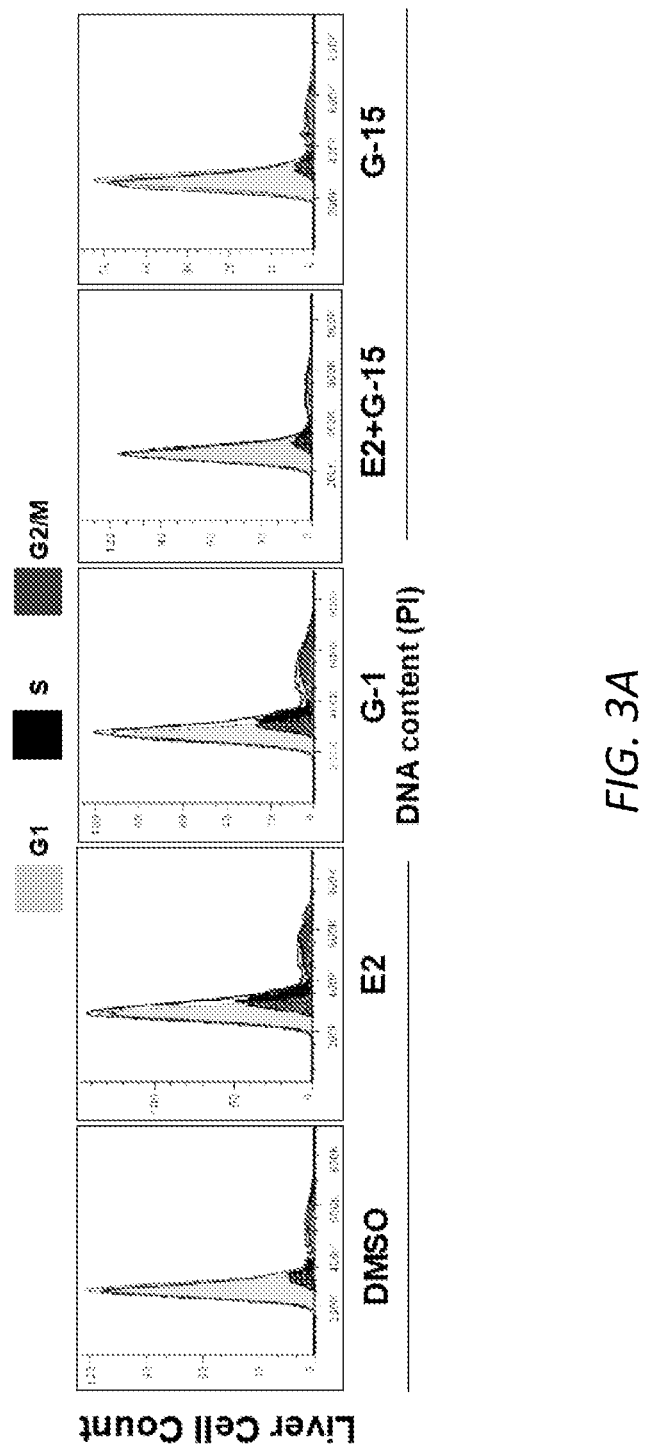
Figure 3D:
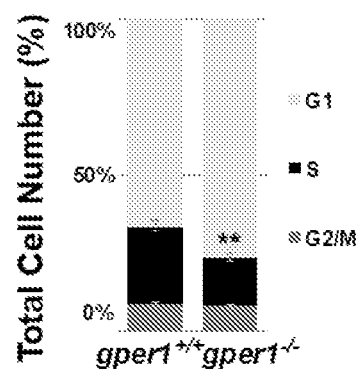
Figure 3E:
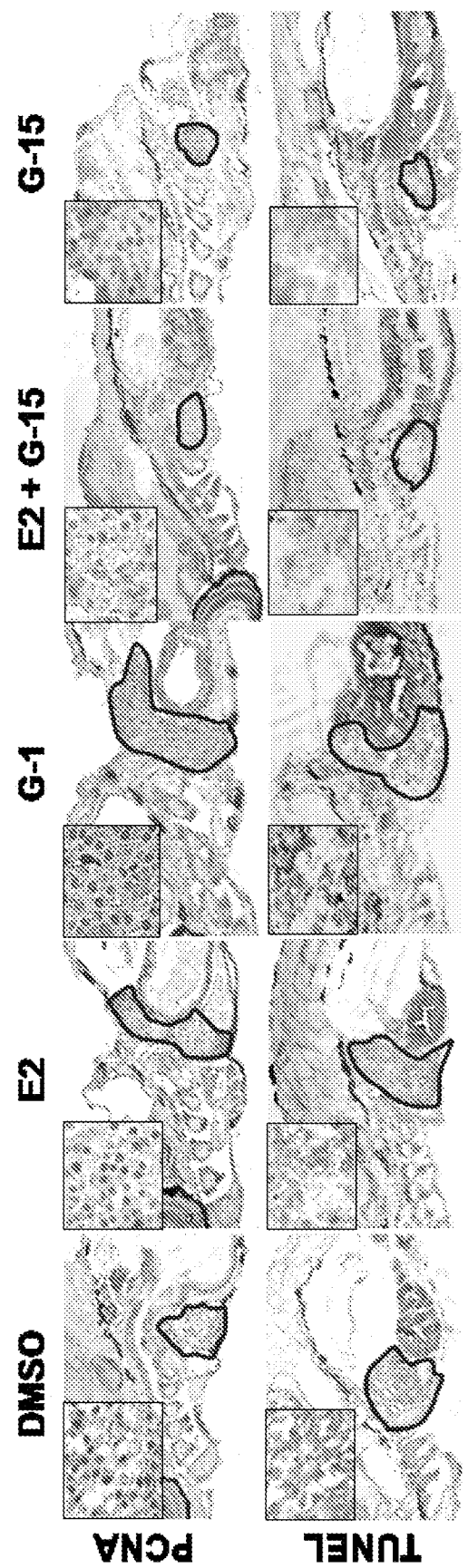
Figure 3F:
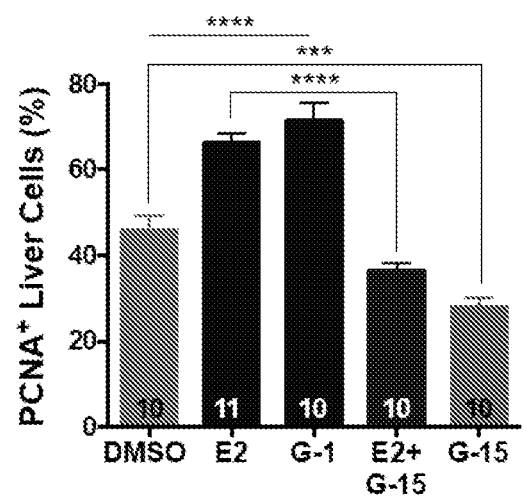
Figure 3G:
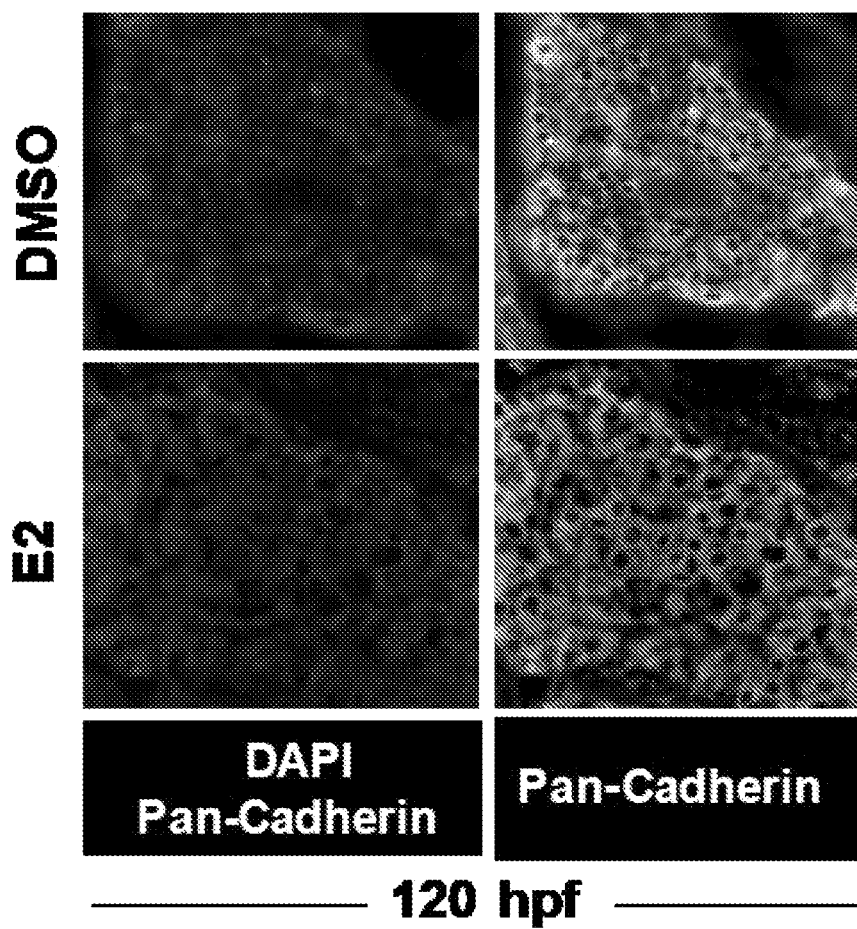
Figure 3H:
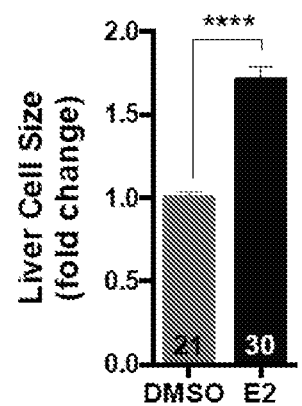
Figure 11A:
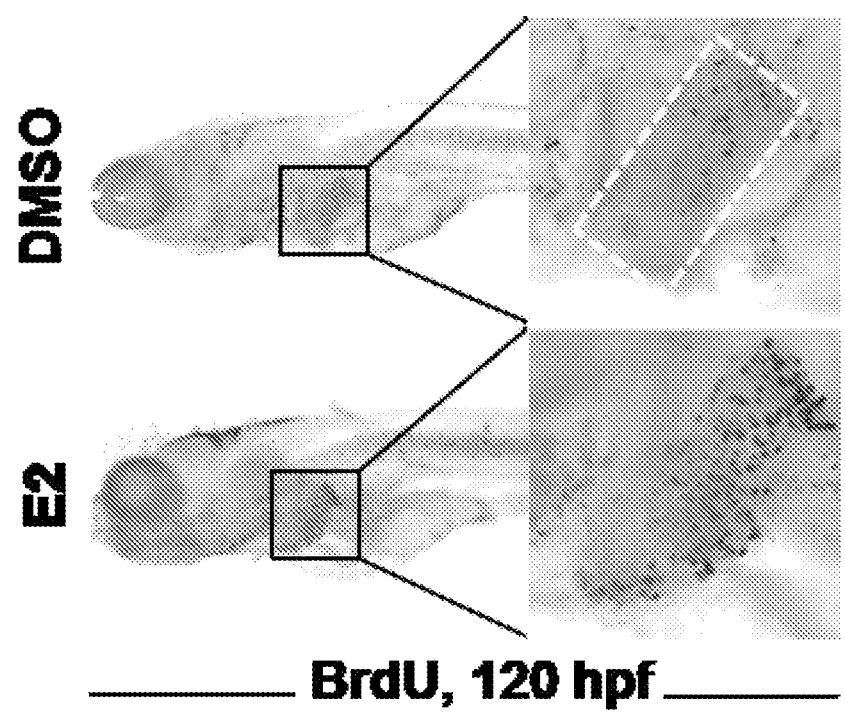
FIGS. 11A and 11B shows that estrogen increases cell proliferation in the liver.
Figure 11B:
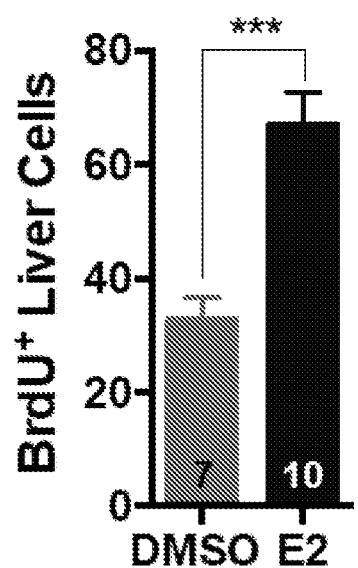

Estrogen Activates GPER1 to Promote Cellular Proliferation and Cell Cycle Progression To determine the cellular mechanism by which E2 enlarges liver size, cell cycle analysis was performed on propidium iodide-stained fabp10a:GFP$^+$ hepatocytes by flow cytometry (FIG. 3A). E2 and G-1 significantly increased hepatocytes in S and G2/M phase (S:21.8%; G2/M:9.4%) compared to controls (S:14.9%; G2/M:4.2%; $p<0.01$); importantly, this effect was blocked by co-exposure to G-15 (FIG. 3B; S:16.2%; G2/M:2.9%; $p<0.01$). In contrast, whole-larvae cell cycle analysis in gper1$^{-/-}$ mutants at 120 hpf revealed impaired cell cycle progression (S:14.8%; G2/M:8.1%; $p<0.01$) compared to age-matched controls (S:23.3%; G2/M:8.5%), demonstrating a requirement for GPER1 in normal cell cycle progression (FIGS. 3C and 3D). To corroborate these results, cellular proliferation was assessed by BrdU incorporation and staining for PCNA, revealing both enhanced BrdU incorporation (FIGS. 11A and 11B) and fractional increase of PCNA$^+$ cells in the liver after E2 or G-1 exposure (FIGS. 3E and 3F). Conversely, G-15 decreased PCNA$^+$ hepatocytes and inhibited the E2-induced increase in PCNA$^+$ hepatocytes (FIGS. 3E and 3F). Any impact of E2 on hepatocyte viability was excluded by TUNEL staining (FIG. 3E). Alterations in cell size as a contributor to organ size were also examined: pan-Cadherin immunostaining revealed a significant 50% increase in hepatocyte size upon E2 exposure (FIGS. 3G and 3H). These results indicate that E2 promotes hepatocyte proliferation, cell cycle progression and overall cell size via GPER1, leading to increased liver growth.

Estrogen Signals Through GPER1 to Stimulate the PI3K/Akt Pathway

Figure 4A:
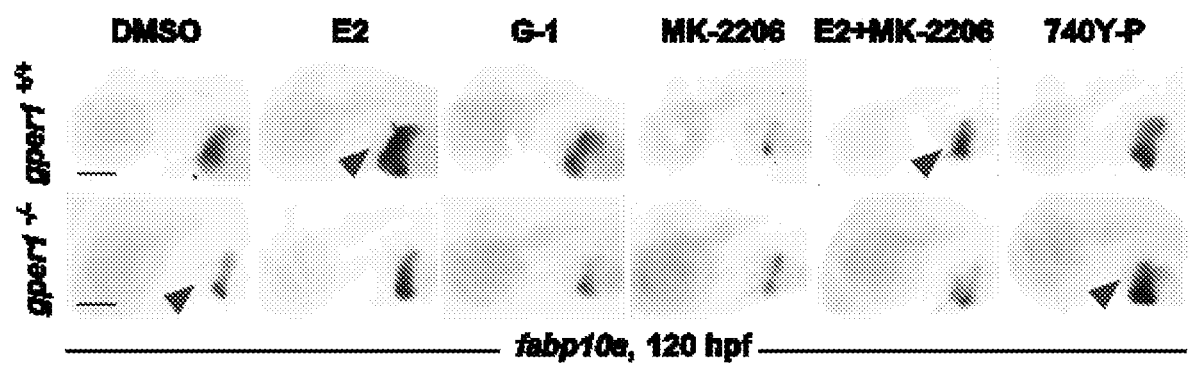
FIGS. 4A-4F show that E2 signals via GPER1 to stimulate PI3K/mTORC1 to increase liver size.
Figure 4B:
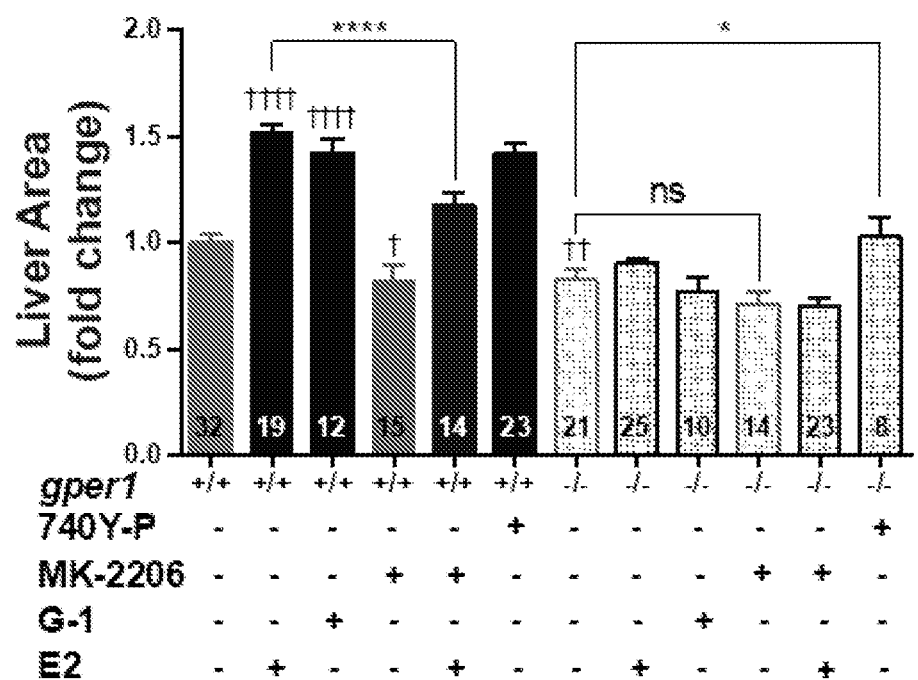
Figure 4C:
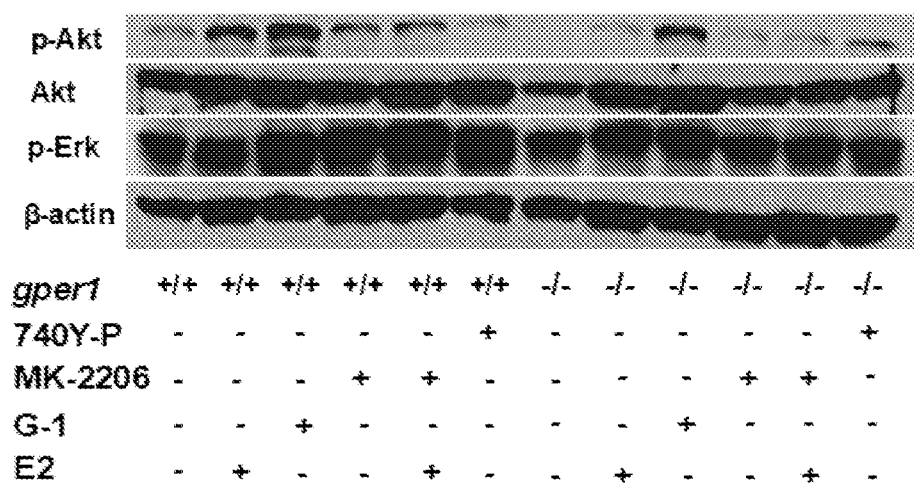
Figure 12A:
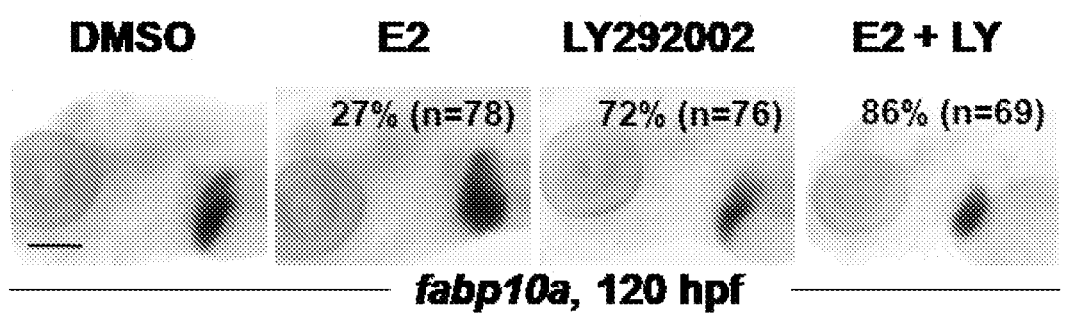
FIGS. 12A-12G show that estrogen signals through GPER1 to activate PI3K/mTOR pathway to increase liver size.
Figure 12B:
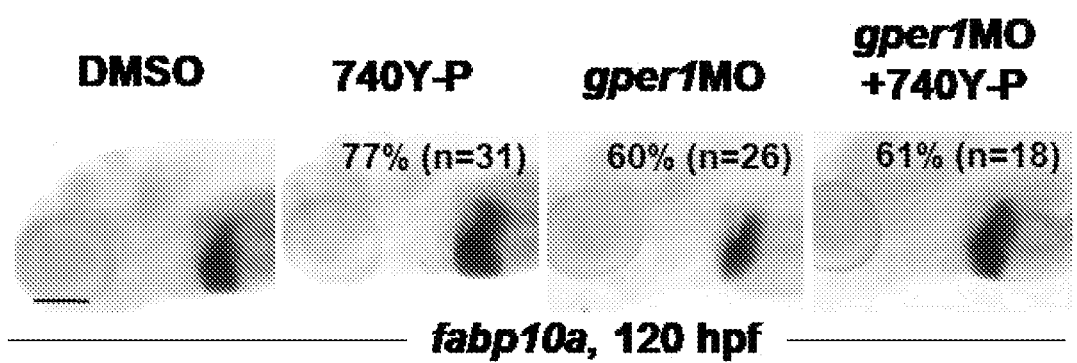

To determine the downstream signals by which GPER1 enhances liver growth, a targeted approach was employed, based on the observation that other G protein-coupled receptors can activate PI3K signaling.[22] To define the potential interaction between GPER1 and the PI3K/Akt pathway, larvae were exposed to PI3K inhibitor LY292002, PI3K activator 740Y-P, and Akt inhibitor MK-2206. While E2 increased liver size, co-exposure with either LY292002 or MK-2206 diminished this effect (FIGS. 4A, 4B, and 12A). MK-2206 alone decreased liver size in WT and to a lesser degree in gper1$^{-/-}$ mutants, suggesting that E2/GPER1-PI3K/Akt signaling is essential during larval liver outgrowth. In contrast, 740Y-P increased liver size in wild-type larvae and rescued liver growth in gper1 morphants or mutants (FIGS. 4A, 4B, and 12B). As PI3K can activate both Akt and MAPK/Erk pathways, the impact of E2 on MAPK/Erk signaling was also investigated. Western blot analysis for phosphorylated Akt (p-Akt) and phosphorylated Erk (p-Erk) indicated that E2 increased p-Akt, but had minimal effects on p-Erk (FIG. 4C). Consistent with these findings, gper1$^{-/-}$ mutants exhibited decreased baseline p-Akt levels compared to WT, whereas 740Y-P-exposure in gper1$^{-/-}$ mutants resulted in p-Akt restored to WT levels (FIG. 4C). These data demonstrate that E2 activates the PI3K/Akt pathway via GPER1 to increase liver mass.

Estrogen Activates mTORC1 Pathway Via GPER1 to Increase Liver Size

Figure 4D:
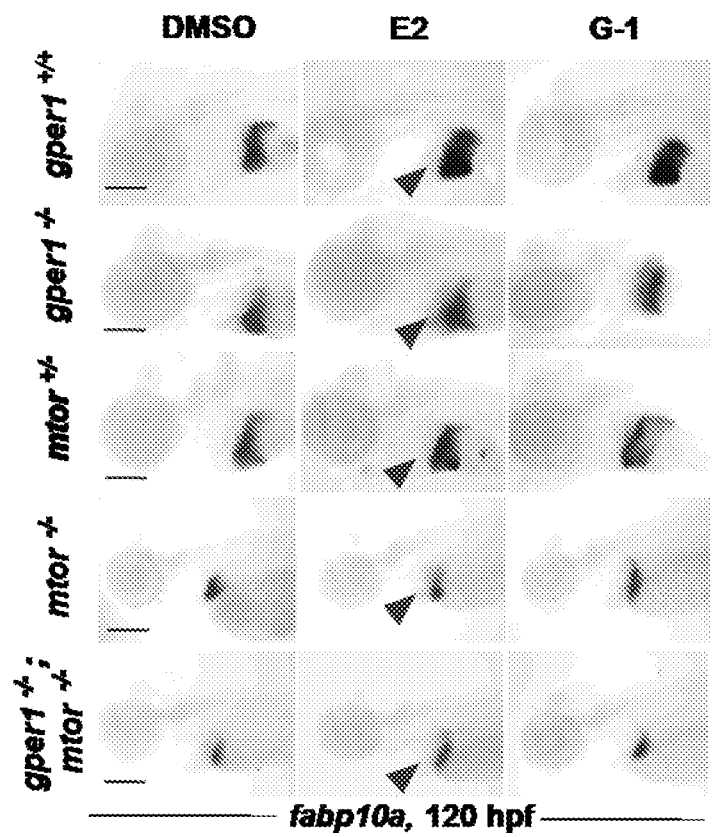
Figure 4E:
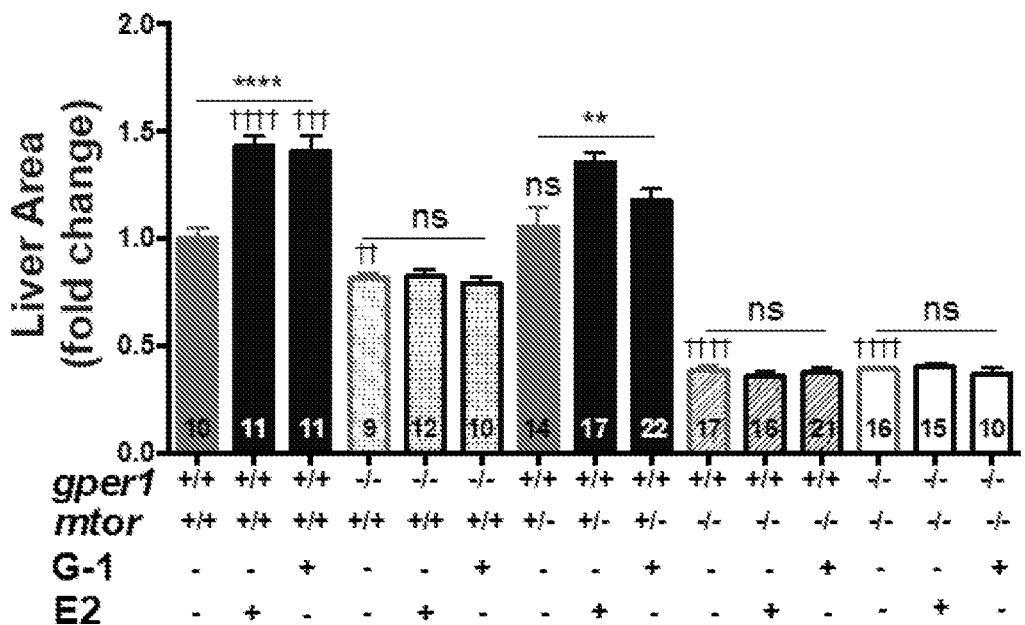
Figure 4F:
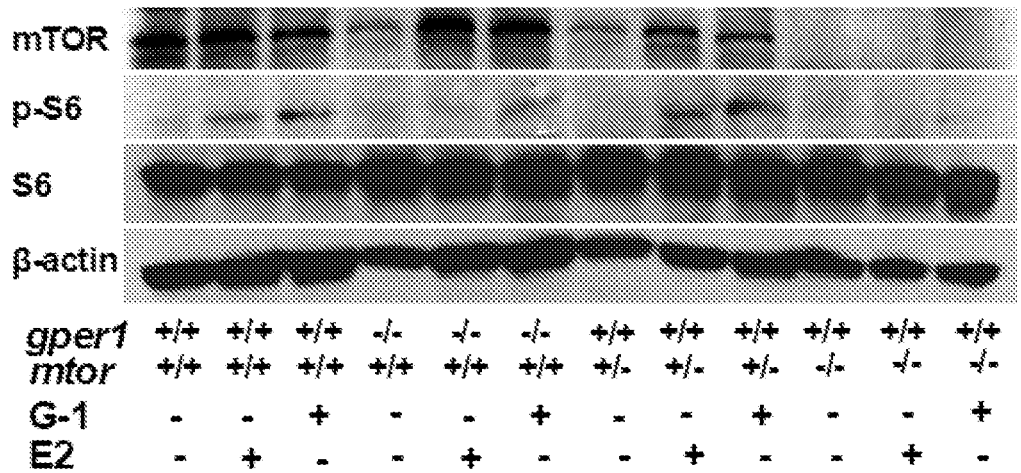
Figure 12C:
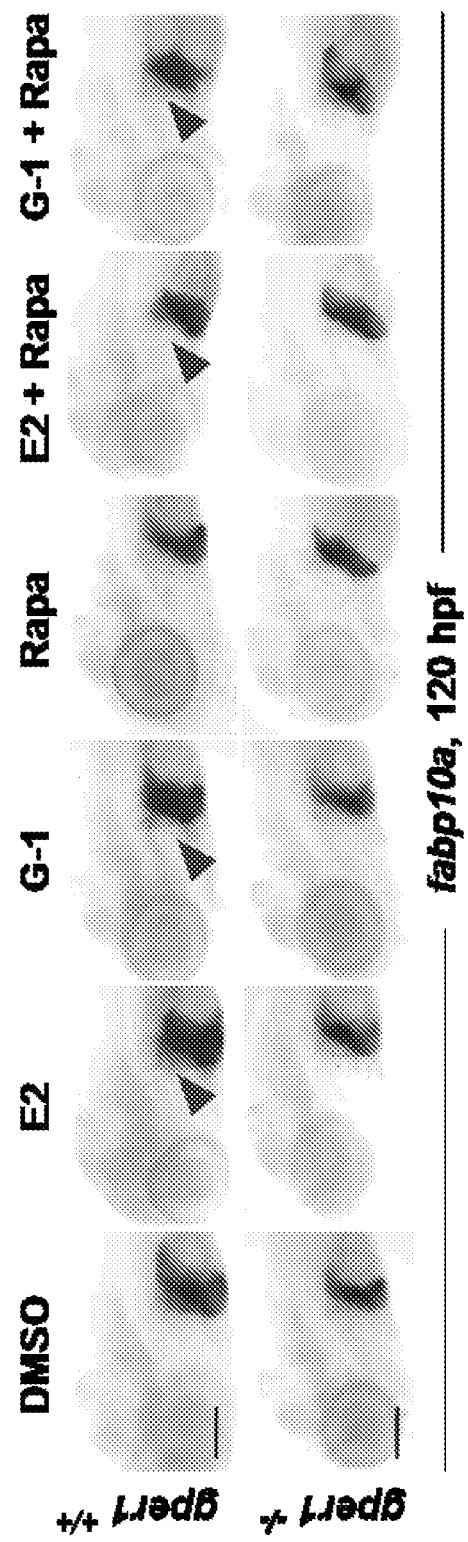
Figure 12D:
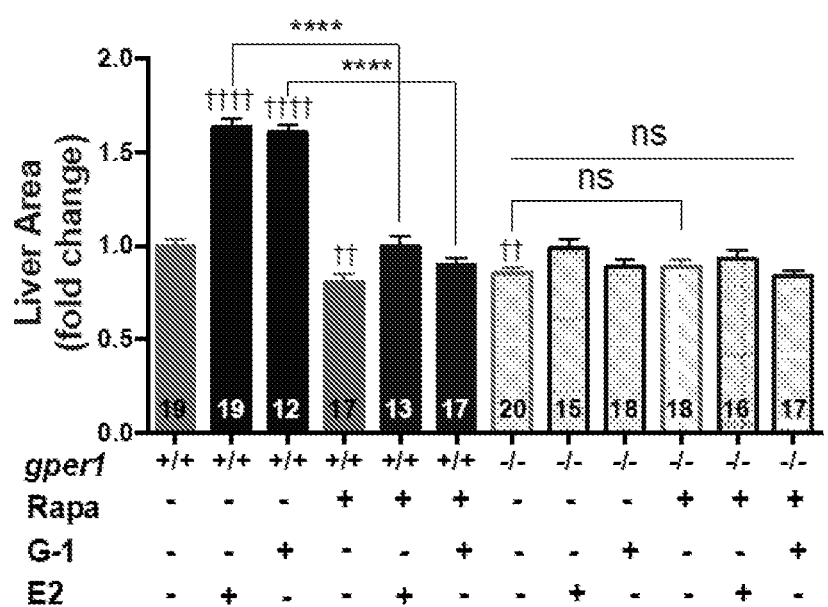
Figure 12E:
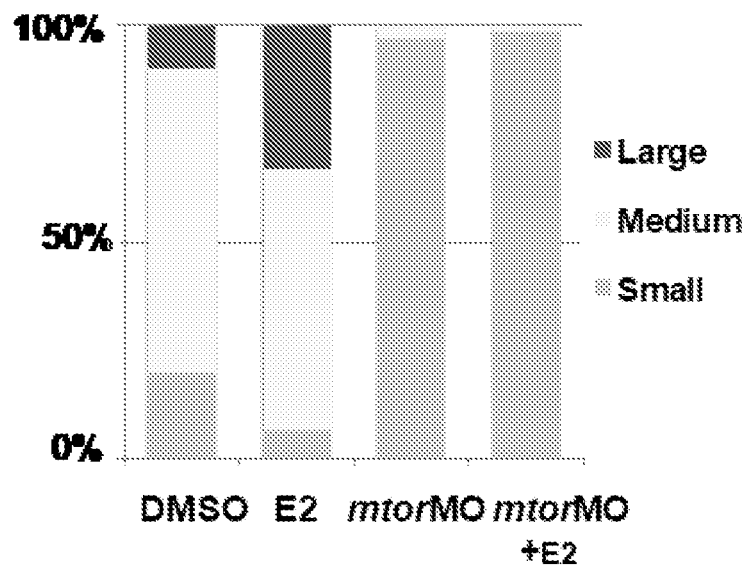
Figure 12F:
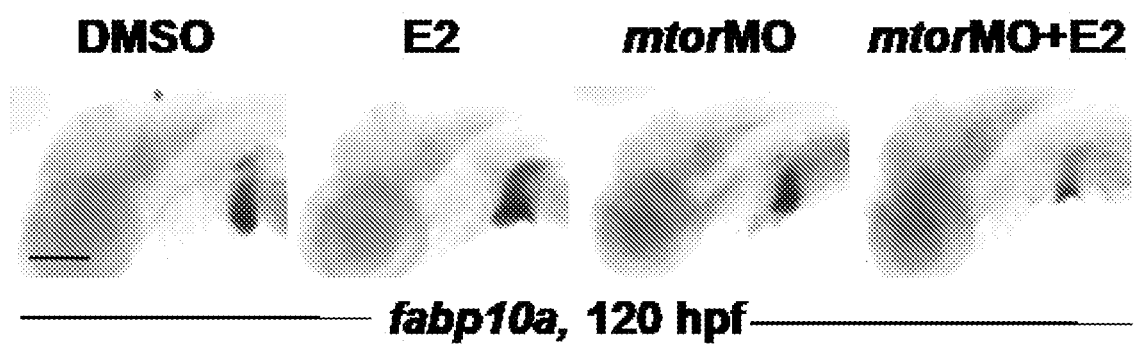
Figure 12G:
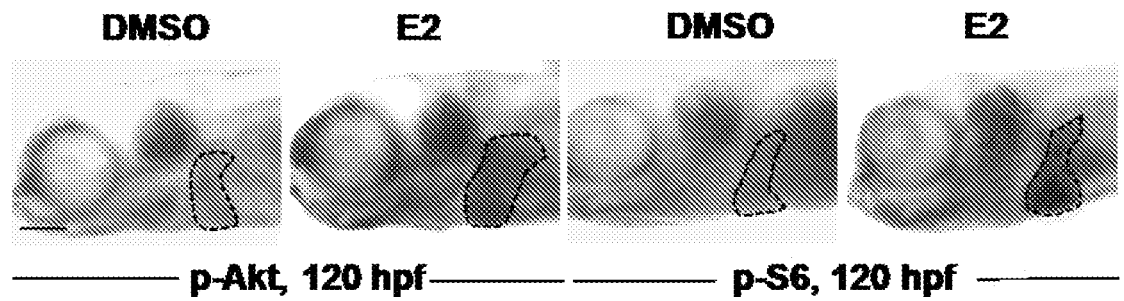

To determine the effector of E2/GPER1-mediated activation of PI3K/Akt signaling that controls liver growth, the role of the mechanistic target of rapamycin complex 1 (mTORC1), an established downstream target of Akt, was investigated. Co-exposure with the mTORC1 inhibitor rapamycin diminished the enlarged liver phenotype induced by either E2 or G-1 (FIGS. 12C and 12D). Similarly, knockdown of mtor alone decreased liver size and blocked E2 effects as assessed by fabp10a ISH (FIGS. 12E and 12F). Likewise, hypomorphic mtor mutants[23] exhibited smaller liver size that did not change upon E2 or G-1 exposure (FIGS. 4D and 4E). To investigate the epistatic relationship between GPER1 and mTOR, gper1$^{-/-}$; mtor$^{-/-}$ double mutants were generated: compound mutants displayed a reduced liver size that was indistinguishable from mtor$^{-/-}$ mutants (FIGS. 4D and 4E), suggesting that GPER1 acts in a linear pathway upstream of mTORC1. Finally, Western blot analysis of the mTORC1 target, ribosomal protein S6 (S6), demonstrated increased phosphorylated S6 (p-S6) after both E2 and G-1 exposure (FIG. 4F); importantly, IHC staining of treated embryos localized increased p-S6 to the liver (FIG. 12G). These effects were abolished in gper1$^{-/-}$ and mtor$^{-/-}$ mutants (FIG. 4F). Together, these functional and biochemical analyses demonstrate E2/GPER1-mediated regulation of liver size during development is dependent on activation of the PI3K/mTORC1 pathway.

Figure 5A:
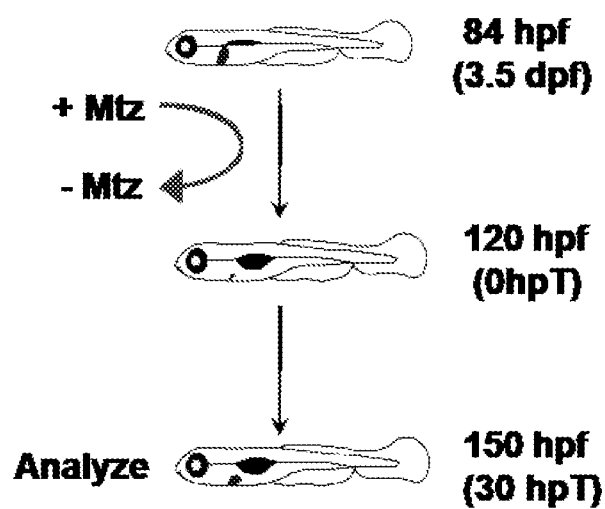
FIGS. 5A-5D show that E2 promotes liver regeneration via activation of GPER1 and mTORC1 pathways.
Figure 5B:
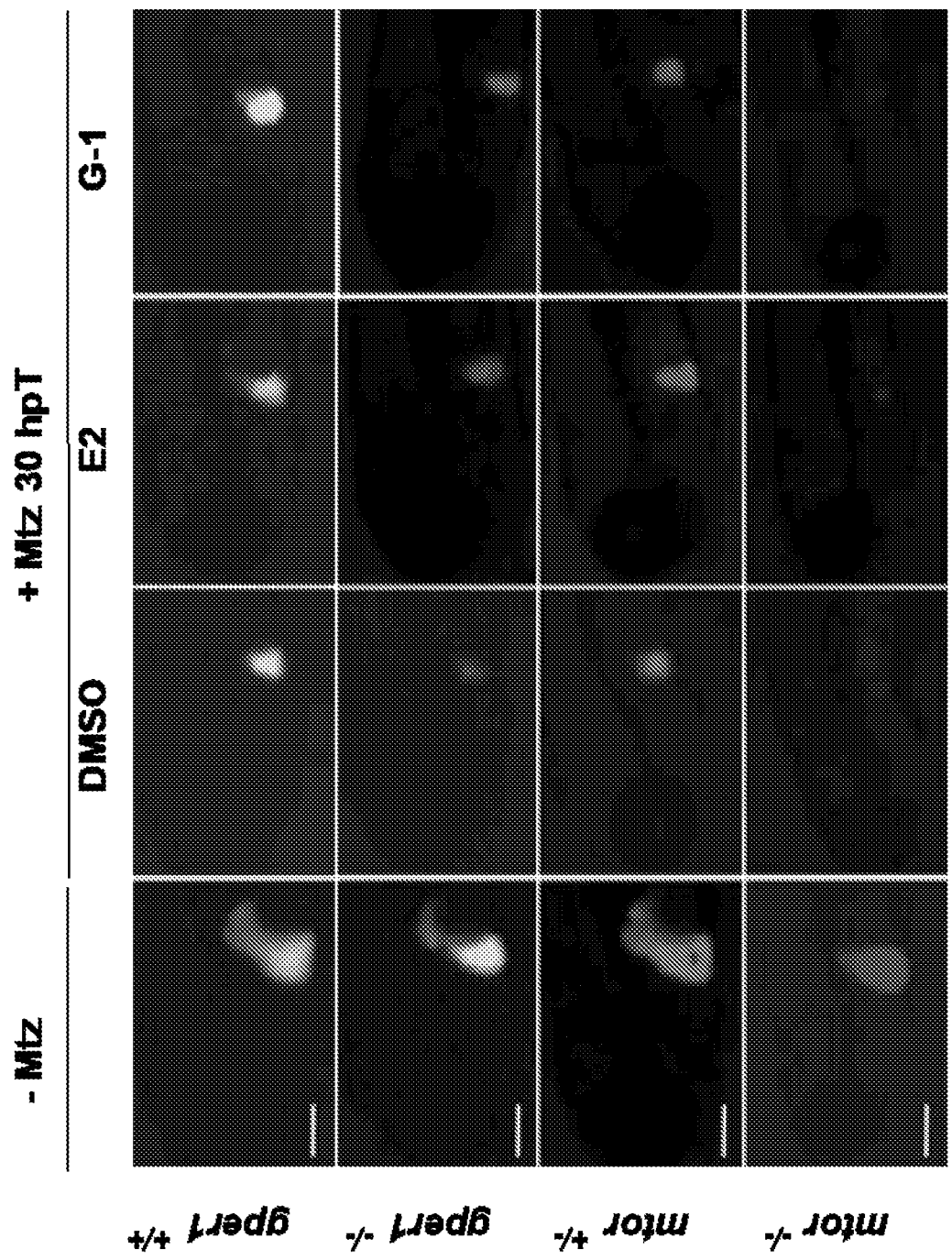
Figure 5C:
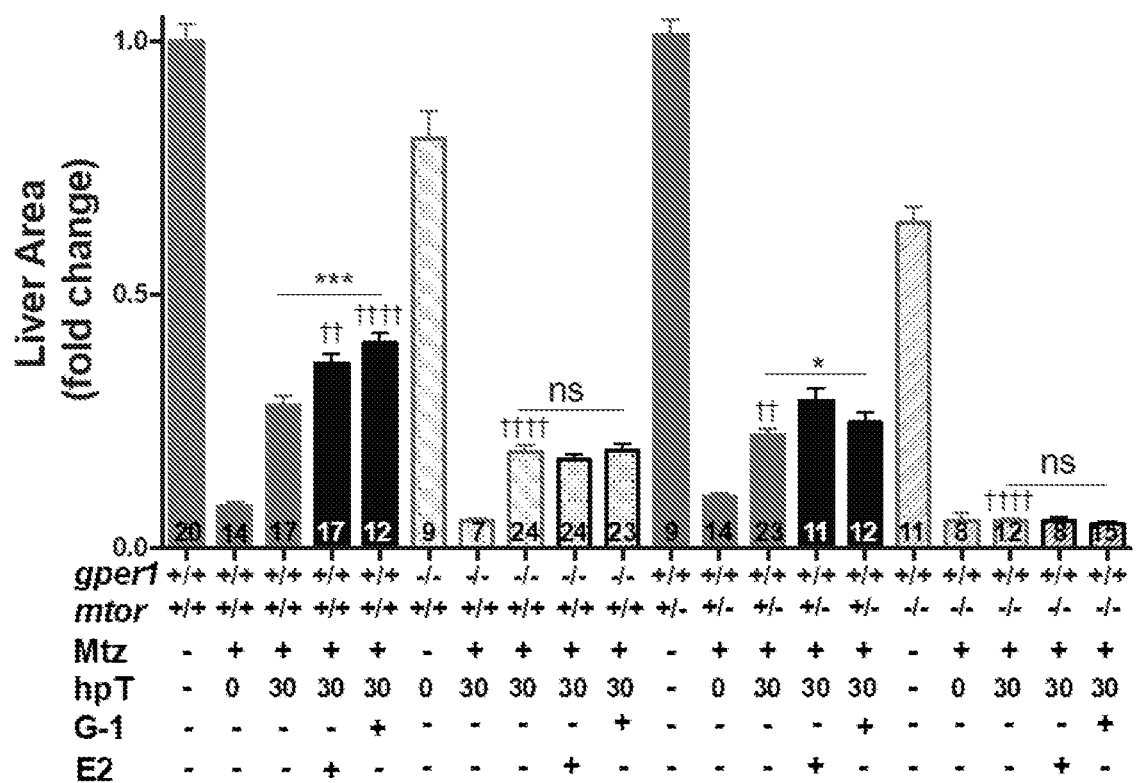

Estrogen Promotes Liver Regeneration Via Activation of GPER1 and mTORC1 Pathways Previous studies have demonstrated that many signals important for liver development are also essential for liver regeneration.[16,15] To determine whether the GPER1/mTOR pathway also regulates liver repair, a genetic ablation strategy was utilized: expression of bacterial nitroreductase in hepatocytes (Tg(fabp10a:CFP-NTR)) enables targeted ablation upon metronidazole (Mtz) exposure.[12] Larvae were exposed to Mtz from 84-120 hpf followed by chemical incubation for 5 hours and liver size assessment at 30 hours post-treatment (30 hpT) (FIG. 5A). E2 or G-1-exposed larvae demonstrated significantly larger liver size compared to controls, suggestive of enhanced liver repair (FIGS. 5B and 5C; $p<0.01$, $p<0.0001$). In contrast, gper1$^{-/-}$ mutants exhibited significantly reduced regrowth after ablation ($p<0.0001$), which was not enhanced by E2 or G-1 (FIGS. 5B and 5C). These results indicate that E2/GPER1 signaling acts in a pro-proliferative manner to enhance larval liver repair after injury.

Figure 5D:
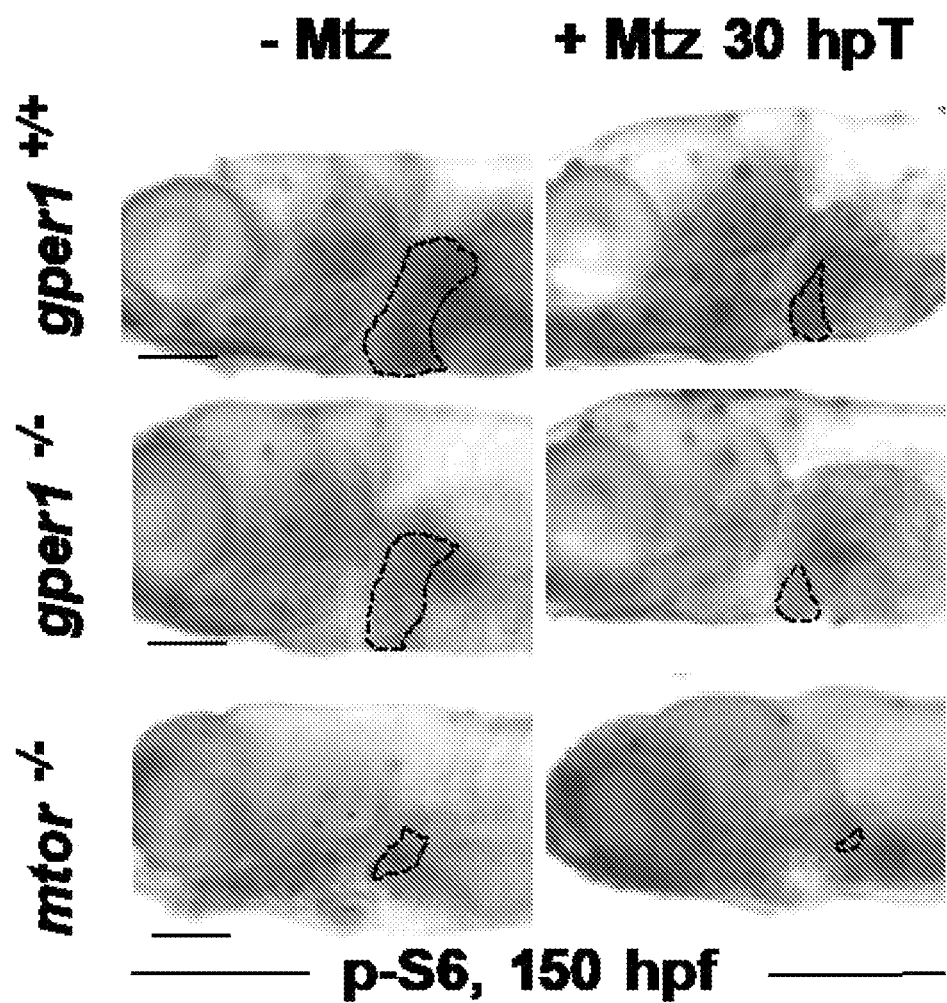

To examine the specific involvement of the E2/GPER1-PI3K/mTOR axis during liver repair, compound mtor$^{-/-}$: fabp10a:CFP-NTR fish were generated. Liver regrowth in mtor$^{-/-}$ mutants was significantly reduced compared to controls ($p<0.0001$) and not impacted by E2 or G-1 exposure (FIGS. 5B and 5C), highlighting a general requirement for mTOR during liver regeneration, and specifically in mediating the influence of E2 on liver repair. IHC demonstrated lower p-S6 levels in livers of both gper1$^{-/-}$ and mtor$^{-/-}$ mutants after injury, indicating that each failed to upregulate mTORC1 signaling upon hepatocyte ablation (FIG. 5D).

Collectively, our data reveal a direct connection between E2 and mTORC1 in promoting liver growth during regeneration.

GPER1 Mediates a Male-Biased Response to Estrogen on Adult Liver Growth

Figure 6A:
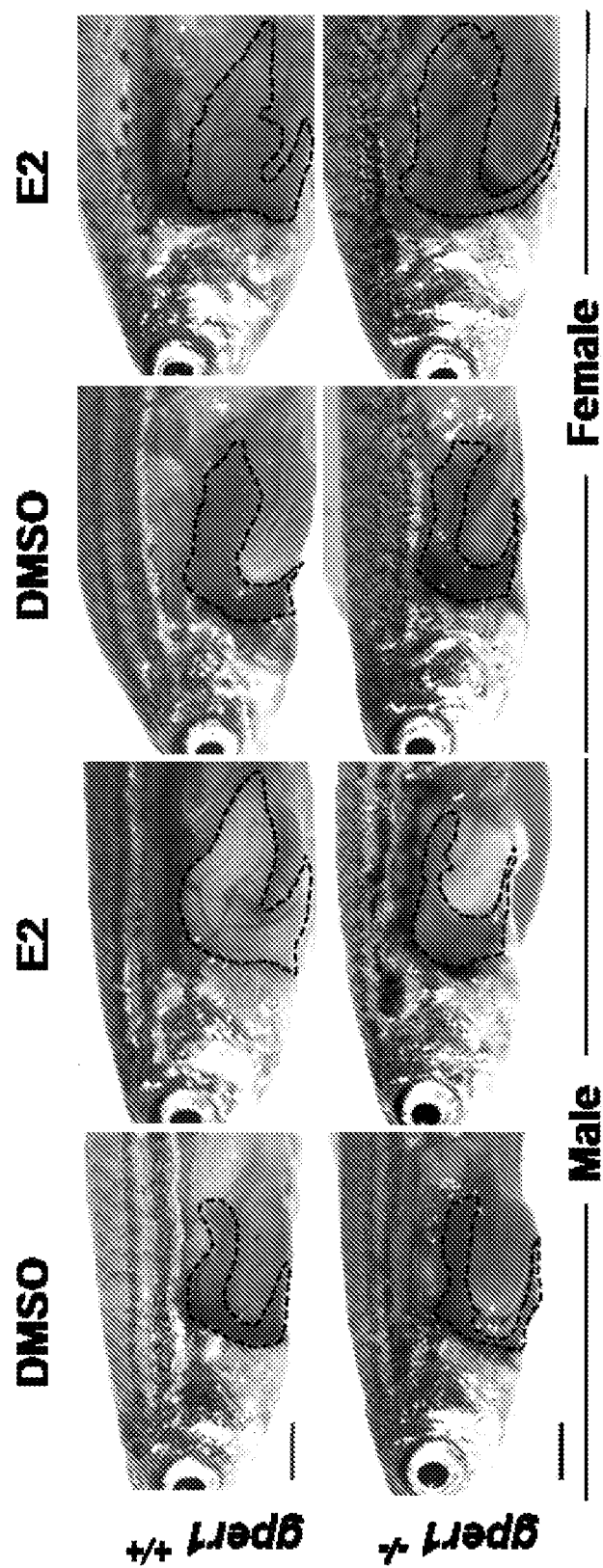
Figure 6D:
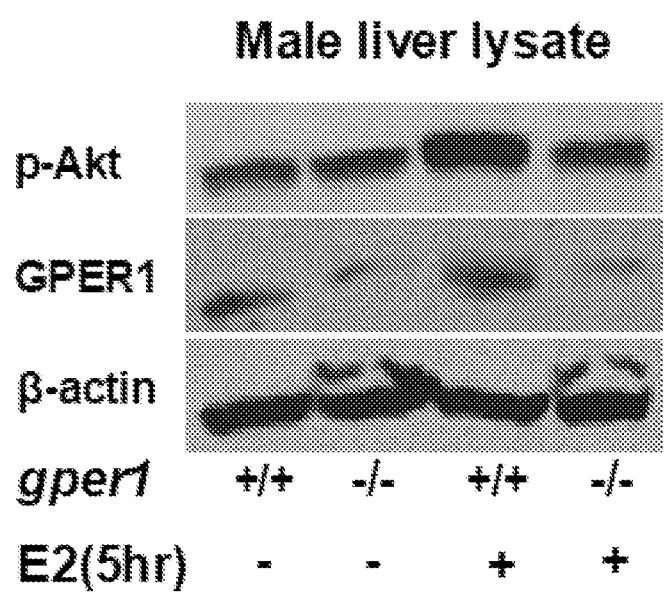

Given that E2/GPER1 signaling promotes liver growth and repair in zebrafish larvae, we postulated that it may similarly influence adult liver biology as suggested in FIG. 1. Steady-state liver weight in WT males and gper1$^{-/-}$ adults was not significantly different; in contrast, female gper1$^{-/-}$ livers were significantly lighter than age-matched WT, indicative of an impact of circulating E2 levels and intact GPER1 signaling for establishing sex-specific liver size differences (FIGS. 6A and 6B). Interestingly, the increase in liver weight upon E2 exposure in WT livers was significantly reduced in gper1$^{-/-}$ males, but not in females (FIGS. 6A and 6B). This sensitivity to E2 exposure may be explained by a 6-fold increase in gper1 expression levels in males over females (FIG. 6C). In support of this hypothesis, Western blot analysis demonstrated increased levels of p-Akt after 5 hours of E2 exposure in WT male livers but not those of gper1$^{-/-}$ mutants (FIG. 6D), highlighting the persistence of PI3K/Akt signaling as a target of E2/GPER1 in the adult. These results indicate that GPER1 is required for the response to circulating E2 in the female liver, while intrinsically higher levels of GPER1 expression sensitize male livers to exogenous E2-induced liver growth.

GPER1 Promotes Human Hepatocyte Growth and is Expressed in Liver Cancer

Figure 6E:
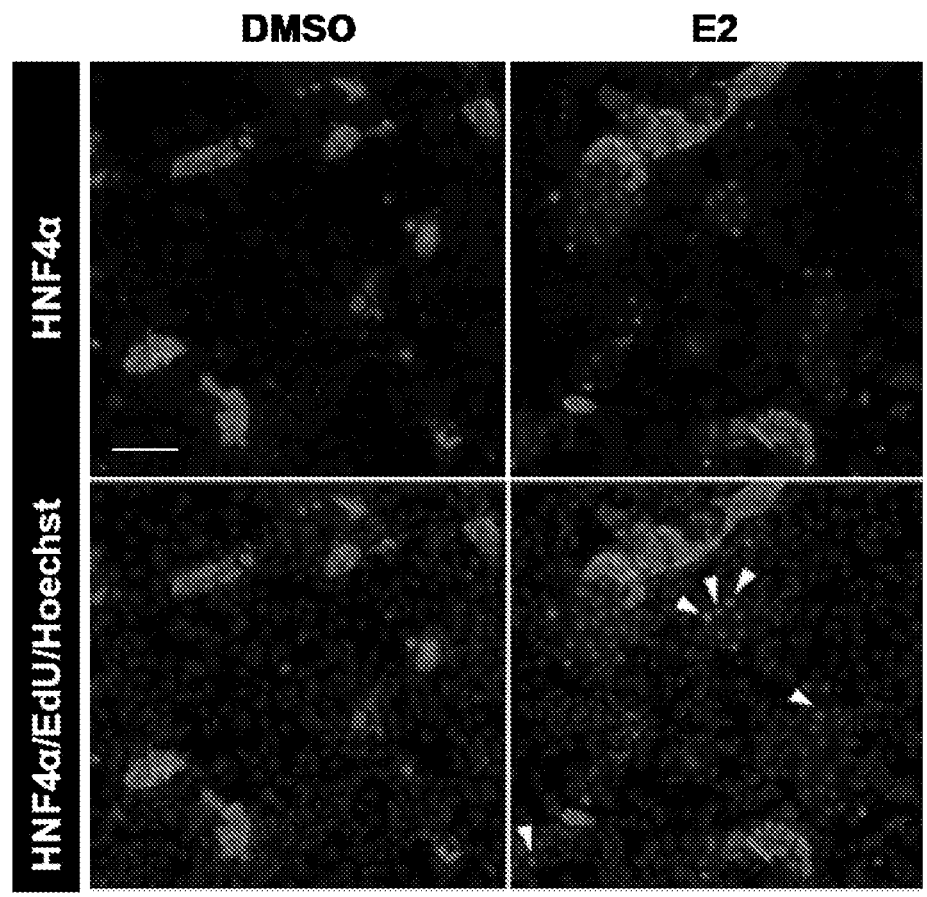
Figure 6F:
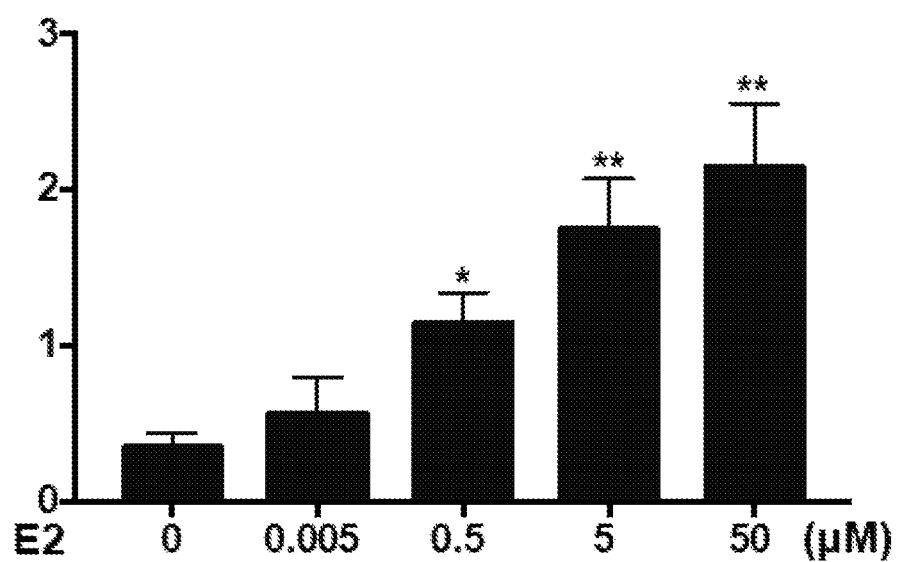
Figure 13:
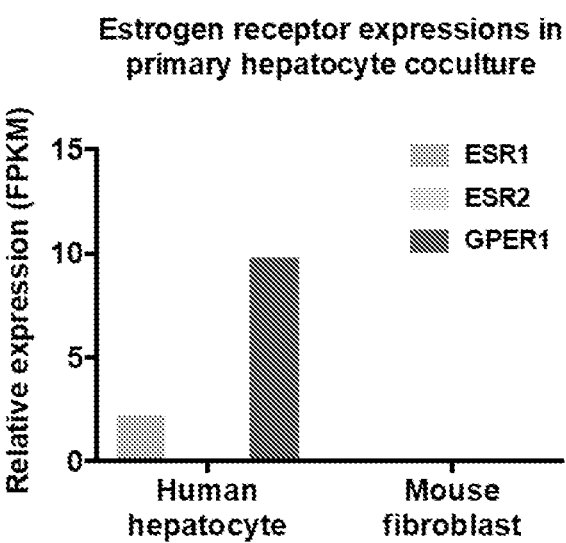
FIG. 13 shows that GPER1 is essential for male-biased response of estrogen on liver size. RNA sequencing data are depicted showing the relative expression in Fragments Per Kilobase of transcription per Million mapped reads (FPKM) of ESR1, ESR2, and GPER1 in human primary hepatocytes and in mouse fibroblast co-cultured cells.

To investigate whether the pro-proliferative effects of E2 could similarly be observed in human hepatocytes, a human primary hepatocyte co-culture system was employed.[24,25] E2 increased proliferation in male hepatocytes doubly labeled with hepatocyte nuclear factor 4 alpha (HNF4α) and ethynyldeoxyuridine (EdU) in a concentration-dependent manner (FIGS. 6E and 6F; p<0.01). Importantly, GPER1 is expressed in human hepatocytes, but not in the co-cultured support cells (FIG. 13), indicating a cell-autonomous effect of E2/GPER1 on hepatocyte proliferation. Together, these results demonstrate the conserved role of E2/GPER1 in promoting hepatocyte proliferation.

Figure 7A:
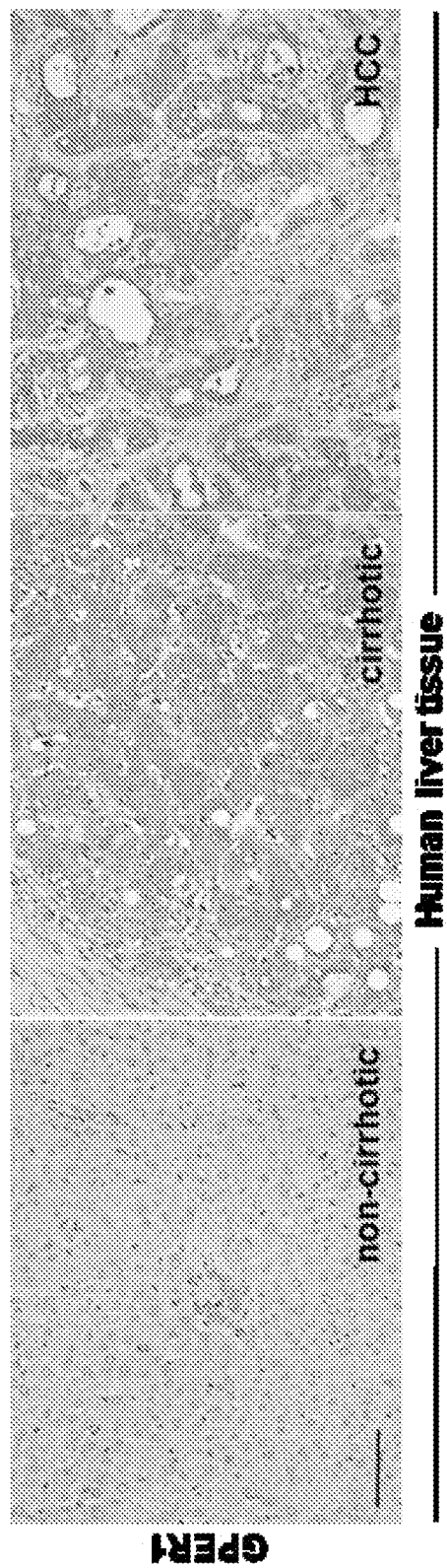
Figure 14A:
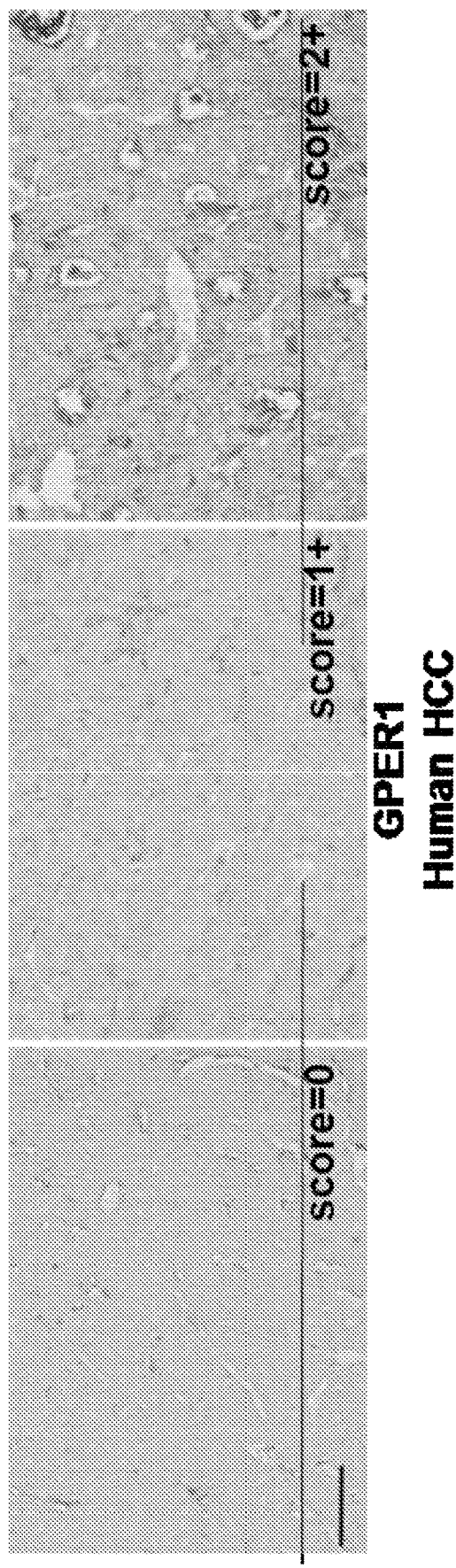
FIGS. 14A-14F shows that activation of E2/GPER1 signaling promotes male liver cancer initiation and progression.
Figure 14B:
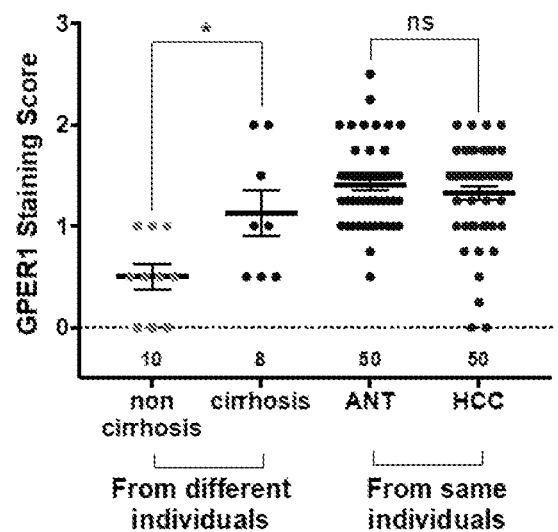
Figure 14C:
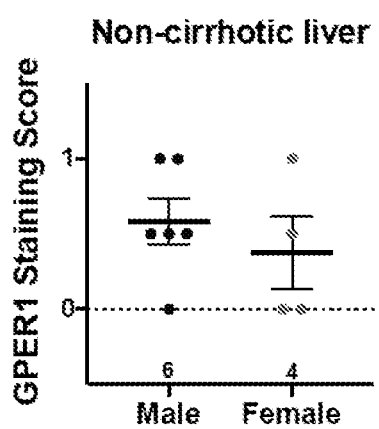
Figure 14D:
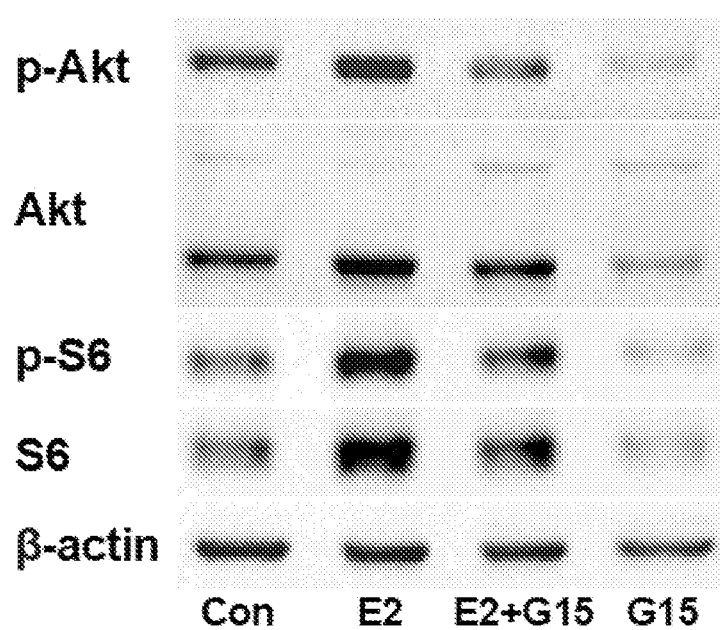

To assess the potential clinical relevance of GPER1 activity in the human liver, GPER1 expression was quantified in liver tissues from 68 individual patients by immunohistochemistry: 30% of non-cirrhotic livers exhibited positive GPER1 staining (staining score≥1+) (FIGS. 7A, 14A, and 14B). Importantly, GPER1 is expressed at higher levels in normal male livers than female livers (FIG. 14C). In contrast, 91% of cirrhotic livers, and 86% of HCC samples exhibited positive patchy to diffuse cytoplasmic GPER1 staining, with enhanced staining of hepatocytes around portal tracts and fibrous bands (FIGS. 7A, 14A, and 14B; non-cirrhotic vs. cirrhotic, p<0.05). These results indicate that GPER1 is increasingly expressed in cirrhotic livers and HCC, supporting a role for GPER1 in human hepatocarcinogenesis. Finally, in human HepG2 cells, E2-associated increases in p-Akt and p-S6, were blocked by G-15 co-exposure (FIG. 14D), demonstrating that E2 similarly signals via the Akt/mTOR pathway in human liver cancer.

GPER1 Contributes to Sex-Dimorphism in Cancer Formation and Progression

Figure 7B:
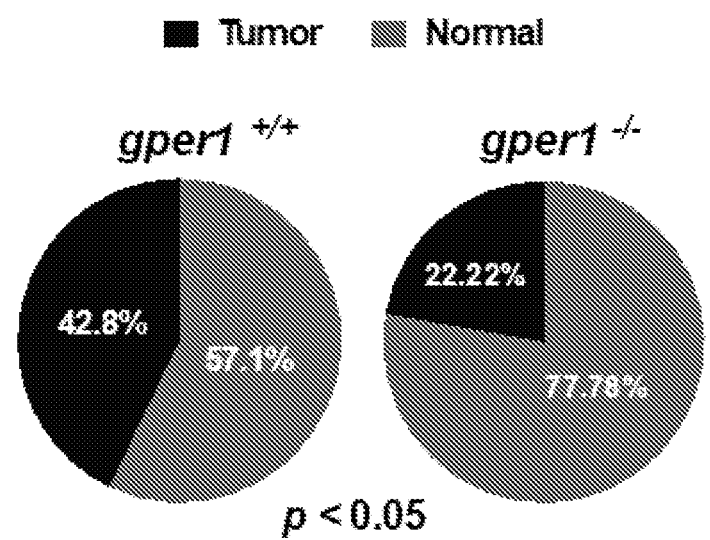
Figure 7C:
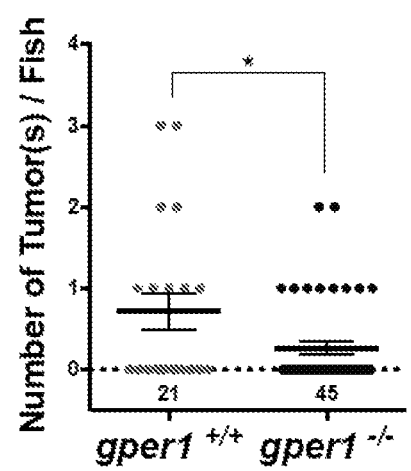

Dysregulation of signaling pathways controlling embryonic development and adult tissue homeostasis are frequently causative in carcinogenesis.[26,27] Given the role of E2/GPER1 in normal liver growth, its impact on cancer formation was examined in a well-established model of chemical liver carcinogenesis employing DMBA:[19] gper1$^{-/-}$ mutants exhibited significantly and dramatically reduced cancer incidence by 50% (FIG. 7B; 42.8% (n=21) vs. 22.2% (n=45), p<0.05). In addition, liver tumor number per fish as a measure of tumor initiation was decreased by >50% in gper1 mutants at 6 months post-DMBA (FIG. 7C; 0.7 vs. 0.3, p<0.05) compared to WT. Moreover, average liver tumor size as an indicator of tumor progression was decreased by >70% in gper1$^{-/-}$ mutants (FIG. 7D; 0.7 vs. 0.2 mm, p<0.01). These results demonstrate that GPER1 directly influences initiation and progression of liver cancer, suggesting a possible therapeutic role for receptor blockade.

Figure 7F:
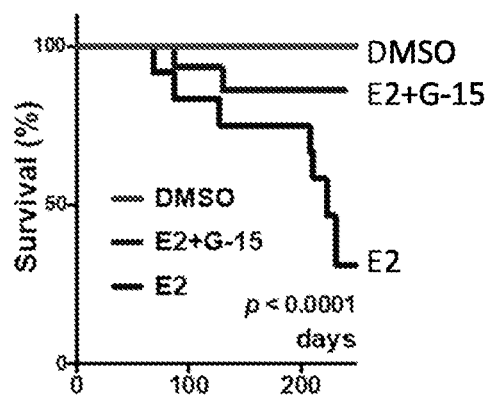
Figure 7G:
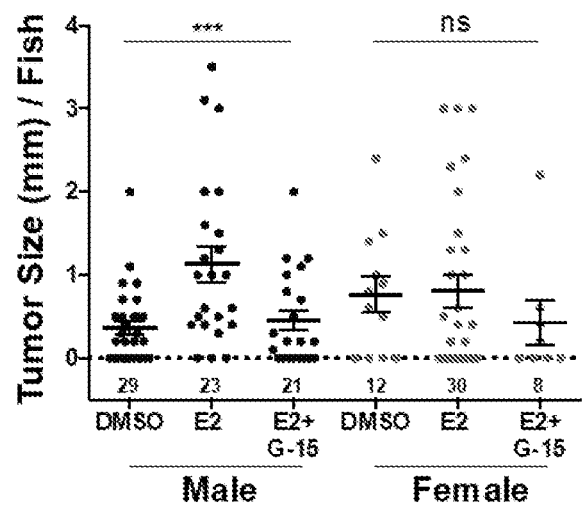
Figure 7H:
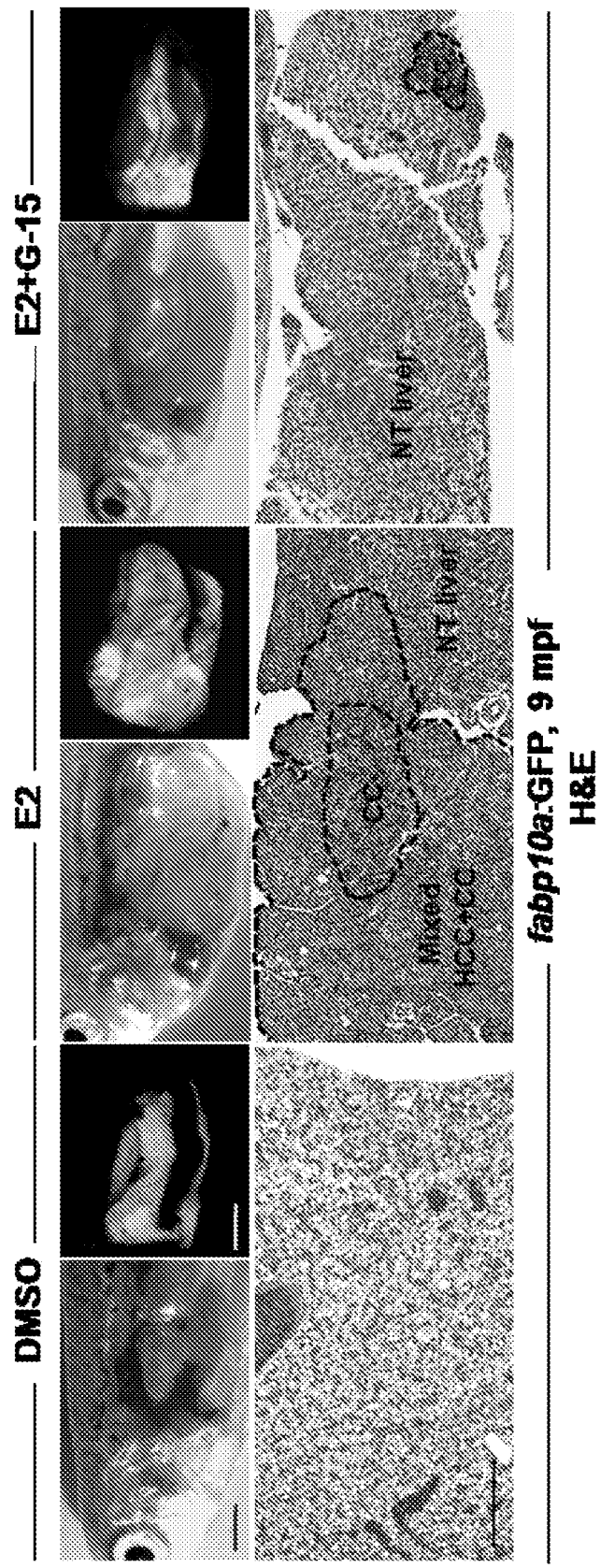
Figure 14E:
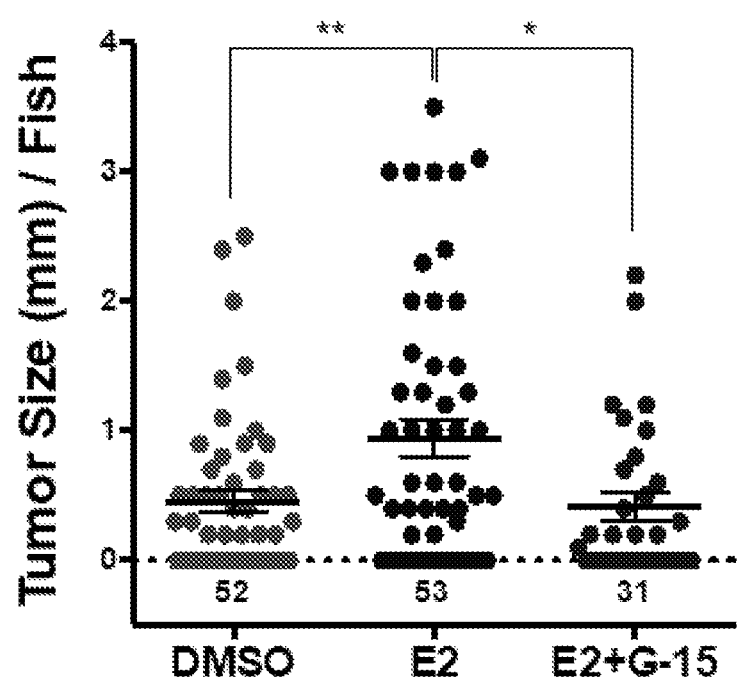
Figure 14F:
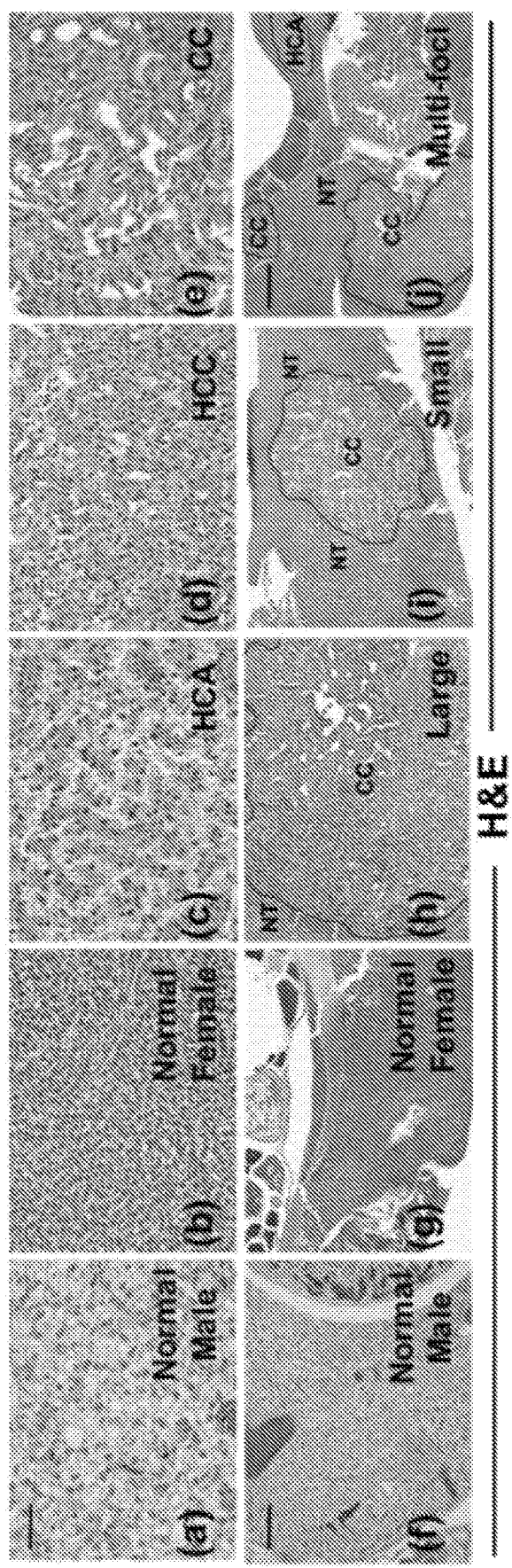

To determine if E2/GPER1 is a possible therapeutic target in liver carcinogenesis, DMBA-exposed WT were subsequently treated three times weekly with DMSO, E2, or a combination of E2+G-15 (FIG. 7E). Significantly, E2-exposed fish had decreased survival compared to controls and those concomitantly exposed to E2+G-15 (FIG. 7F; p<0.0001). Histological liver tumor analysis revealed hepatocellular adenoma (HCA), hepatocellular carcinoma (HCC) and cholangiocarcinoma (CC) (FIG. 14F). E2 exposure almost doubled liver tumor growth, as indicated by larger overall tumor size (FIG. 14E; mean 0.5 vs. 0.9 mm, p<0.01). Strikingly, G-15 co-exposure reduced the E2-associated increase in tumor burden back to below baseline levels (FIG. 14E; 0.9 vs. 0.4 mm, p=0.01). Given the observed sex-dimorphism in the response to E2 in adults, sex-stratified analysis of treatment response in each cohort was performed, revealing that E2-induced increases in tumor size are much more pronounced in male fish, where tumor size effectively tripled (FIGS. 7G and 7H; p<0.001); likewise, an impact of blockade by G-15 was predominantly observed in male, less in female fish (p<0.05). Together, these results indicate that GPER1 is an essential component of the sexually dimorphic response to E2 during liver growth and carcinogenesis, which may have therapeutic relevance for the detection and treatment of human liver disease.

Discussion

Liver cancer is the second most common cause of cancer death worldwide, and it predominantly affects men. Here, GPER1 was identified as a novel estrogen receptor in hepatocytes that cell-autonomously regulates larval liver growth and contributes to the sex-dimorphism observed in liver cancer. E2 promotes hepatocyte cell cycle progression and proliferation through GPER1 and downstream activation of PI3K/mTOR signaling. Importantly, the GPER1/mTOR pathway remains essential for proliferative expansion of hepatocytes during liver repair. Prospective in vivo longitudinal carcinogenesis assays identify GPER1 as an important factor promoting E2-mediated liver cancer initiation and progression. Unique sex stratification analysis demonstrates a male-predominant effect. Importantly, preclinical studies utilizing a selective GPER1 antagonist highlight the therapeutic potential of GPER1 blockade for liver cancer treatment. Increased expression of GPER1 in cirrhotic livers and HCC indicate its possible utility as a biomarker.

The mTOR pathway is essential for organ size regulation,[28] functioning as a growth checkpoint that tightly coordinates cell growth with environmental cues, such as cellular stress, energy status, and amino acid availability.[27] Here, we reveal a previously unidentified role of E2/GPER1 was revealed, wherein it acts upstream of mTORC1 to promote hepatocyte proliferation and liver growth. The impact of E2/GPER1 activation of mTORC1 on pyrimidine and purine metabolism was also identified, supporting recent studies showing that mTORC1 is essential for de novo pyrimidine and purine biosynthesis to meet the anabolic demands of rapidly proliferating cells.[29-31] Prior studies have reported the sexual dimorphism of mTOR activity in the liver.[32-34] The present study is the first to elucidate how hepatic mTOR could sense a sex-specific environment, providing a novel mechanism through GPER1 acting as an E2 sensor to regulate mTOR activity and influence liver growth.

Several clinical and laboratory studies have shown sexually dimorphic responses of the liver after hepatectomy, with females being more tolerant and having a higher rate of liver regeneration.[35] E2 concentrations reportedly increase after liver injury,[36] and improve the impairment in liver regeneration found in ovariectomized female mice.[37] The mechanisms involved, however, had been incompletely understood. Here, it has been demonstrated that E2 specifically activates GPER1 and mTORC1 to promote liver regrowth after injury. The importance of this E2 regulatory axis can be gleaned from clinical observations: E2 levels have long been known to rapidly increase after liver resection in patients.[5] Further, pregnancy is also associated with hepatomegaly,[38] and the gestational increase of E2 enhances the liver repair response,[39] suggesting a physiological benefit for E2 signaling during periods of liver growth. Indeed, $gper1^{-/-}$ mutants exhibit significantly delayed liver outgrowth during development and following injury. Nevertheless, $gper1^{+/+}$ mutants have a greater capacity for liver regeneration compared to $mtor^{-/-}$ mutants, indicating that E2/GPER1 is one among many potential inputs integrated by mTOR to regulate liver regeneration. GPER1 may be the conserved sensor that mediates E2 activation of PI3K/mTOR signaling in a sex-dimorphic fashion to promote liver regeneration.

Sexual dimorphism in liver cancer has long been documented. While several studies implicate E2 in HCC pathogenesis,[40] a detailed mechanistic understanding has not been established. Current reports have described both protective and tumor-promoting effects for E2: E2-mediated reduction of inflammatory cytokines, such as IL-6 in liver-resident immune cells, appears to inhibit tumorigenesis.[41,42] E2 may play a protective role via an ESR1-mediated interaction with transcription factor Foxa1/2;[43] nevertheless, in the absence of Foxa1/2, E2 promoted liver tumorigenesis. Several other studies have shown liver tumor-promoting properties of E2.[44,45] Clinical trials in HCC patients using the ESR antagonist tamoxifen have been disappointing;[46,47] in fact, tamoxifen increased the size and number of hepatic lesions.[48,49] Importantly, tamoxifen was subsequently found to be an agonist for GPER1,[50,51] explaining the negative clinical results and consistent with our mechanistic analysis. These observations highlight the complexity and specificity of E2-mediated signaling: the response elicited will be both cell-type and receptor specific. These findings are of particular importance as men with cirrhosis have persistently elevated serum levels of E2 due to impaired hepatic uptake and metabolism, and these patients are the same population at highest risk for developing liver cancer. The results of the present study definitively demonstrate a growth-promoting role for E2 in liver cancer acting through hepatocyte-associated GPER1.

The involvement of GPER1-PI3K/mTOR signaling in hepatocyte proliferation prompted the hypothesis that GPER1 also promotes liver carcinogenesis. Indeed, activation of PI3K/Akt (~70%) and mTORC1 (~45%) pathways is found in HCC and positively correlates with tumor metastasis, recurrence, and poor prognosis.[52,53] Genetic alterations of PI3K/mTOR pathway components are found at lower frequencies in HCC: exome sequencing revealed mutation frequencies in PIK3CA ($\leq 2\%$), mTOR ($\leq 2\%$), TSC1/TSC2 ($\leq 5\%$), and PTEN ($\leq 3\%$).[54,55] It is possible that PI3K/mTOR activity in HCC may instead depend upon upstream ligand activation, such as that mediated by increased E2 levels and GPER1 expression in cirrhotic patients. As over 80% of HCC patients are diagnosed at late stages without hope for cure, there is clearly an urgent need for earlier detection and targeted therapeutic interventions. The pro-proliferative consequences of E2/GPER1 activation of PI3K/mTOR signaling, together with the in vivo data in this study showing strong responses to GPER1 antagonist treatment in both cancer initiation and progression clearly indicate that drugs targeting E2/GPER1 may offer exciting new therapeutic applications in liver cancer prevention and treatment.

REFERENCES

1. Ferlay J, Soerjomataram I, Dikshit R, et al. Cancer incidence and mortality worldwide: sources, methods and major patterns in GLOBOCAN 2012. Int J Cancer. 2015; 136(5):E359-86.
2. Sato N, Lindros K O, Baraona E, et al. Sex difference in alcohol-related organ injury. Alcohol Clin Exp Res. 2001; 25(5 Suppl ISBRA):40S-45S.
3. Guéchot J, Peigney N, Ballet F, et al. Sex hormone imbalance in male alcoholic cirrhotic patients with and without hepatocellular carcinoma. Cancer. 1988; 62(4): 760-2.
4. Castagnetta L A M, Agostara B, Montalto G, et al. Local estrogen formation by nontumoral, cirrhotic, and malignant human liver tissues and cells. Cancer Res. 2003; 63(16):5041-5.
5. Francavilla A, Panella C, Polimeno L, et al. Hormonal and enzymatic parameters of hepatic regeneration in patients undergoing major liver resections. Hepatology. 1990; 12(5):1134-8.
6. Barros R P A, and Gustafsson J-Å. Estrogen receptors and the metabolic network. Cell Metab. 2011; 14(3):289-99.
7. Filardo E J, Quinn J A, Bland K I, et al. Estrogen-induced activation of Erk-1 and Erk-2 requires the G protein-coupled receptor homolog, GPR30, and occurs via trans-activation of the epidermal growth factor receptor through release of HB-EGF. Mol Endocrinol. 2000; 14(10):1649-60.
8. Haas E, Bhattacharya I, Brailoiu E, et al. Regulatory role of G protein-coupled estrogen receptor for vascular function and obesity. Circ Res. 2009; 104(3):288-91.
9. Ruiz-Palmero I, Hernando M, Garcia-Segura L M, et al. G protein-coupled estrogen receptor is required for the neuritogenic mechanism of 17β-estradiol in developing hippocampal neurons. Mol Cell Endocrinol. 2013; 372(1-2):105-15.
10. Holm A, Hellstrand P, Olde B, et al. The G protein-coupled estrogen receptor 1 (GPER1/GPR30) agonist G-1 regulates vascular smooth muscle cell $Ca^{2+}$ handling. J Vasc Res. 2013; 50(5):421-9.
11. de Bari O, Wang T Y, Liu M, et al. Estrogen induces two distinct cholesterol crystallization pathways by activating ERα and GPR30 in female mice. J Lipid Res. 2015; 56(9):1691-700.
12. Curado S, Anderson R M, Jungblut B, et al. Conditional targeted cell ablation in zebrafish: a new tool for regeneration studies. Dev Dyn. 2007; 236(4):1025-35.
13. Carroll K J, Esain V, Garnaas M K, et al. Estrogen defines the dorsal-ventral limit of VEGF regulation to specify the location of the hemogenic endothelial niche. Dev Cell. 2014; 29(4):437-53.

14. Sander J D, Cade L, Khayter C, et al. Targeted gene disruption in somatic zebrafish cells using engineered TALENs. Nature biotechnology. 2011; 29(8):697.
15. Goessling W, North T E, Loewer S, et al. Genetic interaction of PGE2 and Wnt signaling regulates developmental specification of stem cells and regeneration. Cell.
2009; 136(6):1136-47.
16. Goessling W, North 1E, Lord A M, et al. APC mutant zebrafish uncover a changing temporal requirement for wnt signaling in liver development. Dev Biol. 2008; 320(1):161-74.
17. Jayasinghe B S, and Volz D C. Aberrant ligand-induced activation of G protein-coupled estrogen receptor 1 (GPER) results in developmental malformations during vertebrate embryogenesis. Toxicol Sci. 2012; 125(1):262-73.
18. Cox A G, Hwang K L, Brown K K, et al. Yap reprograms glutamine metabolism to increase nucleotide biosynthesis and enable liver growth. Nat Cell Biol. 2016; 18(8):886-96.
19. Spitsbergen J M, Tsai H W, Reddy A, et al. Neoplasia in zebrafish (Danio rerio) treated with 7,12-dimethylbenz[a] anthracene by two exposure routes at different developmental stages. Toxicol Pathol. 2000; 28(5):705-15.
20. Yuan M, Breitkopf S B, Yang X, et al. A positive/negative ion-switching, targeted mass spectrometry-based metabolomics platform for bodily fluids, cells, and fresh and fixed tissue. Nat Protoc. 2012; 7(5):872-81.
21. Gorelick D A, and Halpern M E. Visualization of estrogen receptor transcriptional activation in zebrafish. Endocrinology. 2011; 152(7):2690-703.
22. Dorsam R T, and Gutkind J S. G-protein-coupled receptors and cancer. Nat Rev Cancer. 2007; 7(2): 79-94.
23. Ding Y, Sun X, Huang W, et al. Haploinsufficiency of target of rapamycin attenuates cardiomyopathies in adult zebrafish. Circ Res. 2011; 109(6):658-69.
24. Khetani S R, and Bhatia S N. Microscale culture of human liver cells for drug development. Nat Biotechnol. 2008; 26(1):120-6.
25. Shan J, Schwartz R E, Ross N T et al, dentification of small molecules for human hepatocyte expansion and iPS differentiation. Nat Chem Biol. 2013; 9(8):514-20.
26. Manning B D, and Cantley L C. AKT/PKB signaling: navigating downstream. Cell. 2007; 129(7):1261-74.
27. Laplante M, and Sabatini D M. mTOR signaling in growth control and disease. Cell. 2012; 149(2):274-93.
28. Lloyd A C. The regulation of cell size. Cell. 2013; 154(6):1194-205.
29. Ben-Sahra I, Howell J J, Asara J M, et al. Stimulation of de novo pyrimidine synthesis by growth signaling through mTOR and S6K1. Science. 2013; 339(6125): 1323-8.
30. Robitaille A M, Christen S, Shimobayashi M, et al. Quantitative phosphoproteomics reveal mTORC1 activates de novo pyrimidine synthesis. Science. 2013; 339 (6125):1320-3.
31. Ben-Sahra I, Hoxhaj G, Ricoult S J H, et al. mTORC1 induces purine synthesis through control of the mitochondrial tetrahydrofolate cycle. Science. 2016; 351(6274): 728-33.
32. Drake J C, Peelor F F, III, Biela L M, et al. Assessment of Mitochondrial Biogenesis and mTORC1 Signaling During Chronic Rapamycin Feeding in Male and Female Mice. The Journals of Gerontology Series A: Biological Sciences and Medical Sciences. 2013; 68(12):1493-501.
33. Baar E L, Carbajal K A, Ong I M, et al. Sex- and tissue-specific changes in mTOR signaling with age in C57BL/6J mice. Aging Cell. 2016; 15(1):155-66.
34. Tsai S-Y, Rodriguez A A, Dastidar S G, et al. Increased 4E-BP1 Expression Protects against Diet-Induced Obesity and Insulin Resistance in Male Mice. Cell Rep. 2016; 16(7):1903-14.
35. Imamura H, Shimada R, Kubota M, et al. Preoperative portal vein embolization: an audit of 84 patients. Hepatology. 1999; 29(4):1099-105.
36. Kawai T, Yokoyama Y, Kawai S, et al. Does estrogen contribute to the hepatic regeneration following portal branch ligation in rats? Am J Physiol Gastrointest Liver Physiol. 2007; 292(2):G582-9.
37. Umeda M, Hiramoto M, et al. Partial hepatectomy induces delayed hepatocyte proliferation and normal liver regeneration in ovariectomized mice. Clinical and Experimental Gastroenterology. 2015; 8:175-82.
38. Dai G, Bustamante J J, Myronovych A, et al. Maternal Hepatic Growth Response to Pregnancy in the Mouse. Experimental biology and medicine (Maywood, N.J.). 2011; 236(11): 1322-32.
39. Gershbein L L. Pregnancy and liver regeneration in partially hepatectomized rats. Proc Soc Exp Biol Med. 1958; 99(3):716-7.
40. Clocchiatti A, Cora E, Zhang Y, et al. Sexual dimorphism in cancer. Nat Rev Cancer. 2016; 16 (5):330-339.
41. Naugler W E, Sakurai T, Kim S, et al. Gender disparity in liver cancer due to sex differences in MyD88-dependent IL-6 production. Science. 2007; 317(5834):121-4.
42. Wei T, Chen W, Wen L, et al. G protein-coupled estrogen receptor deficiency accelerates liver tumorigenesis by enhancing inflammation and fibrosis. Cancer Lett. 2016; 382(2): 195-202.
43. Li Z, Tuteja G, Schug J, et al. Foxa1 and Foxa2 are essential for sexual dimorphism in liver cancer. Cell. 2012; 148(1-2):72-83.
44. Taper H S. The effect of estradiol-17-phenylpropionate and estradiol benzoate on N-nitrosomorpholine-induced liver carcinogenesis in ovariectomized female rats. Cancer. 1978; 42(2):462-7.
45. Lee C H, and Edwards A M. Stimulation of DNA synthesis and c-fos mRNA expression in primary rat hepatocytes by estrogens. Carcinogenesis. 2001; 22(9): 1473-81.
46. Chow P K H, Tai B-C, Tan C-K, et al. High-dose tamoxifen in the treatment of inoperable hepatocellular carcinoma: A multicenter randomized controlled trial. Hepatology. 2002; 36(5):1221-6.
47. Barbare J-C, Bouché O, Bonnetain F, et al. Randomized controlled trial of tamoxifen in advanced hepatocellular carcinoma. J Clin Oncol. 2005; 23(19):4338-46.
48. Dragan Y P, Xu Y D, and Pitot H C. Tumor promotion as a target for estrogen/antiestrogen effects in rat hepatocarcinogenesis. Prev Med. 1991; 20(1):15-26.
49. Williams G M, Iatropoulos M J, and Karlsson S. Initiating activity of the anti-estrogen tamoxifen, but not toremifene in rat liver. Carcinogenesis. ENGLAND; 1997; 18(11):2247-53.
50. Prossnitz E R, and Barton M. The G protein-coupled estrogen receptor GPER in health and disease. Nature reviews. Endocrinology. 2011; 7(12):715-26.
51. Evans N J, Bayliss A L, Reale V, et al. Characterisation of Signalling by the Endogenous GPER1 (GPR30) Receptor in an Embryonic Mouse Hippocampal Cell Line (mHippoE-18). PLoS One. 2016; 11(3):e0152138.

52. Villanueva A, Chiang D Y, Newell P, et al. Pivotal role of mTOR signaling in hepatocellular carcinoma. Gastroenterology. 2008; 135(6):1972-83, 1983.e1-11.
53. Chen J-S, Wang Q, Fu X-H, et al. Involvement of PI3K/PTEN/AKT/mTOR pathway in invasion and metastasis in hepatocellular carcinoma: Association with MMP-9. Hepatol Res. 2009; 39(2):177-86.
54. Forbes S A, Beare D, Gunasekaran P, et al. COSMIC: exploring the world's knowledge of somatic mutations in human cancer. Nucleic Acids Research. 2015; 43(Database issue):D805-11.
55. Schulze K, Imbeaud S, Letouzé E, et al. Exome sequencing of hepatocellular carcinomas identifies new mutational signatures and potential therapeutic targets. Nature Genetics. 2015; 47(5):505-511.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of treating a subject having liver cancer, the method comprising administering a therapeutically effective amount of an inhibitor of G protein-coupled estrogen receptor 1 (GPER1), thereby treating the liver cancer in the subject.

2. The method of claim 1, wherein the liver cancer comprises hepatocellular carcinoma (HCC), cholangiocarcinoma, fibrolamellar carcinoma, or hepatoblastoma.

3. The method of claim 1, wherein the subject has been diagnosed with hepatic steatosis, a hepatitis B viral infection, a hepatitis C viral infection, or cirrhosis.

4. The method of claim 1, wherein the inhibitor of GPER1 is an antagonist of GPER1.

5. The method of claim 1, wherein the inhibitor of GPER1 is G-15 or G-36.

6. The method of claim 1, wherein the inhibitor of GPER1 inhibits the expression of gper 1.

7. The method of claim 6, wherein the inhibitor of GPER1 is an inhibitory nucleic acid selected from the group consisting of a locked nucleic acid (LNA) molecule, a short hairpin RNA (shRNA) molecule, a small inhibitory RNA (siRNA) molecule, an antisense nucleic acid molecule, a peptide nucleic acid molecule, a morpholino, and a ribozyme.

8. The method of claim 6, wherein the inhibitor of GPER1 comprises a RNA-guided nuclease system selected from the group consisting of a zinc finger nuclease system, a transcription activator-like effector nuclease (TALEN) system, a meganuclease system, or a CRISPR/Cas9 system.

9. The method of claim 1, wherein the inhibitor of GPER1 is an anti-GPER1 antibody.

10. A method of selecting a subject for treatment with an inhibitor of GPER1, the method comprising:
    obtaining a liver tissue sample from the subject;
    performing an assay to determine whether GPER1-positive hepatocytes are present in the liver tissue sample;
    identifying a subject as having GPER1-positive hepatocytes; and
    selecting the identified subject for treatment with an inhibitor of GPER1.

11. The method of claim 10, wherein the subject has been diagnosed with cirrhosis.

12. The method of claim 10, wherein the subject has been diagnosed with liver cancer.

13. The method of claim 10, wherein the subject has been diagnosed with a hepatitis C viral infection or a hepatitis B viral infection.

14. The method of claim 10, wherein the liver cancer comprises hepatocellular carcinoma (HCC), cholangiocarcinoma, fibrolamellar carcinoma, or hepatoblastoma.

15. The method of claim 10, wherein the assay is an immunohistochemical assay.

16. The method of claim 10, wherein the subject is a male subject.

17. The method of claim 10, further comprising administering therapeutically effective amount of an inhibitor of GPER1 to the subject.

\* \* \* \* \*